US010921327B2

(12) United States Patent
Wang et al.

(10) Patent No.: US 10,921,327 B2
(45) Date of Patent: Feb. 16, 2021

(54) PROBES FOR QUANTITATIVE IMAGING OF THIOLS IN VARIOUS ENVIRONMENTS

(71) Applicant: Baylor College of Medicine, Houston, TX (US)

(72) Inventors: Jin Wang, Sugar Land, TX (US); Xiqian Jiang, Houston, TX (US); Jianwei Chen, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 357 days.

(21) Appl. No.: 15/502,378

(22) PCT Filed: Aug. 10, 2015

(86) PCT No.: PCT/US2015/044456
§ 371 (c)(1),
(2) Date: Feb. 7, 2017

(87) PCT Pub. No.: WO2016/025382
PCT Pub. Date: Feb. 18, 2016

(65) Prior Publication Data

US 2017/0219599 A1 Aug. 3, 2017

Related U.S. Application Data

(60) Provisional application No. 62/035,400, filed on Aug. 9, 2014, provisional application No. 62/093,538, filed on Dec. 18, 2014.

(51) Int. Cl.
*G01N 33/58* (2006.01)
*G01N 33/68* (2006.01)
(Continued)

(52) U.S. Cl.
CPC ....... *G01N 33/6815* (2013.01); *C07D 311/16* (2013.01); *G01N 33/582* (2013.01); *G01N 33/84* (2013.01); *Y10T 436/182* (2015.01)

(58) Field of Classification Search
CPC .. G01N 33/58; G01N 33/582; G01N 33/6815; C07D 311/12; C07D 311/14; C07D 311/16; Y10T 436/182
See application file for complete search history.

(56) References Cited

U.S. PATENT DOCUMENTS

| | | | | |
|---|---|---|---|---|
| 10,215,757 | B2 * | 2/2019 | Kim | G01N 33/5008 |
| 10,620,215 | B2 * | 4/2020 | Kim | G01N 33/5008 |
| 2017/0307624 | A1 | 10/2017 | Kim et al. | |

FOREIGN PATENT DOCUMENTS

| | | |
|---|---|---|
| EP | 1273971 B1 | 2/2010 |
| KR | 2012130906 | 12/2012 |

(Continued)

OTHER PUBLICATIONS

Tian, H. et al. "Colorimetric and ratiometric fluorescent detection of sulfite in water via cationic surfactant-promoted addition of sulfite to α,β-unsaturated ketone," Analytica Chimica Acta, vol. 788, Jul. 25, 2013, pp. 165-170 (Year: 2013).*

(Continued)

*Primary Examiner* — Christopher Adam Hixson
*Assistant Examiner* — Michelle Adams
(74) *Attorney, Agent, or Firm* — Winstead PC

(57) ABSTRACT

Embodiments of the present disclosure pertain to methods of detecting a thiol in an environment by exposing the environment to a probe molecule that contains a marker and a thiol responsive group. The thiol responsive group reversibly reacts with the thiol in the environment to form a probe-thiol adduct. This in turn causes a ratiometric change in a spectrometric property of the probe molecule and the probe-thiol adduct, which can then be correlated to the presence of the thiol in the environment. The correlation can occur by quantifying the thiol concentration in the environment. In addition, thiol detection can occur in real-time. Further embodiments of the present disclosure pertain to (Continued)

Figure 1:
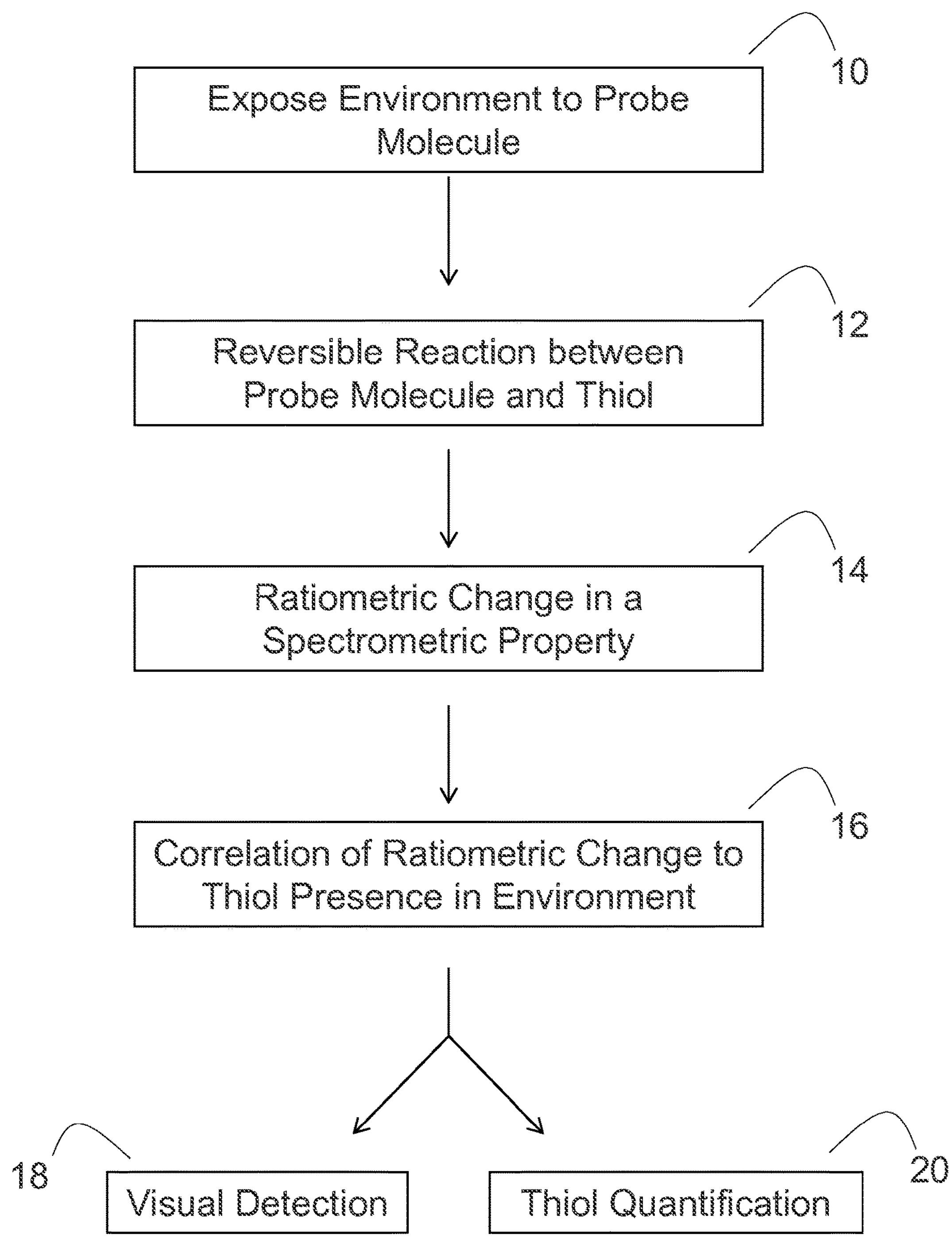

probe molecules that are utilized for detecting a thiol in an environment. In some embodiments, the probe molecule includes a marker and a thiol responsive group. In some embodiments, the probe molecule also includes an organelle targeting moiety.

28 Claims, 36 Drawing Sheets

(51) Int. Cl.
*C07D 311/16* (2006.01)
*G01N 33/84* (2006.01)

(56) References Cited

FOREIGN PATENT DOCUMENTS

WO WO-2007042321 A2 4/2007
WO WO-2016080759 A2 5/2016

OTHER PUBLICATIONS

Lou, Z. et al. "A fluorescent probe for rapid detection of thiols and imaging of thiols reducing repair and H2O2 oxidative stress cycles in living cells," Chem. Commun., 2013, 49, 391-393, First published on Oct. 31, 2012. (Year: 2012).*

Supporting Information for Kim, G.-J. et al. "Ratiometric Fluorescence Imaging of Cellular Glutathione," Org. Lett.2011, 13, 11, 2799-2801. (Year: 2011).*

Geoffroy-Chapotot, C. et al. "Three-Dimensional Fluorescence Microscopy of Endothelial Cells Labeled with Coumarins," Journal of Fluorescence, Jun. 2000, vol. 10, Issue 2, pp. 203-203 (Year: 2000).*

Teiten, M.-H. et al. "Specific fluorescent tracers. Imaging and applications for photodynamic therapy," Comptes Rendus Biologies 325 (2002) 487-493 (Year: 2002).*

Grimm, J.B. et al. "A general method to improve fluorophores for live-cell and single-molecule microscopy," Nature Methods, vol. 12, pp. 244-250, published online Jan. 19, 2015. (Year: 2015).*

International Preliminary Report on Patentability for PCT/US2015/044456, dated Feb. 23, 2017.

International Search Report and Written Opinion for PCT/US15/44456, dated May 25, 2016.

Niu, Ly et al. BODIPY-Based Ratio metric Fluorescent Sensor for Highly Selective Detection of Glutathione over Cysteine and Homocysteine. Journal of the American Chemical Society, vol. 134, Nov. 2, 2012, pp. 18928-18931.

Chen, X et al. Fluorescent and colorimetric probes for detection of thiols. Chemical Society Reviews, vol. 39, No. 6, Jun. 2010, pp. 1861-2336.

Dickinson, BC et al. Mitochondrial-targeted fluorescent probes for reactive oxygen species. Current Opinion in Chemichal Biology, vol. 14, No. 1, Feb. 2010, pp. 50-56.

Cho, et al., A Coumarin-based Fluorescence Sensor for the Reversible Detection of Thiols, Chem. Lett. 2012, 41, 1611-1612.

Lippert et al., Reaction-Based Fluorescent Probes for Selective Imaging of Hydrogen Sulfide in Living Cells, JACS 2011, 133, 10078.

Chung, C.; Srikun, D.; Lim, C. S.; Chang, C. J.; Cho, B. R., A two-photon fluorescent probe for ratiometric imaging of hydrogen peroxide in live tissue, Chem Commun 2011, 47, 9618.

Youjun Yang, et. al., A Highly Selective Low-Background Fluorescent Imaging Agent for Nitric Oxide, J. Am. Chem. Soc. 2010, 132, 13114.

Xu Wang, et. al., A near-infrared ratiometric fluorescent probe for rapid and highly sensitive imaging of endogenous hydrogen sulfide in living cells, Chem. Sci. 2013, 4, 2551.

Shi, B., and Greaney, M. F. (2005) Reversible Michael addition of thiols as a new tool for dynamic combinatorial chemistry, Chem. Commun., 886-888.

Albers, A. E., Okreglak, V. S., and Chang, C. J. (2006) A FRET-based approach to ratiometric fluorescence detection of hydrogen peroxide, J. Am. Chem. Soc. 128, 9640-9641.

Lomaestro, B. M., and Malone, M. (1995) Glutathione in health and disease: pharmacotherapeutic issues, Ann. Pharmacother. 29, 1263-1273.

Winther, J. R., and Thorpe, C. (2014) Quantification of thiols and disulfides, Biochim. Biophys. Acta. 1840, 838-846.

Hanson, G. T., Aggeler, R., Oglesbee, D., Cannon, M., Capaldi, R. A., Tsien, R. Y., and Remington, S. J. (2004) Investigating mitochondrial redox potential with redox-sensitive green fluorescent protein indicators, J. Biol. Chem. 279, 13044-13053.

Gutscher, M., Pauleau, A. L., Marty, L., Brach, T., Wabnitz, G. H., Samstag, Y., Meyer, A. J., and Dick, T. P. (2008) Real-time imaging of the intracellular glutathione redox potential, Nat. Methods 5, 553-559.

Lim, C. S., Masanta, G., Kim, H. J., Han, J. H., Kim, H. M., and Cho, B. R. (2011) Ratiometric detection of mitochondrial thiols with a two-photon fluorescent probe, J. Am. Chem. Soc. 133, 11132-11135.

Kim, G. J., Lee, K., Kwon, H., and Kim, H. J. (2011) Ratiometric fluorescence imaging of cellular glutathione, Org. Lett. 13, 2799-2801.

Nagano, T., and Yoshimura, T. (2002) Bioimaging of nitric oxide, Chem. Rev. 102, 1235-1270.

Yuan, L., Lin, W., Xie, Y., Chen, B., and Song, J. (2011) Development of a ratiometric fluorescent sensor for ratiometric imaging of endogenously produced nitric oxide in macrophage cells, Chem. Commun. 47, 9372-9374.

Srikun, D., Miller, E. W., Domaille, D. W., and Chang, C. J. (2008) An ICT-based approach to ratiometric fluorescence imaging of hydrogen peroxide produced in living cells, J. Am. Chem. Soc. 130, 4596-4597.

Bae, S. K., Heo, C. H., Choi, D. J., Sen, D., Joe, E. H., Cho, B. R., and Kim, H. M. (2013) A ratiometric two-photon fluorescent probe reveals reduction in mitochondrial H2S production in Parkinson's disease gene knockout astrocytes, J. Am. Chem. Soc. 135, 9915-9923.

Chen, Y., Zhu, C., Yang, Z., Chen, J., He, Y., Jiao, Y., He, W., Qiu, L., Cen, J., and Guo, Z. (2013) A ratiometric fluorescent probe for rapid detection of hydrogen sulfide in mitochondria, Angew. Chem., Int. Ed. 52, 1688-1691.

Wan, Q., Song, Y., Li, Z., Gao, X., and Ma, H. (2013) In vivo monitoring of hydrogen sulfide using a cresyl violet-based ratiometric fluorescence probe, Chem. Commun. 49, 502-504.

Wang, B., Li, P., Yu, F., Chen, J., Qu, Z., and Han, K. (2013) A near-infrared reversible and ratiometric fluorescent probe based on Se-BODIPY for the redox cycle mediated by hypobromous acid and hydrogen sulfide in living cells, Chem. Commun. 49, 5790-5792.

Wu, M. Y., Li, K., Hou, J. T., Huang, Z., and Yu, X. Q. (2012) A selective colorimetric and ratiometric fluorescent probe for hydrogen sulfide, Org. Biomol. Chem. 10, 8342-8347.

Yu, F., Li, P., Song, P., Wang, B., Zhao, J., and Han, K. (2012) An ICT-based strategy to a colorimetric and ratiometric fluorescence probe for hydrogen sulfide in living cells, Chem. Commun. 48, 2852-2854.

Johansson, M. H. (2012) Reversible Michael additions: covalent inhibitors and prodrugs, Mini Rev. Med. Chem. 12, 1330-1344.

Higley, M. J., and Sabatini, B. L. (2008) Calcium signaling in dendrites and spines: practical and functional considerations, Neuron 59, 902-913.

Acharya, J. R., Zhang, H., Li, X., and Nesterov, E. E. (2009) Chemically controlled amplified ratiometric fluorescence in surface-immobilized end-capped oligo(p-phenylene ethynylene)s, J. Am. Chem. Soc. 131, 880-881.

Lin, V. S., Lippert, a. R., and Chang, C. J. (2013) Cell-trappable fluorescent probes for endogenous hydrogen sulfide signaling and imaging H2O2-dependent H2S production, Proc. Natl. Acad. Sci. U.S.A. 110, 7131-7135.

(56) References Cited

OTHER PUBLICATIONS

N. Ballatori, C. L. Hammond, J. B. Cunningham, S. M. Krance and R. Marchan, Molecular mechanisms of reduced glutathione transport: role of the MRP/CFTR/ABCC and OATP/SLC21A families of membrane proteins, Toxicology and applied pharmacology, 2005, 204, 238-255.

Yin, J., Kwon, Y., Kim, D., Lee, D., Kim, G., Hu, Y., Ryu, J. H., and Yoon, J. (2014) Cyanine-based fluorescent probe for highly selective detection of glutathione in cell cultures and live mouse tissues, J. Am. Chem. Soc. 136, 5351-5358.

Jung, H. S., Chen, X., Kim, J. S., and Yoon, J. (2013) Recent progress in luminescent and colorimetric chemosensors for detection of thiols, Chem. Soc. Rev. 42, 6019-6031.

Yi, L., Li, H., Sun, L., Liu, L., Zhang, C., and Xi, Z. (2009) A highly sensitive fluorescence probe for fast thiol-quantification assay of glutathione reductase, Angew. Chem., Int. Ed. 48, 4034-4037.

Shao, N., Jin, J., Wang, H., Zheng, J., Yang, R., Chan, W., and Abliz, Z. (2010) Design of bis-spiropyran ligands as dipolar molecule receptors and application to in vivo glutathione fluorescent probes, J. Am. Chem. Soc. 132, 725-736.

Sun, Y. Q., Liu, J., Zhang, H., Huo, Y., Lv, X., Shi, Y., and Guo, W. (2014) A Mitochondria-Targetable Fluorescent Probe for Dual-Channel NO Imaging Assisted by Intracellular Cysteine and Glutathione, J. Am. Chem. Soc. 136, 12520-12523.

Yu, F., Li, P., Wang, B., and Han, K. (2013) Reversible near-infrared fluorescent probe introducing tellurium to mimetic glutathione peroxidase for monitoring the redox cycles between peroxynitrite and glutathione in vivo, J. Am. Chem. Soc. 135, 7674-7680.

McMahon, B. K., and Gunnlaugsson, T. (2012) Selective detection of the reduced form of glutathione (GSH) over the oxidized (GSSG) form using a combination of glutathione reductase and a Tb(III)-cyclen maleimide based lanthanide luminescent 'switch on' assay, J. Am. Chem. Soc. 134, 10725-10728.

Ahn, Y. H., Lee, J. S., and Chang, Y. T. (2007) Combinatorial rosarnine library and application to in vivo glutathione probe, J. Am. Chem. Soc. 129, 4510-4511.

Wang, K., Peng, H., and Wang, B. (2014) Recent Advances in Thiol and Sulfide Reactive Probes, J. Cell. Biochem. 115, 1077-1022.

Montero, D., Tachibana, C., Rahr Winther, J., and Appenzeller-Herzog, C. (2013) Intracellular glutathione pools are heterogeneously concentrated, Redox Biol. 1, 508-513.

Reynaert, N. L., van der Vliet, A., Guala, A. S., McGovern, T., Hristova, M., Pantano, C., Heintz, N. H., Heim, J., Ho, Y. S., Matthews, D. E., Wouters, E. F., and Janssen-Heininger, Y. M. (2006) Dynamic redox control of NF-kappaB through glutaredoxin-regulated S-glutathionylation of inhibitory kappaB kinase beta, Proc. Natl. Acad. Sci. U.S.A. 103, 13086-13091.

Zhang, L., Murphy, C. S., Kuang, G. C., Hazelwood, K. L., Constantino, M. H., Davidson, M. W., and Zhu, L. (2009) A fluorescent heteroditopic ligand responding to free zinc ion over six orders of magnitude concentration range, Chem. Commun., 7408-7410.

Sreenath, K., Allen, J. R., Davidson, M. W., and Zhu, L. (2011) A FRET-based indicator for imaging mitochondrial zinc ions, Chem. Commun. 47, 11730-11732.

Nolan, E. M., Jaworski, J., Okamoto, K., Hayashi, Y., Sheng, M., and Lippard, S. J. (2005) QZ1 and QZ2: rapid, reversible quinoline-derivatized fluoresceins for sensing biological Zn(II), J. Am. Chem. Soc. 127, 16812-16823.

Nolan, E. M., and Lippard, S. J. (2009) Small-molecule fluorescent sensors for investigating zinc metalloneurochemistry, Acc. Chem. Res. 42, 193-203.

Tomat, E., Nolan, E. M., Jaworski, J., and Lippard, S. J. (2008) Organelle-specific zinc detection using zinpyr-labeled fusion proteins in live cells, J. Am. Chem. Soc. 130, 15776-15777.

Lippert, A. R. (2014) Designing reaction-based fluorescent probes for selective hydrogen sulfide detection, J. Inorg. Biochem. 133, 136-142.

Paige, J. S., Nguyen-Duc, T., Song, W., and Jaffrey, S. R. (2012) Fluorescence imaging of cellular metabolites with RNA, Science 335, 1194.

Strack, R. L., and Jaffrey, S. R. (2013) New approaches for sensing metabolites and proteins in live cells using RNA, Curr. Opin. Chem. Biol. 17, 651-655.

Jones, D. P., Go, Y. M., Anderson, C. L., Ziegler, T. R., Kinkade, J. M., Jr., and Kirlin, W. G. (2004) Cysteine/cystine couple is a newly recognized node in the circuitry for biologic redox signaling and control, FASEB J. 18, 1246-1248.

Rahman, I., Kode, A., and Biswas, S. K. (2006) Assay for quantitative determination of glutathione and glutathione disulfide levels using enzymatic recycling method, Nat. Protoc. 1, 3159-3165.

Urano et al., Rational design of reversible fluorescent probes for live-cell imaging and quantification of fast glutathione dynamics, Nat. Chem. 9, 279-286 (2017).

Yoon et al., A Reversible Fluorescent Probe for Real-Time Quantitative Monitoring of Cellular Glutathione, Angew. Chem. 56, 5812-5816 (2017).

Jiang X, Yu Y, Chen J, Zhao M, Chen H, Song X, Matzuk AJ, Carroll SL, Tan X, Sizovs A, Cheng N, Wang MC, & Wang J (2015) Quantitative imaging of glutathione in live cells using a reversible reaction-based ratiometric fluorescent probe. *ACS chemical biology* 10(3):864-874.

Chen J, Jiang X, Carroll SL, Huang J, & Wang J (2015) Theoretical and Experimental Investigation of Thermodynamics and Kinetics of Thiol-Michael Addition Reactions: A Case Study of Reversible Fluorescent Probes for Glutathione Imaging in Single Cells. *Organic letters* 17(24):5978-5981.

Jiang X, Chen J, Bajic A, Zhang C, Song X, Carroll SL, Cai Z, Tang M, Xue M, Cheng N, Schaaf CP, Li F, MacKenzie KR, Ferreon ACM, Xia F, Wang MC, Maletic-Savatic M, & Wang J (2017) Quantitative Real-Time Imaging of Glutathione. *Nature communications* 8:16087-16098.

Liu Z, Zhou X, Miao Y, Hu Y, Kwon N, Wu X, & Yoon J (2017) A Reversible Fluorescent Probe for Real-time Quantitative Monitoring of Cellular Glutathione. *Angewandte Chemie* 56(21):5812-5816.

Umezawa K, Yoshida M, Kamiya M, Yamasoba T, & Urano Y (2017) Rational design of reversible fluorescent probes for live-cell imaging and quantification of fast glutathione dynamics. *Nature chemistry* 9:279-286.

Chen J, Jiang X, Zhang C, MacKenzie KR, Stossi F, Palzkill T, Wang MC, & Wang J (2017) Reversible Reaction-Based Fluorescent Probe for Real-Time Imaging of Glutathione Dynamics in Mitochondria. *ACS Sens* 2(9):1257-1261.

Jiang X, Zhang C, Chen J, Choi S, Zhou Y, Zhao M, Song X, Chen X, Maletic-Savatic M, Palzkill TG, Moore D, Wang MC, & Wang J (2019) Quantitative Real-Time Imaging of Glutathione with Sub-Cellular Resolution. *Antioxidants & redox signaling*, 30(16):1900-1910.

Han et al., Redox-Responsive Fluorescent Probes with Different Design Strategies, Acc. Chem. Res., 2015, 48, 1358-1368.

* cited by examiner

A

B

Summary table of measurements from the example cell

| Location | Area | Channel 1 ($\lambda_{ex}$=405 nm) | | | Channel 2 ($\lambda_{ex}$=488 nm) | | | Ratio of CH1/CH2 |
|---|---|---|---|---|---|---|---|---|
| | | Average | Min | Max | Average | Min | Max | |
| Background | NA | 177.382 | 148 | 573 | 172.086 | 153 | 240 | NA |
| 1 | 2.643 | 448.100 | 163 | 931 | 397.218 | 200 | 629 | 1.205 |
| 2 | 3.171 | 624.341 | 174 | 1798 | 505.447 | 312 | 760 | 1.343 |
| 3 | 3.171 | 674.758 | 190 | 2423 | 508.545 | 275 | 865 | 1.480 |
| 4 | 3.460 | 502.007 | 168 | 1454 | 447.910 | 227 | 689 | 1.179 |
| 5 | 2.907 | 603.198 | 160 | 1589 | 485.702 | 283 | 787 | 1.360 |
| 6 | 2.907 | 454.380 | 156 | 1857 | 378.107 | 186 | 817 | 1.347 |
| 7 | 3.460 | 476.806 | 153 | 1347 | 417.312 | 210 | 748 | 1.223 |
| 8 (excluded) | 1.946 | 749.309 | 209 | 4095 | 512.259 | 306 | 795 | 1.683 |
| Ratio average of the example cell: | | | | | 1.305 ± 0.107 | | | |

A

$$[A] + [P] \rightleftharpoons [AP]$$

$$K_d = \frac{[A][P]}{[AP]}$$

$$[A] = K_d \frac{[AP]}{[P]}$$

B

A

GSH Probe Library TQG-CN TQG-RT1

B

| | Thermodynamics | | | |
|---|---|---|---|---|
| X = | $K_d$ mM | $\Delta G°$ kcal·mol$^{-1}$ | $\Delta G_{calc}$ kcal·mol$^{-1}$ | $\Delta G_{calc} - \Delta G°$ kcal·mol$^{-1}$ |
| -H | 0.43 | -4.59 | -4.94 | -0.35 |
| -F | 0.60 | -4.39 | -4.41 | -0.02 |
| -Br | 1.60 | -3.81 | -4.80 | -0.99 |
| $-NO_2$ | 1.67 | -3.78 | -3.95 | -0.16 |

C

| | Kinetics | | | | |
|---|---|---|---|---|---|
| | forward | | reverse | | DFT |
| X = | $t_{1/2}$ min | $k_f$ M$^{-1}$·min$^{-1}$ | $t_{1/2}$ min | $k_r$ min$^{-1}$ | $\Delta G^{\ddagger}_{calc}$ kcal·mol$^{-1}$ |
| -H | 20.5 | 3.4 | 491.0 | $1.41 \times 10^{-3}$ | -2.59 |
| -F | 11.0 | 6.3 | 466.2 | $1.49 \times 10^{-3}$ | -3.13 |
| -Br | 7.7 | 9.0 | 219.9 | $3.15 \times 10^{-3}$ | -3.22 |
| $-NO_2$ | 5.7 | 12.2 | 188.5 | $3.68 \times 10^{-3}$ | -5.00 |

A

| Serial No. | Ram 17 | Ram 18 | Ram 20 | Ram 16 | Ram 19 |
|---|---|---|---|---|---|
| Structure | COOH | $O_2N$ COOH | $H_2N$ COOH | COOH | $H_2N$ COOH |
| **Freq (Probe)** | 2245 | 2246 | 2355 | 2356 | 2355 |
| **Freq (Adduct)** | 2243 | 2241 | 2362 | 2356 | 2362 |

B

C

| Serial No. | Ram 28 | Ram 33 | Ram 38 | Ram 45 |
|---|---|---|---|---|
| Structure | HN | $O_2N$ | Br | H |
| **Freq (Probe)** | 2229 | 2241 | 2237 | 2240 |
| **Freq (Adduct)** | 2257 | 2257 | 2259 | 2249 |

D

PROBES FOR QUANTITATIVE IMAGING OF THIOLS IN VARIOUS ENVIRONMENTS

CROSS-REFERENCE TO RELATED APPLICATIONS

This application claims priority to U.S. Provisional Patent Application No. 62/035,400, filed on Aug. 9, 2014; and U.S. Provisional Patent Application No. 62/093,538, filed on Dec. 18, 2014. The entirety of each of the aforementioned applications is incorporated herein by reference.

STATEMENT REGARDING FEDERALLY SPONSORED RESEARCH

Not applicable.

BACKGROUND

Thiols play important roles in maintaining redox homeostasis inside cells. However, current thiol probes cannot effectively provide meaningful quantitation of thiol concentrations in various environments, such as cells. Accordingly, a need exists for more effective probes and methods for the detection and quantification of various thiols.

SUMMARY

In some embodiments, the present disclosure pertains to methods of detecting a thiol in an environment by exposing the environment to a probe molecule that contains a marker and a thiol responsive group. The thiol responsive group reversibly reacts with the thiol in the environment to form a probe-thiol adduct. This in turn causes a ratiometric change in a spectrometric property of the probe molecule and the probe-thiol adduct, which can then be correlated to the presence of the thiol in the environment.

In some embodiments, the ratiometric change in a spectrometric property of the probe molecule and the probe-thiol adduct includes, without limitation, a shift in absorption, a shift in fluorescence, a shift in phosphorescence, a shift in luminescence, a shift in fluorescence polarization, a shift in fluorescence lifetime imaging (FLIM), a shift in infrared Raman scattering, a shift in emission spectra, a shift in stimulated emission, a shift in nuclear magnetic resonance (NMR), a shift in magnetic resonance imaging (MRI), a shift in mass spectrometry, a shift in static light scattering, a shift in dynamic light scattering, a shift in refractive index (RI), and combinations thereof. In some embodiments, the ratiometric change includes a change in an emission spectra.

In some embodiments, the correlation of the ratiometric change in a spectrometric property of the probe molecule and the probe-thiol adduct to the presence of a thiol in an environment occurs by visual detection of the ratiometric change. In some embodiments, the correlation occurs by quantifying the thiol concentration in the environment. In some embodiments, the quantifying occurs by comparing the ratiometric change of a spectrometric property of the probe molecule and the probe-thiol adduct in the environment to the ratiometric change of the spectrometric property of the probe molecule and the probe-thiol adduct in the presence of known concentrations of the thiol.

The methods of the present disclosure may be utilized to detect various types of thiols in an environment. For instance, in some embodiments, the thiol includes, without limitation, cysteine, homocysteine, methionine, glutathione, lipoic acid, coenzyme A, hydrogen sulfide, hydrosulfide anion, persulfide, thio-sulfate, sulfite, and combinations thereof. In some embodiments, the thiol includes glutathione.

The methods of the present disclosure may also be utilized to detect thiols in various environments. For instance, in some embodiments, the environment includes, without limitation, liquids, fluids, organic solvents, thiol-containing solutions, plasma, extracellular fluids, cellular extracts, cells, cytosol, organelles, in vitro environments, in vivo environments, and combinations thereof. In some embodiments, the environment includes cells that are at least part of a tissue, an organ, or an organism. In some embodiments, the environment is an organelle within a cell. In some embodiments, thiol detection occurs in real-time.

Further embodiments of the present disclosure pertain to the probe molecules that are utilized for detecting a thiol in an environment. In some embodiments, the probe molecule includes a marker and a thiol responsive group. In some embodiments, the probe molecule also includes an organelle targeting moiety.

FIGURES

FIG. 1 provides a scheme of a method of detecting a thiol in an environment.

Figure 2:
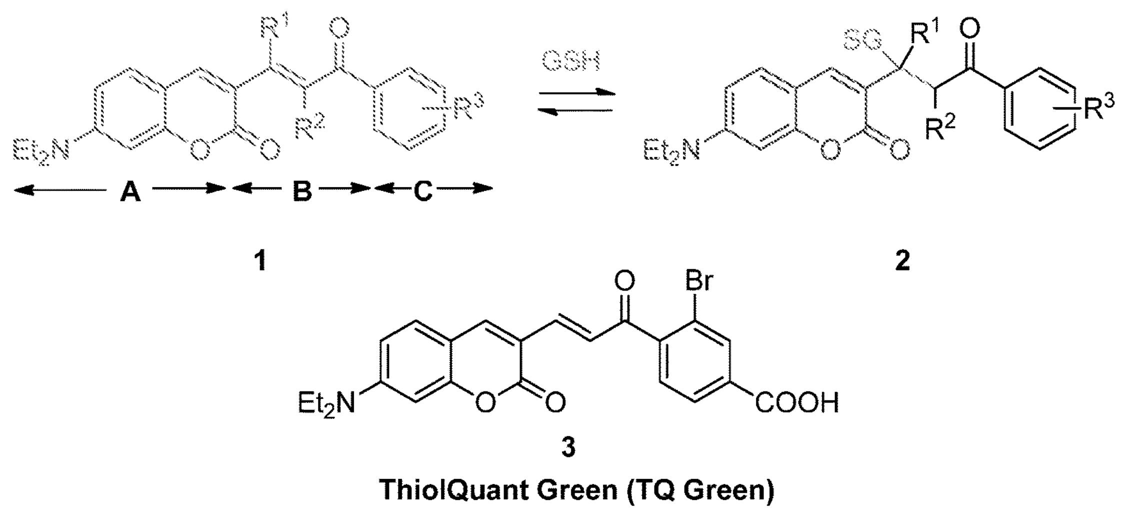

FIG. 2 provides a scheme for the modular design of glutathione (GSH) probes, and the Michael addition of GSH to a probe. A structure of ThiolQuant Green (TQ Green) is also shown.

Figure 3:
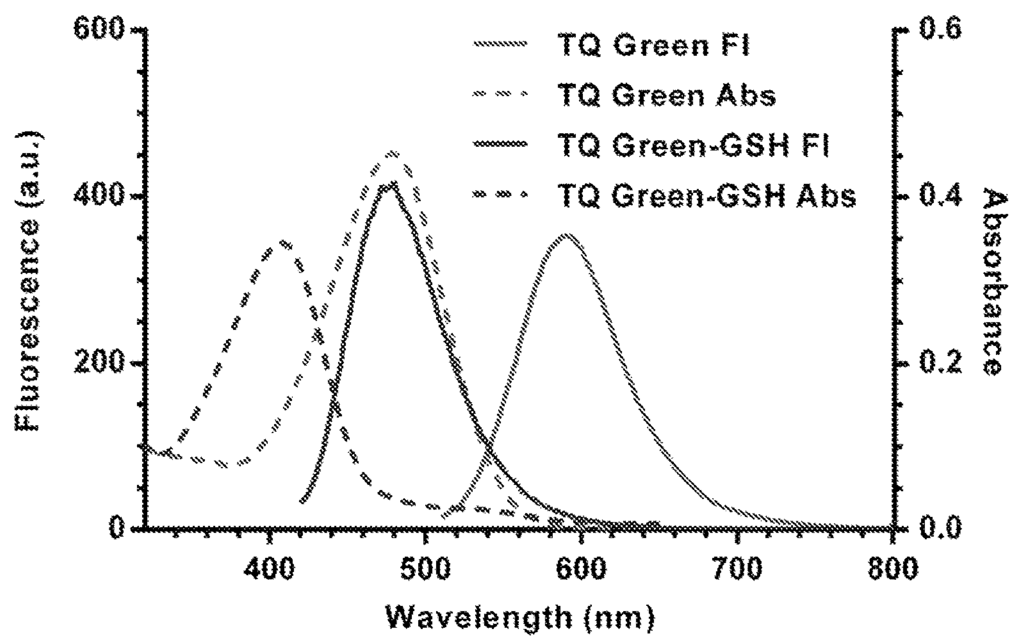

FIG. 3 provides UV-Vis and Fluorescence spectra of TQ Green ($\lambda_{ex}$=488 nm) and TQ Green-GSH ($\lambda_{ex}$=405 nm).

Figure 4:
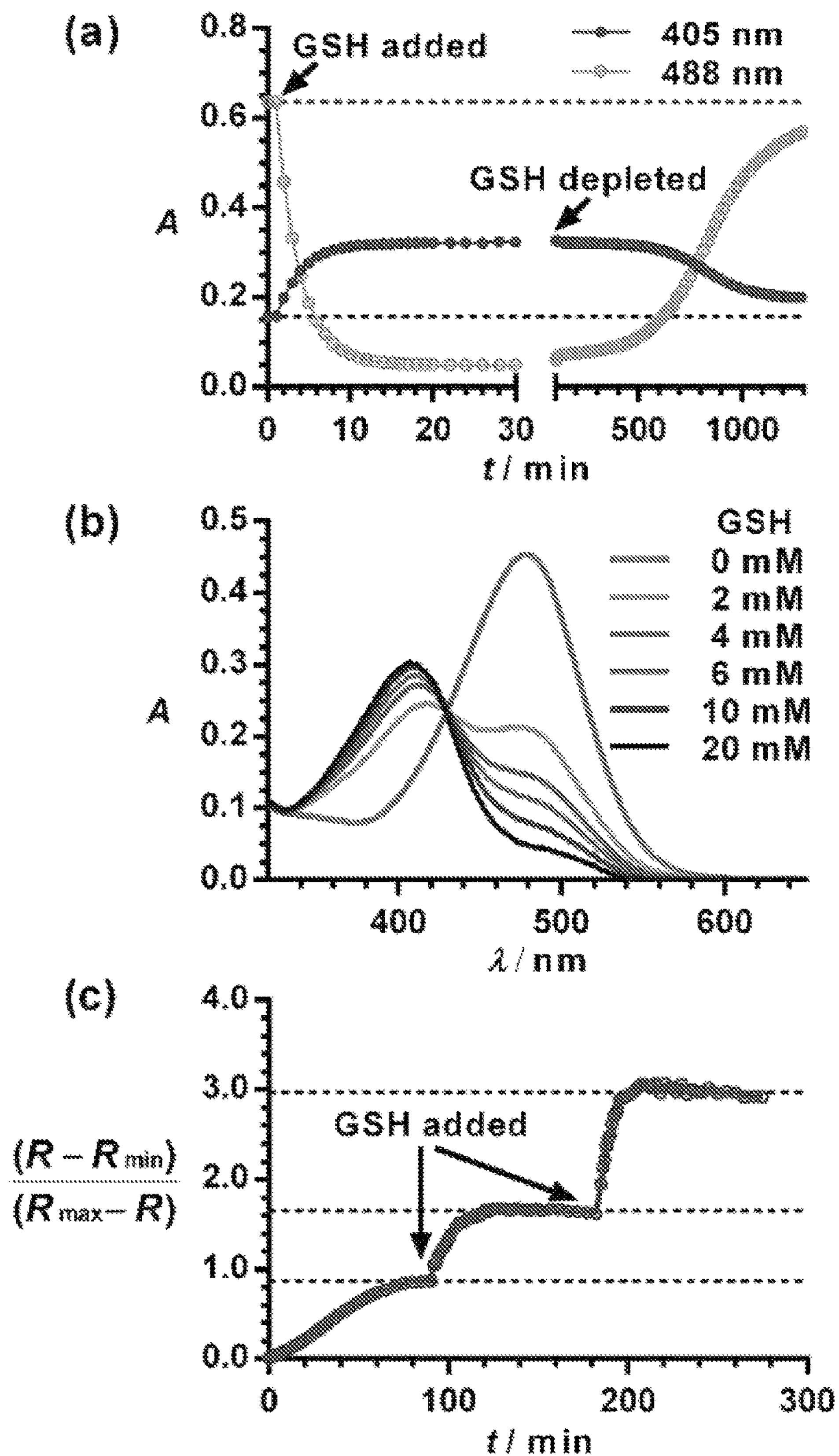

FIG. 4 provides data demonstrating the reversibility of the reaction between TQ Green and GSH. FIG. 4A provides data relating to the recovery of reacted TQ Green by depleting GSH. FIG. 4B provides data relating to the concentration dependent ratiometric spectra of TQ Green in PBS under anaerobic conditions for 18 hours. FIG. 4C provides data relating to the responsiveness of TQ Green to the concentration changes of GSH. $R_{min}$ and $R_{max}$ were measured at 0 and 80 mM of GSH, respectively.

Figure 5:
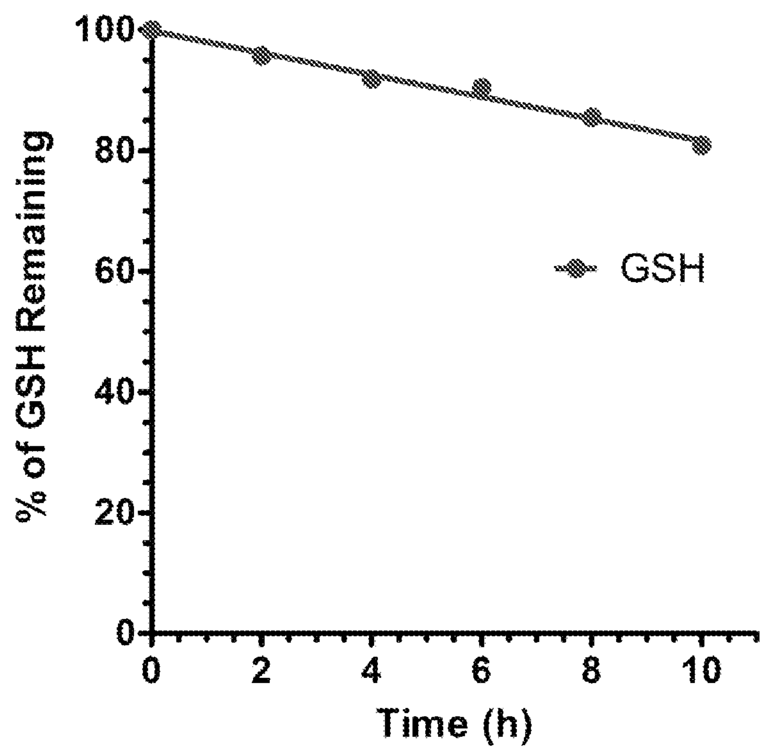

FIG. 5 provides data demonstrating the stability of GSH in air. A GSH solution (10 mM) was placed in a capped Eppendorf tube. Samples of solution were taken out for HPLC measurement every two hours. About 20% of GSH was oxidized over a 10 hour time period. The percentage was calculated from the HPLC peak area monitored at 254 nm.

Figure 6:
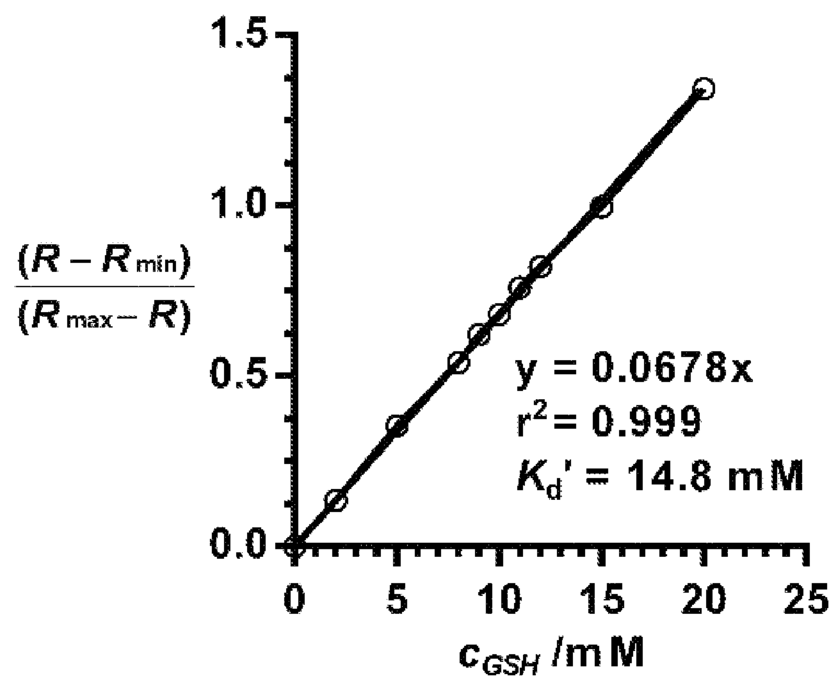

FIG. 6 shows a graph that demonstrates the linear relationship between $(R-R_{min})/(R_{max}-R)$ and GSH concentration. The reciprocal of the slope is the apparent dissociation constant $K_d'$. R is based on UV-vis absorption measurements.

Figure 7:
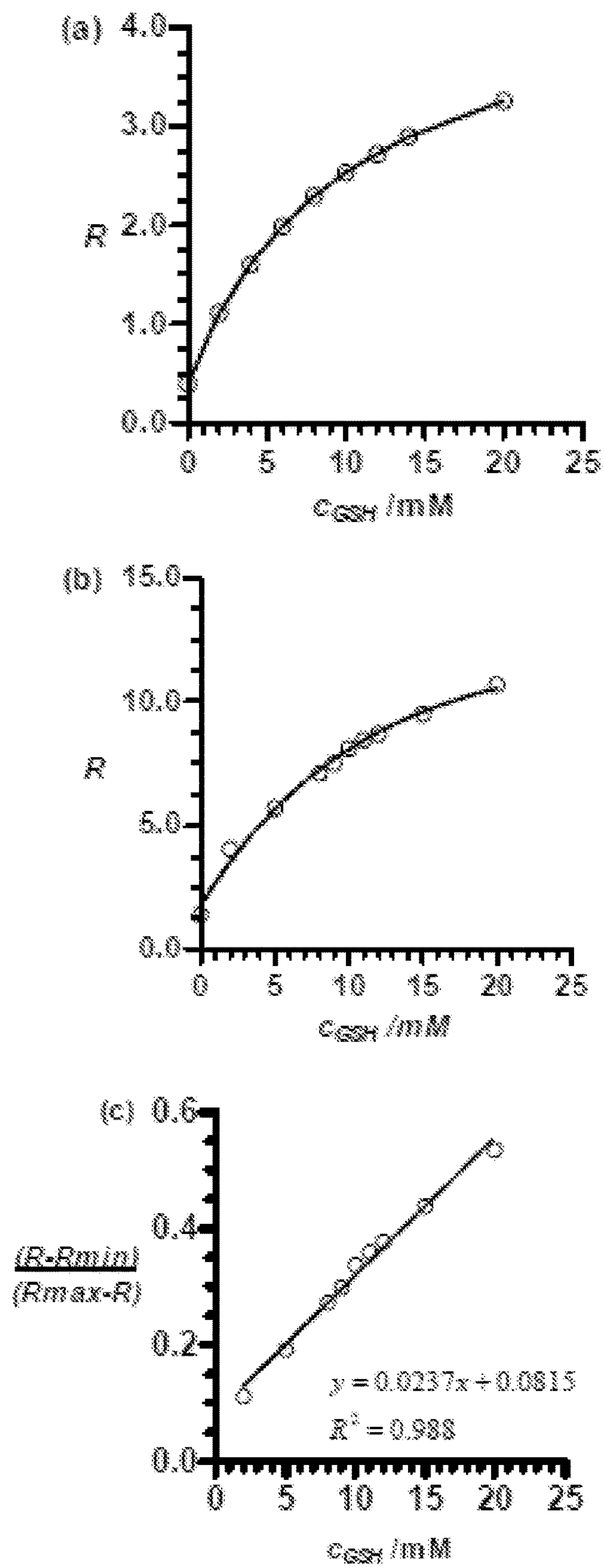

FIG. 7 provides calibration curves for TQ Green. FIG. 7A is the ratio R derived from absorption plotted against GSH concentration. R stands for the ratio of absorption signals between 405 and 488 nm. FIG. 7B shows the ratio R derived from fluorescence plotted against GSH concentration. FIG. 7C shows the linear relationship between $(R-R_{min})/(R_{max}-R)$ and GSH concentration based on fluorescence measurement. Fluorescent ratio R stands for ratio of signals between 468 nm ($\lambda_{ex}$=405 nm) and 592 nm ($\lambda_{ex}$=488 nm).

Figure 8:
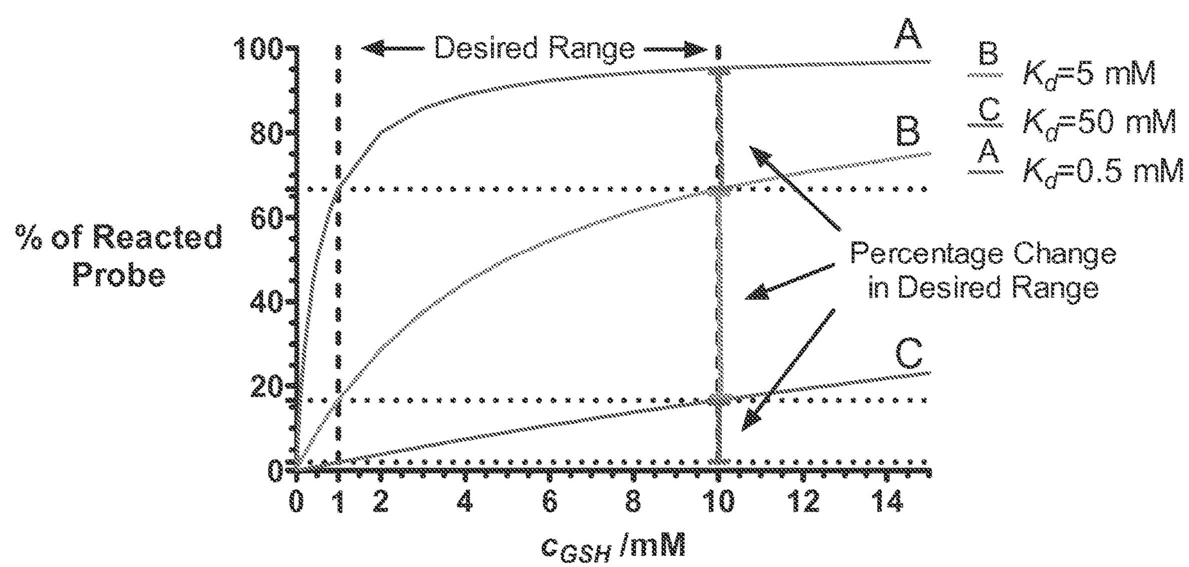

FIG. 8 shows the simulation of signal changes with different $K_d$ values. Proper $K_d$ values result in the largest signal change, allowing more accurate measurements. Using GSH as an example, if the expected range of GSH concentration is 1-10 mM, the optimal $K_d$ would be ~3 mM (orange curve B). Deviations from this $K_d$ will result in a weakened response to the concentration changes (blue and green curves). Additionally, the apparent dissociation constant $K_d'$ also depends on the relative signal intensities from the free and reacted probes.

Figure 9:
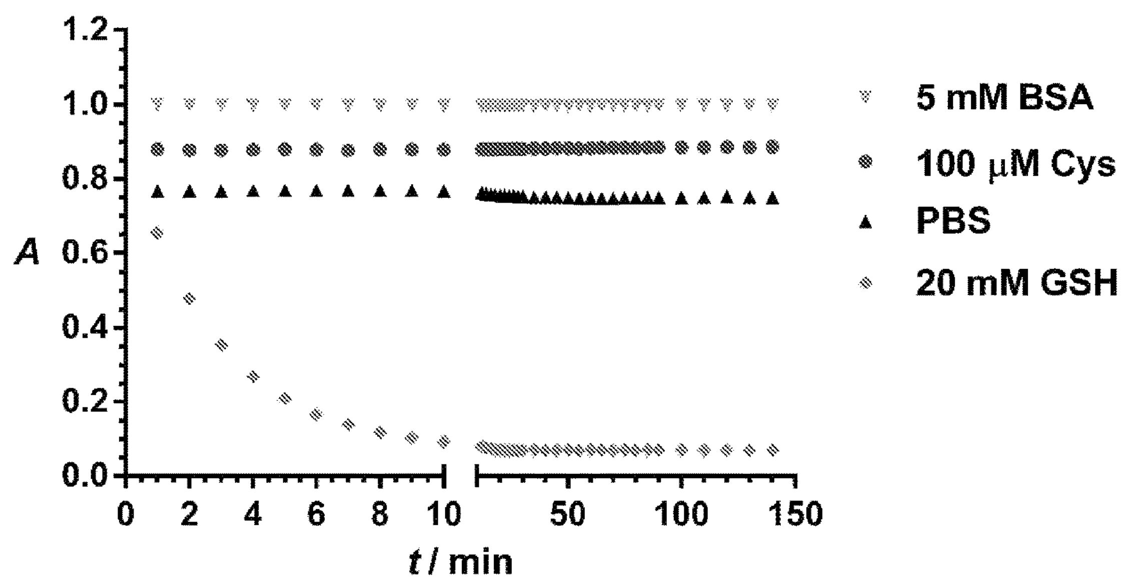

FIG. 9 shows the reaction specificity of TQ Green and GSH under physiological concentrations. For clarity, data points for TQ Green reaction with BSA, Cysteine, and PBS were offset by 0.1 units from each other on the y axis. Data points represent the absorbance of reaction mixtures of TQ Green (32 μM) with cysteine (100 μM, blue), BSA (5 mM, green), GSH (20 mM red) and water (black) in PBS (pH 7.4) at 480 nm, the maximum absorption wavelength for TQ Green.

Figure 10:
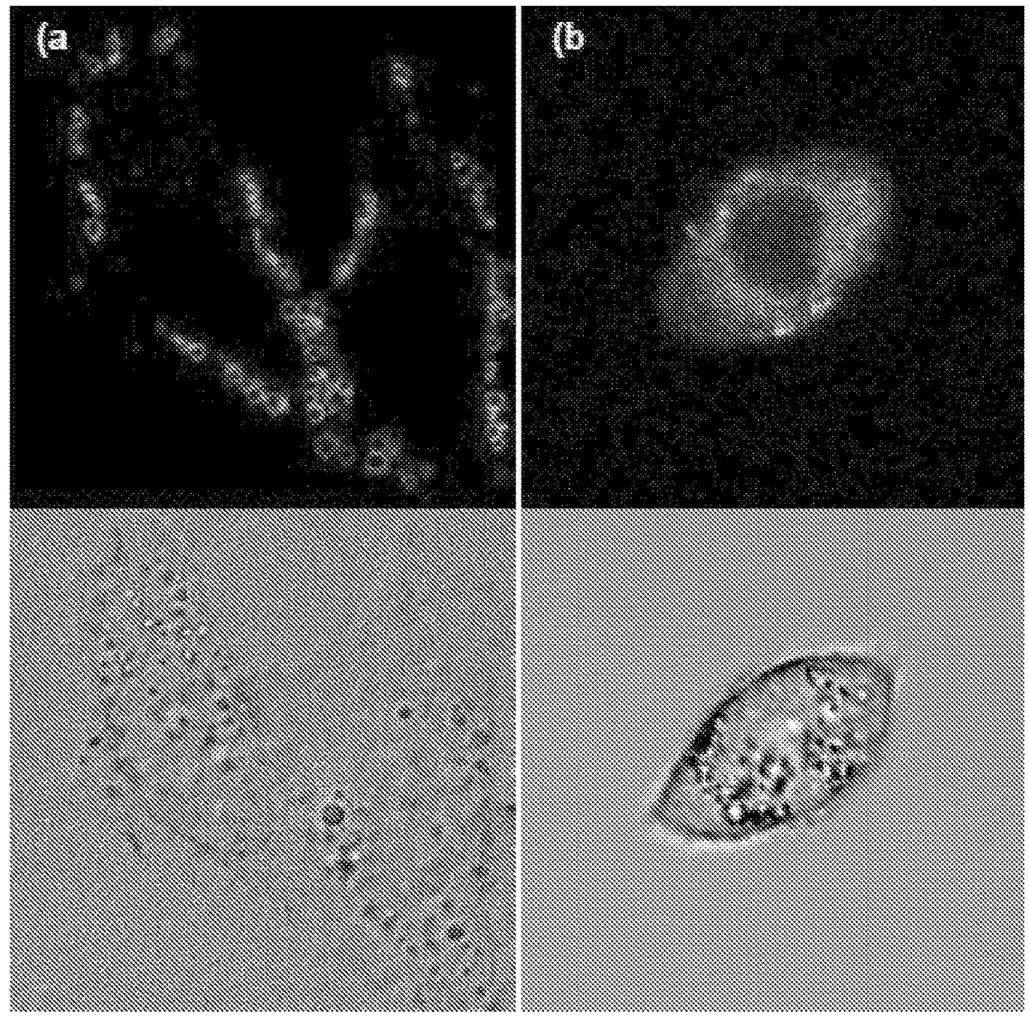

FIG. 10 provides confocal images at 488 nm channel of TQ Green (acid form, FIG. 10A), and TQ Green-AM (ester form, FIG. 10B) interacting with cells. Most of the acid form probe molecules were trapped in the membrane. However, the AM-ester form was able to penetrate through cell the membrane and stay in the cytosol after hydrolysis.

Figure 11:
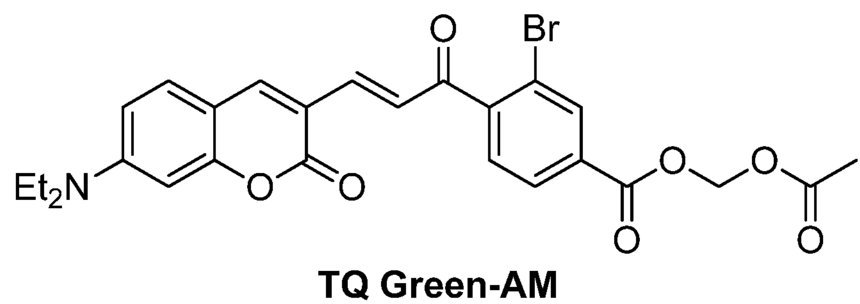

FIG. 11 shows a structure of TQ Green-AM.

Figure 12:
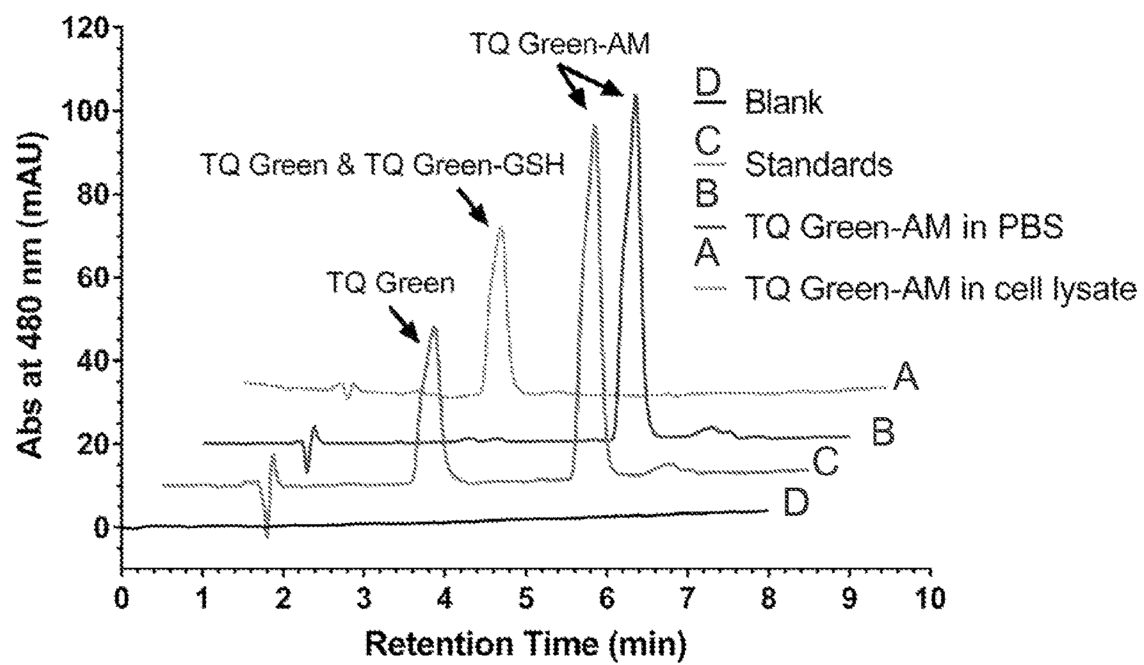

FIG. 12 provides data relating to the regeneration of TQ Green from TQ Green-AM in an intracellular environment.

Figure 13:
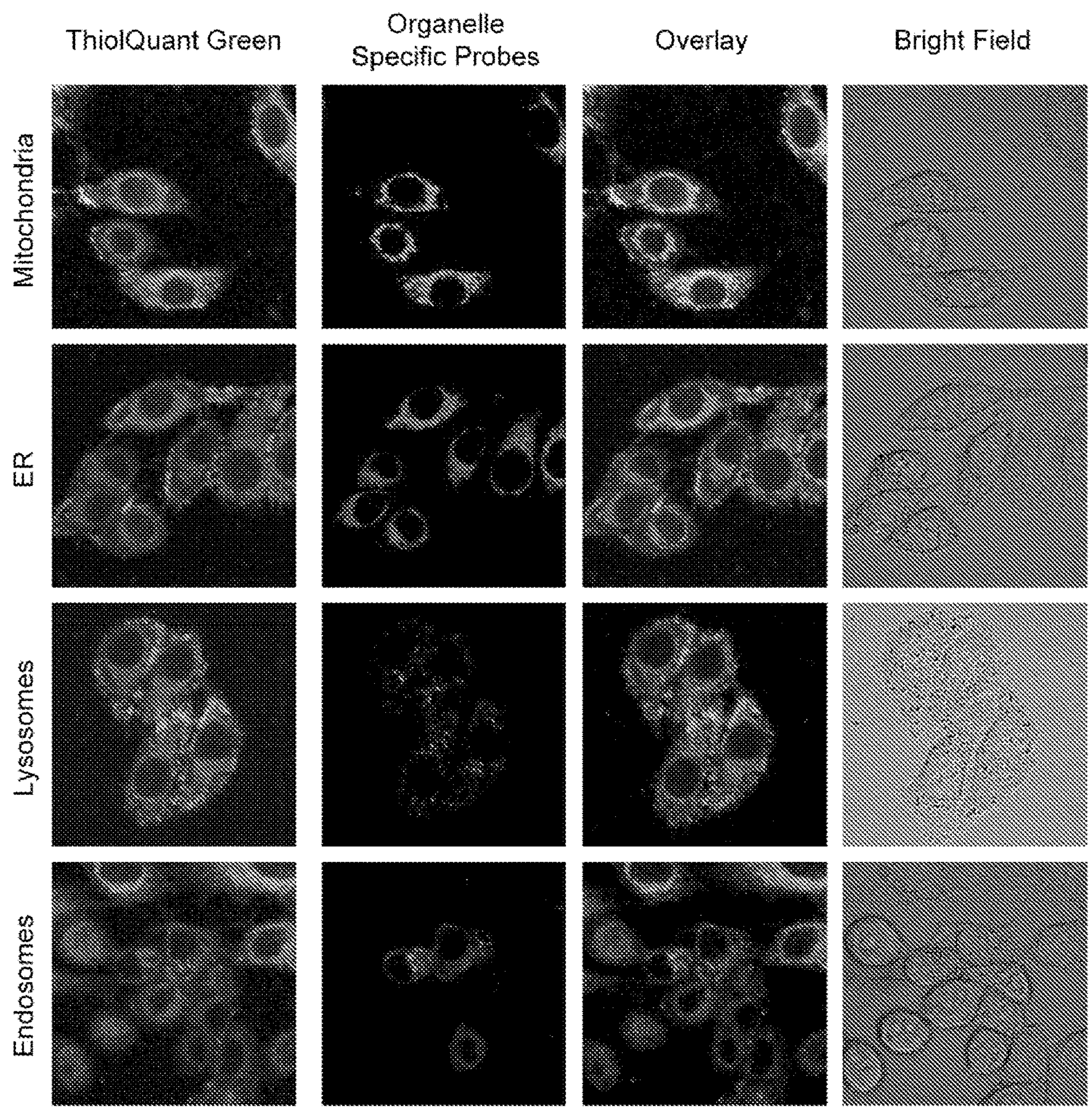

FIG. 13 shows images relating to the subcellular distribution of TQ Green.

Figure 14:
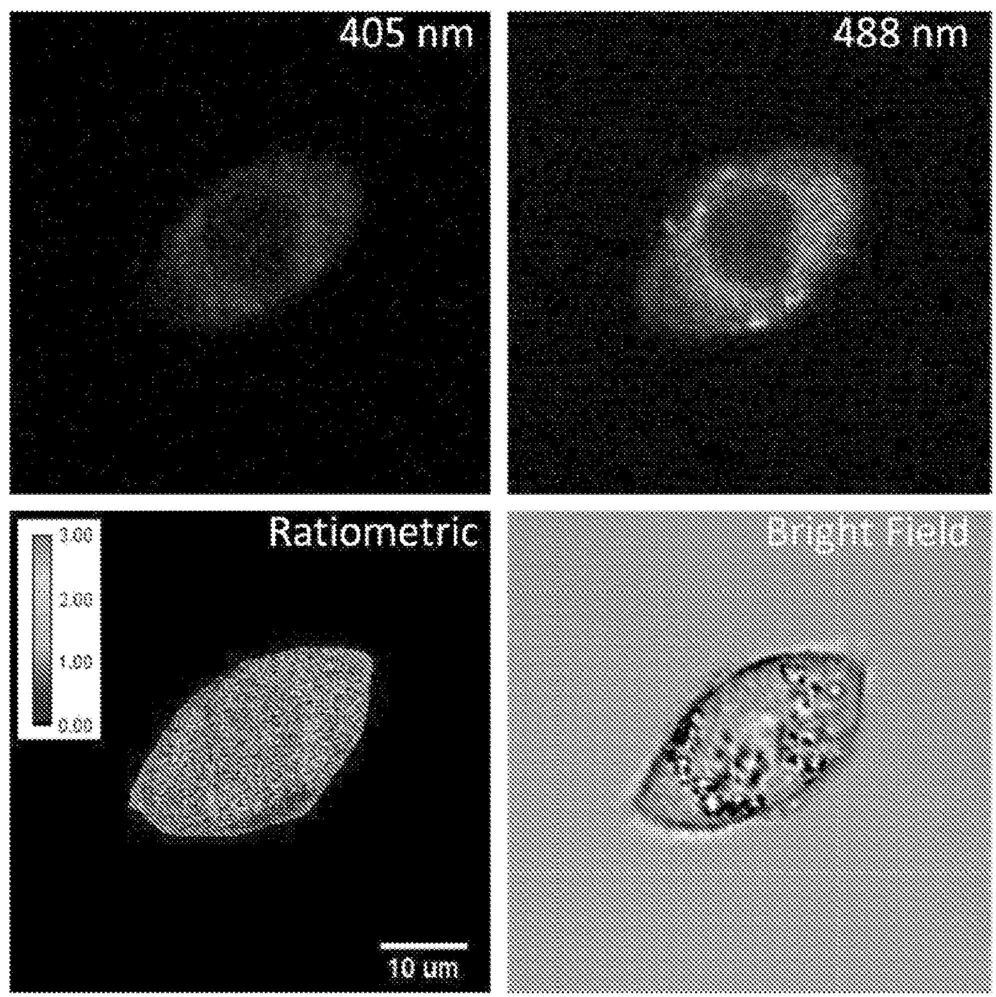
Figure 14:
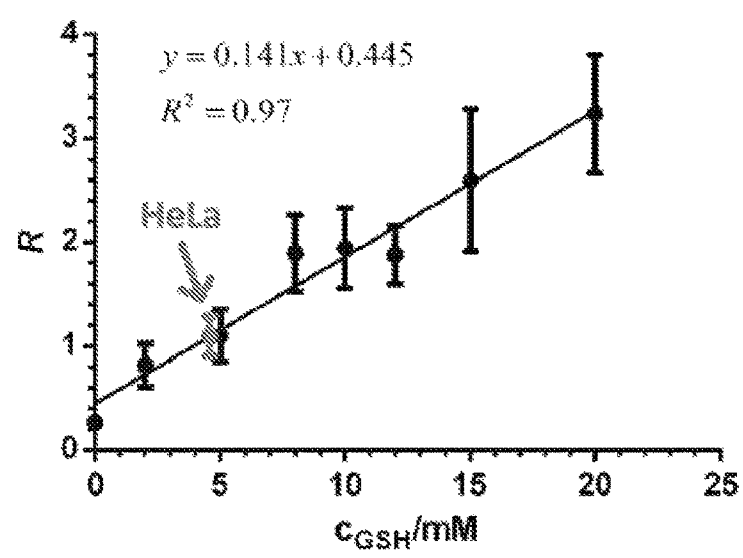

FIG. 14 shows the measurements of GSH levels in HeLa cells based on ratiometric fluorescence imaging. FIG. 14A shows representative images of HeLa cells treated with TQ Green-AM. The ratiometric image represents the distribution of GSH levels (unit: mM). FIG. 14B shows the standard curve of R, the fluorescence intensity ratio between 405 nm and 488 nm excitation, as a function of GSH concentration produced using the same instrument setting as the live cell imaging experiment. The data point in red represents the GSH concentration in HeLa cells based on statistical analyses of more than 40 cells. Error bars represent standard deviations.

Figure 15:
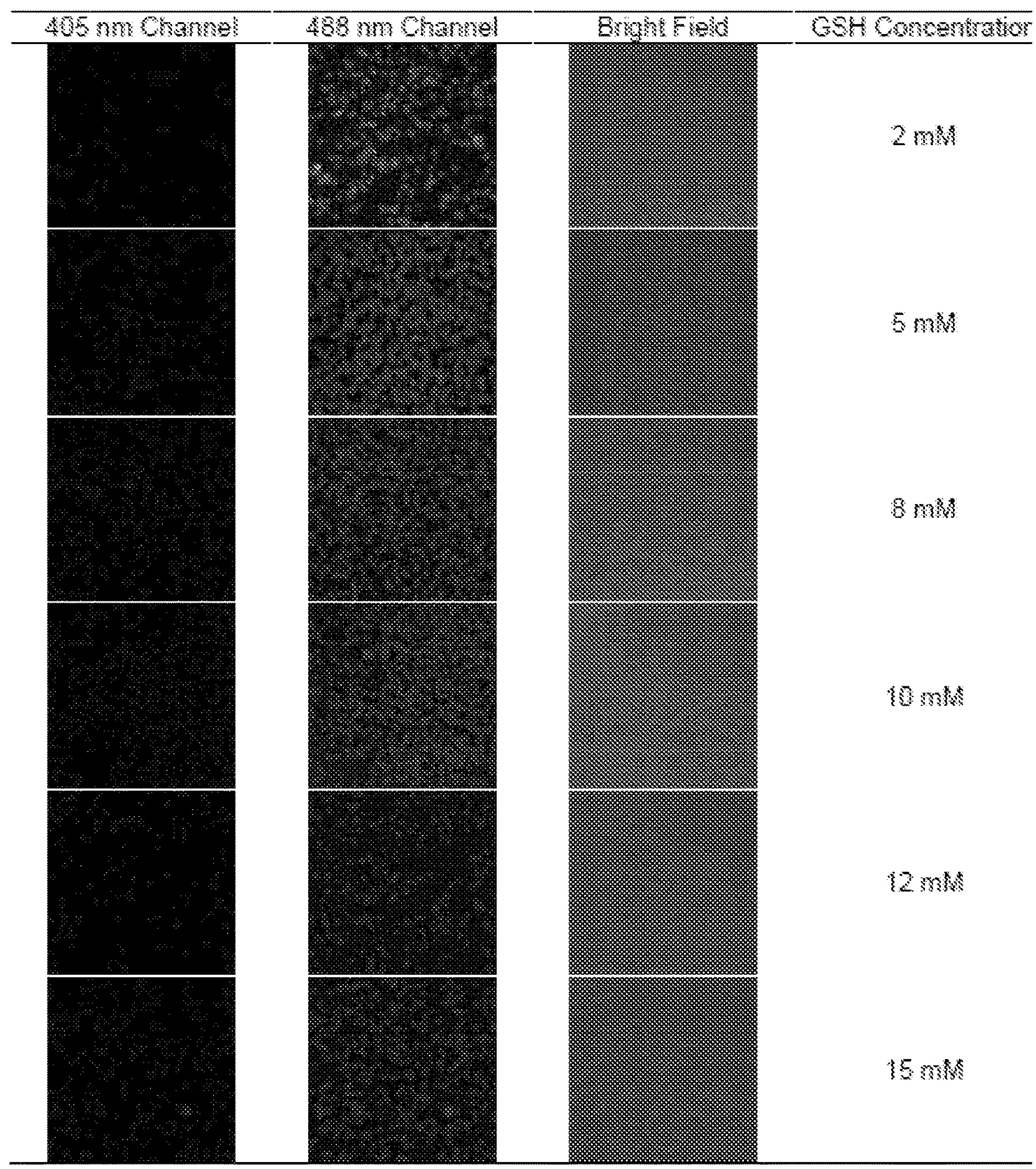

FIG. 15 provides confocal fluorescent images of TQ Green absorbed on polystyrene beads in various concentrations of GSH solution.

Figure 16:
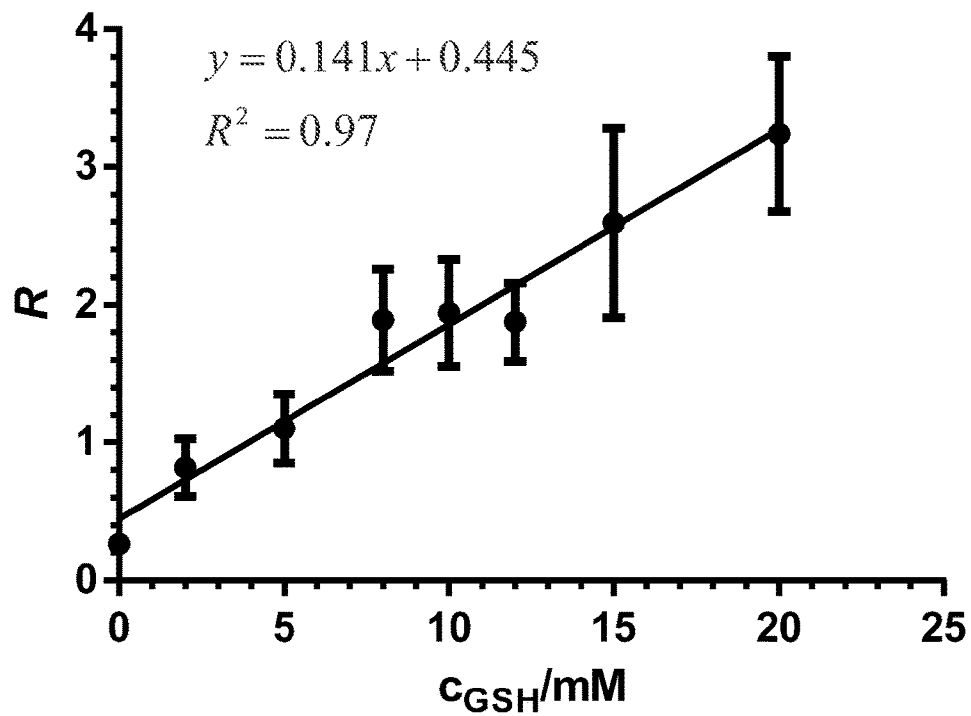

FIG. 16 provides a calibration curve for confocal microscope based on fluorescent images from FIG. 15. Intensity average from both channels (405 nm and 488 nm excitation) was used for calculation.

Figure 17:
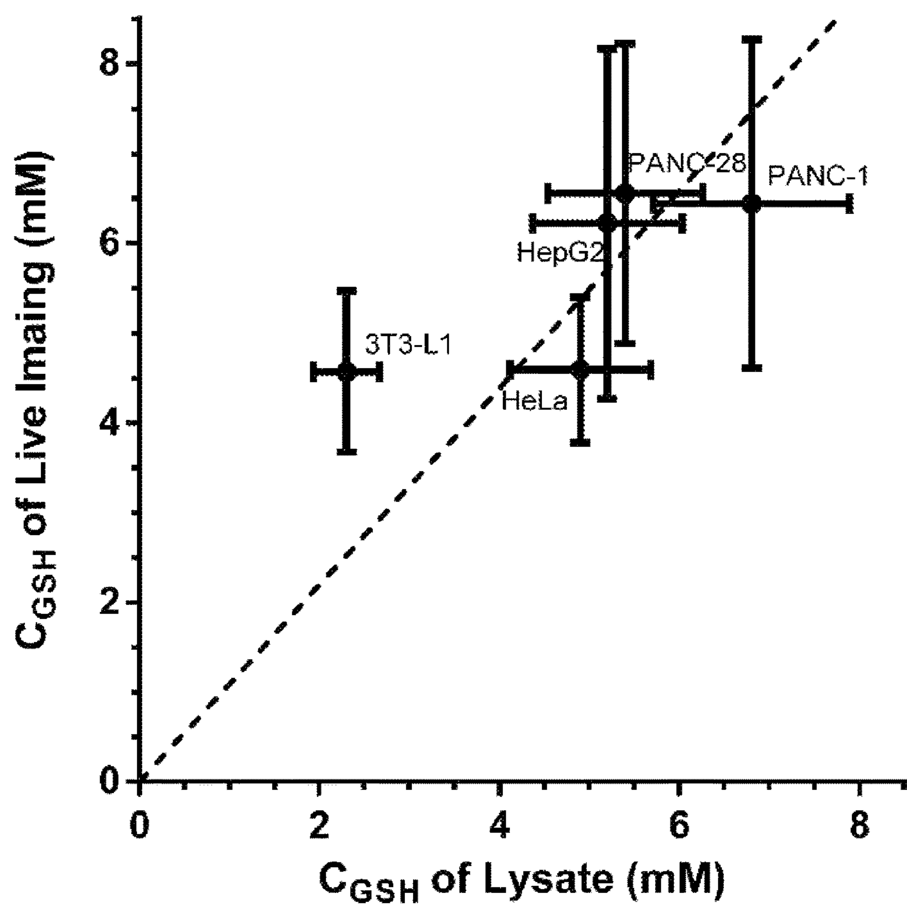

FIG. 17 shows correlation between the GSH concentrations measured in live cells and in lysates. Y-axis represents concentrations derived from live imaging, while x-axis represents concentrations determined using cell lysate. All imaging results are from statistical analysis of more than 40 cells. All assay results are from more than 3 replicates under the same conditions. Error bars represent standard deviations. The slope of the correlation line (the dash line) is 1.1.

Figure 18:
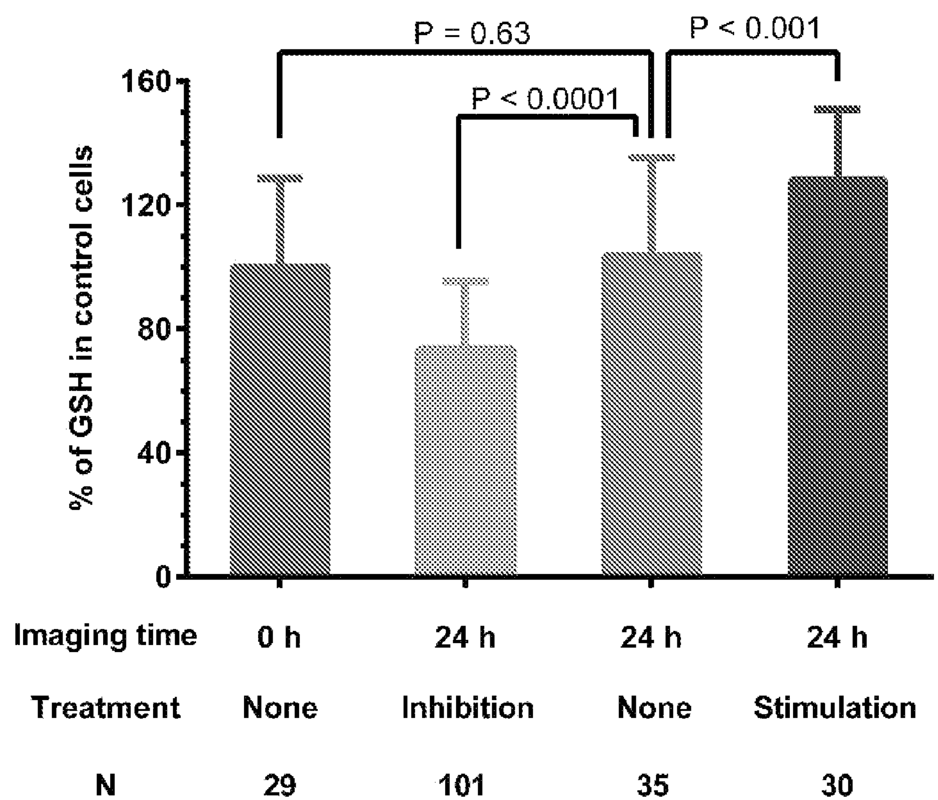

FIG. 18 shows the detection of GSH level changes in PANC-1 cells using TQ Green live imaging. PANC-1 cells were treated with diethyl maleate (50 μM) for 24 hours and 2 hours to inhibit and stimulate GSH levels, respectively. All the cells were imaged 24 hours after starting the experiment. Results are statistical analyses of more than 25 cells. P values shown are based on unpaired student t-tests. Error bars represent standard deviations.

Figure 19:
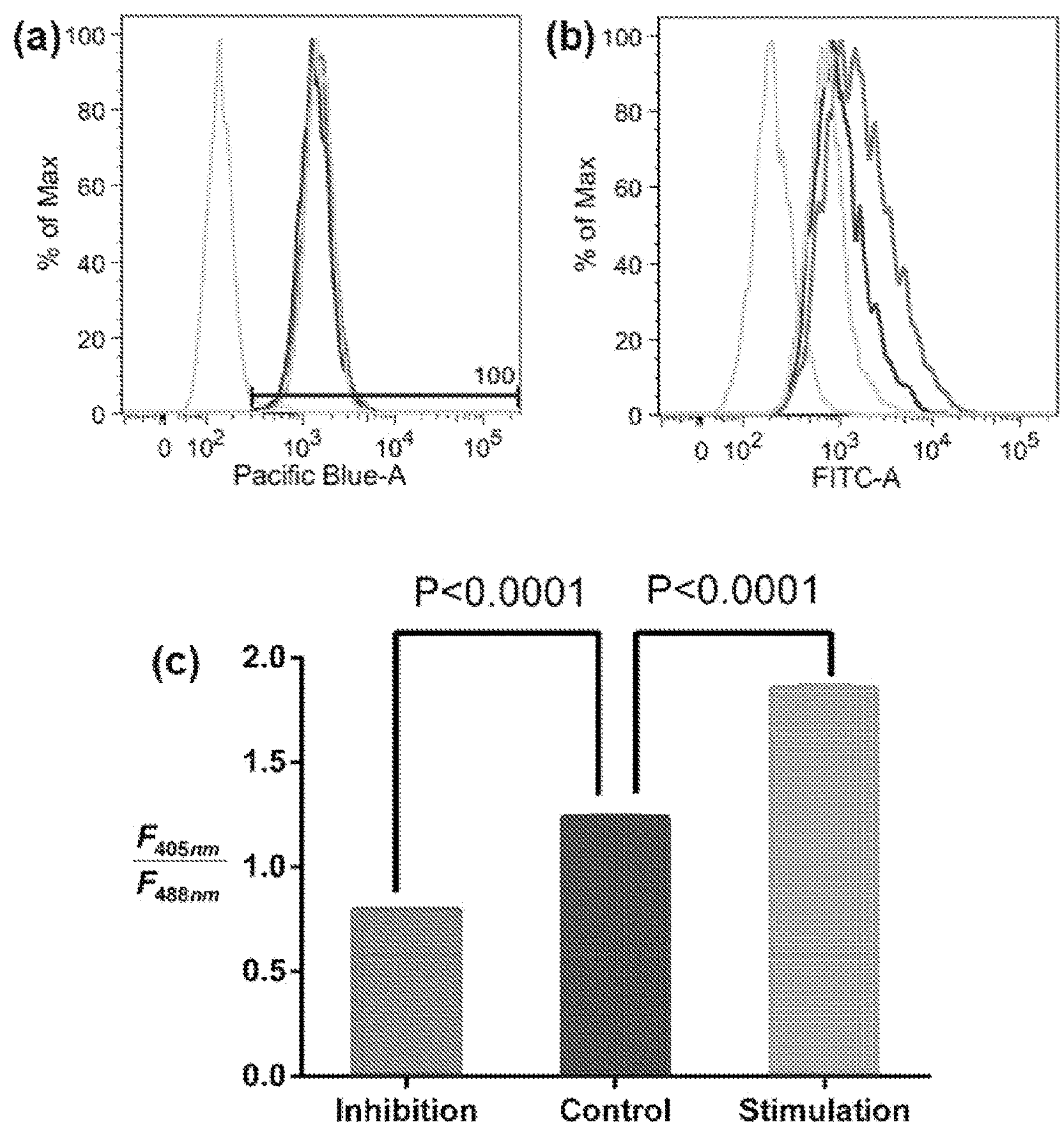

FIG. 19 provides data relating to the quantification of GSH levels using fluorescence activated cell sorting (FACS). PANC-1 cells were treated with diethyl maleate (50 μM) for 24 hours and 2 hours to inhibit and stimulate GSH levels, respectively. The GSH levels of the cells were measured 24 hours after starting the experiment using FACS. FIGS. 19A-B show histograms of the 405 nm (blue) and 488 nm (green) channels. FIG. 19C shows the fluorescence intensity ratios of 405 nm and 488 nm as a function of treatment conditions. Results are statistical analyses of more than 4000 cells. P values shown are based on unpaired student t-tests. Error bars, representing SEM, are too small to show clearly.

Figure 20:
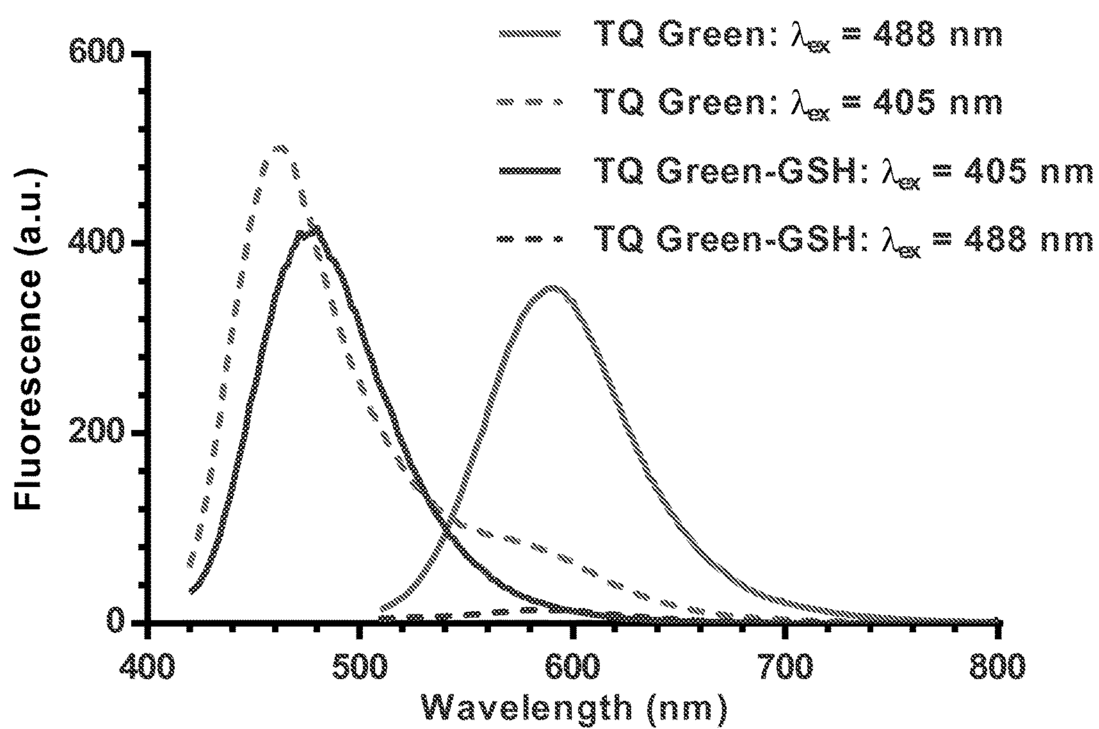

FIG. 20 shows fluorescent spectra of TQ Green and TQ Green-GSH with excitation wavelengths at 405 nm and 488 nm. The fluorescent signal with 405 nm excitation does not have significant changes upon addition of GSH, due to the coincidence that the loss of TQ Green fluorescence is compensated by the gain of TQ Green-GSH fluorescence. The fluorescent signal with 488 nm excitation changes dramatically. Accordingly, the ratio between the signals from the two channels changes significantly as well.

Figure 21:
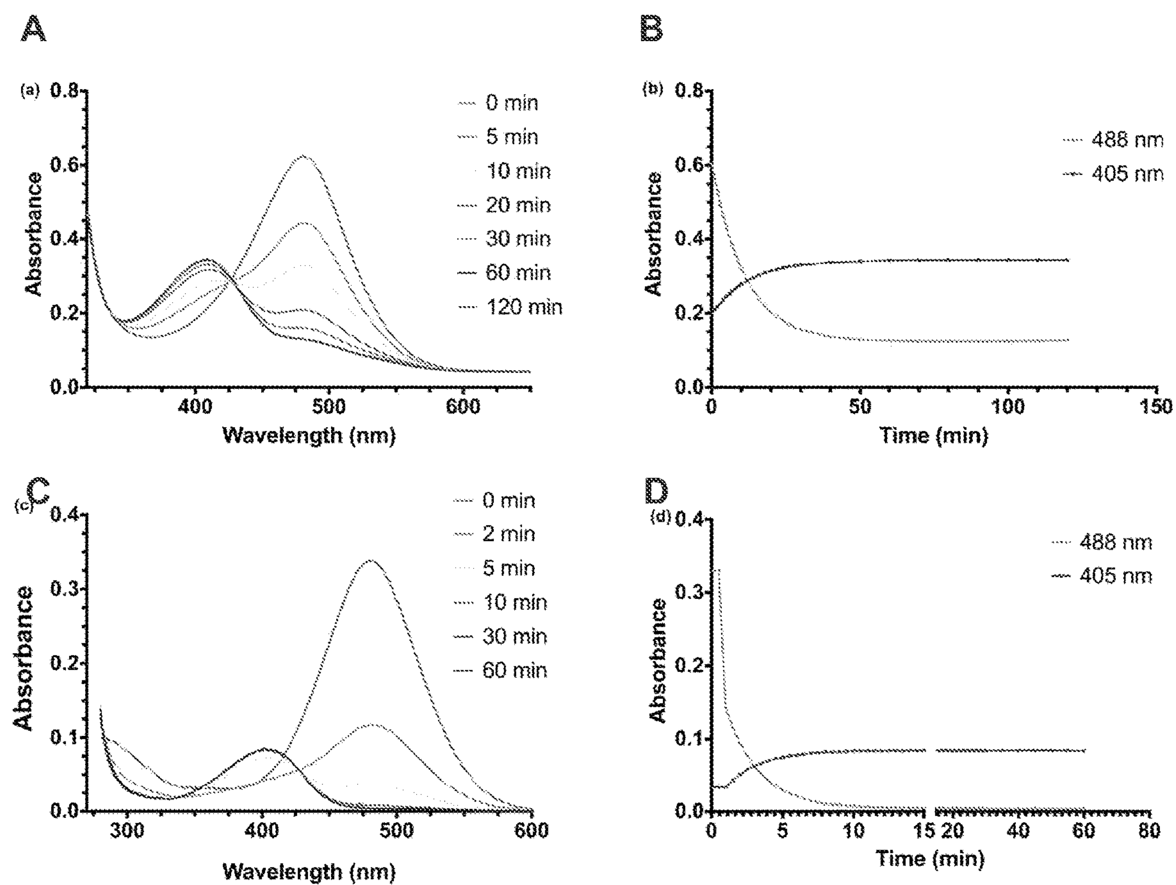

FIG. 21 shows the reaction kinetics of various probes. FIGS. 21A-B show the reaction kinetics of TQ Green. Time-dependent spectra and kinetics were shown for TQ Green (16 μM) reacting with 10 mM of GSH in PBS. At room temperature, the reaction takes ~30 minutes to reach 95% of conversion. FIGS. 21B-D show the reaction kinetics of probe 3a. Time-dependent spectra and kinetics were shown for probe 3a (10 μM) reacting with 10 mM of GSH in PBS. At room temperature, the reaction takes ~6 minutes to reach 95% of conversion.

Figure 22:
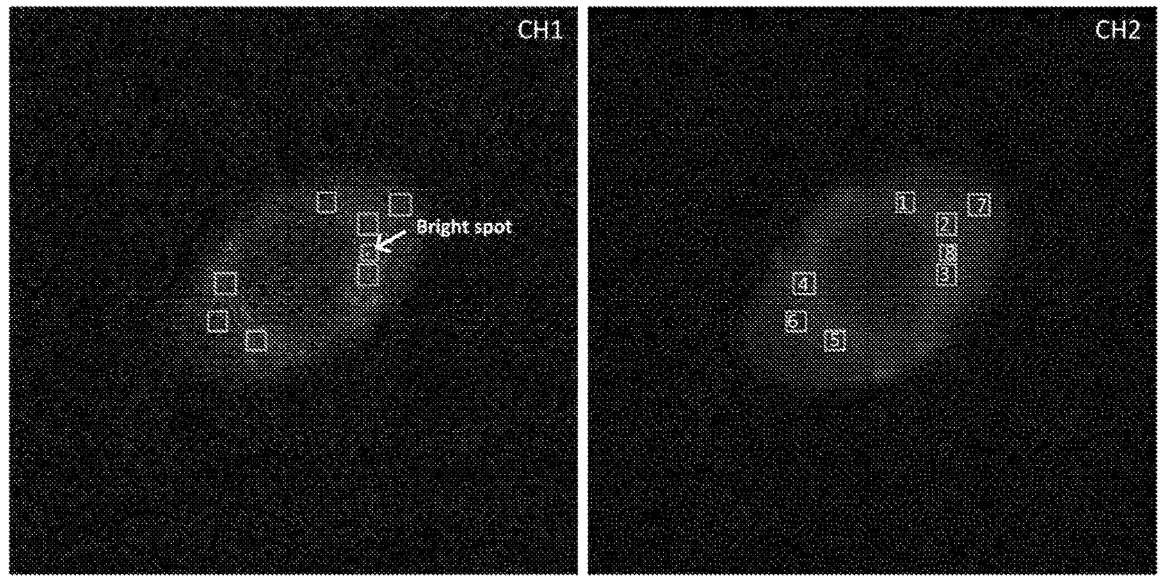

FIG. 22 shows various data and images relating to image processing and statistical analyses.

Figure 23:
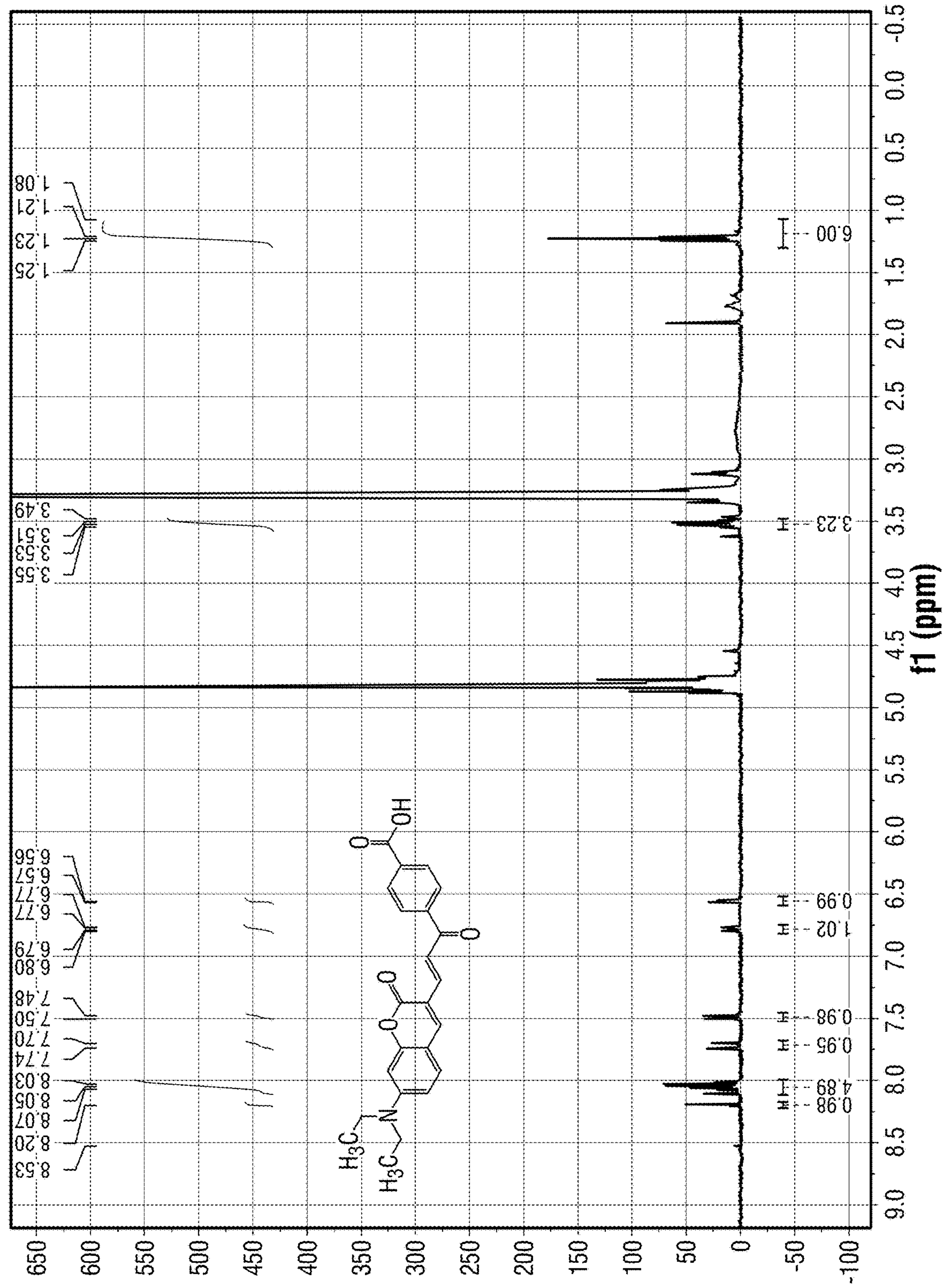

FIG. 23 provides a $^1$H-NMR (400 MHz, $CD_3OD$) spectrum of compound 3a.

Figure 24:
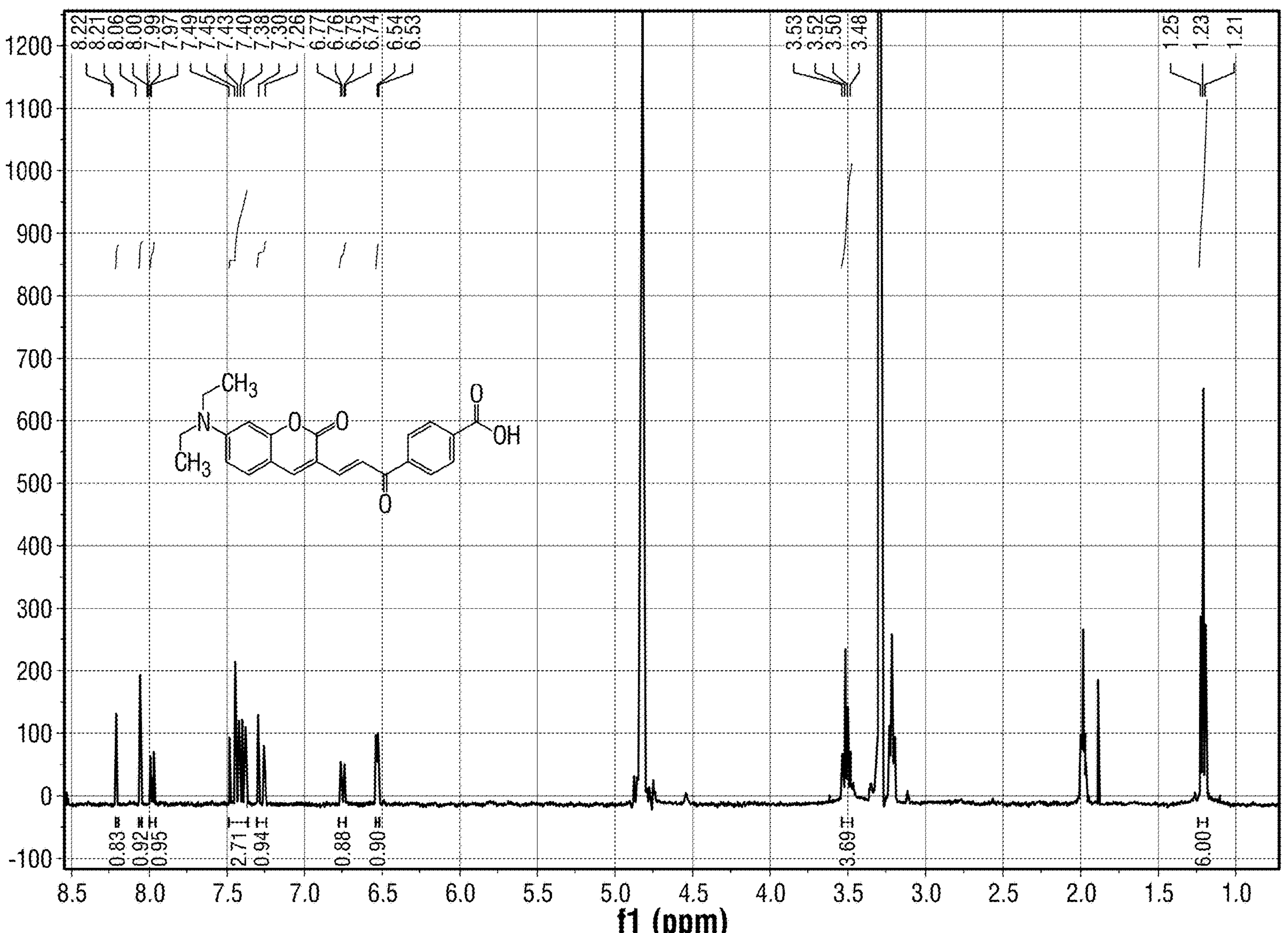

FIG. 24 provides a $^1$H-NMR (400 MHz, $CD_3OD$) spectrum of ThiolQuant Green.

Figure 25:
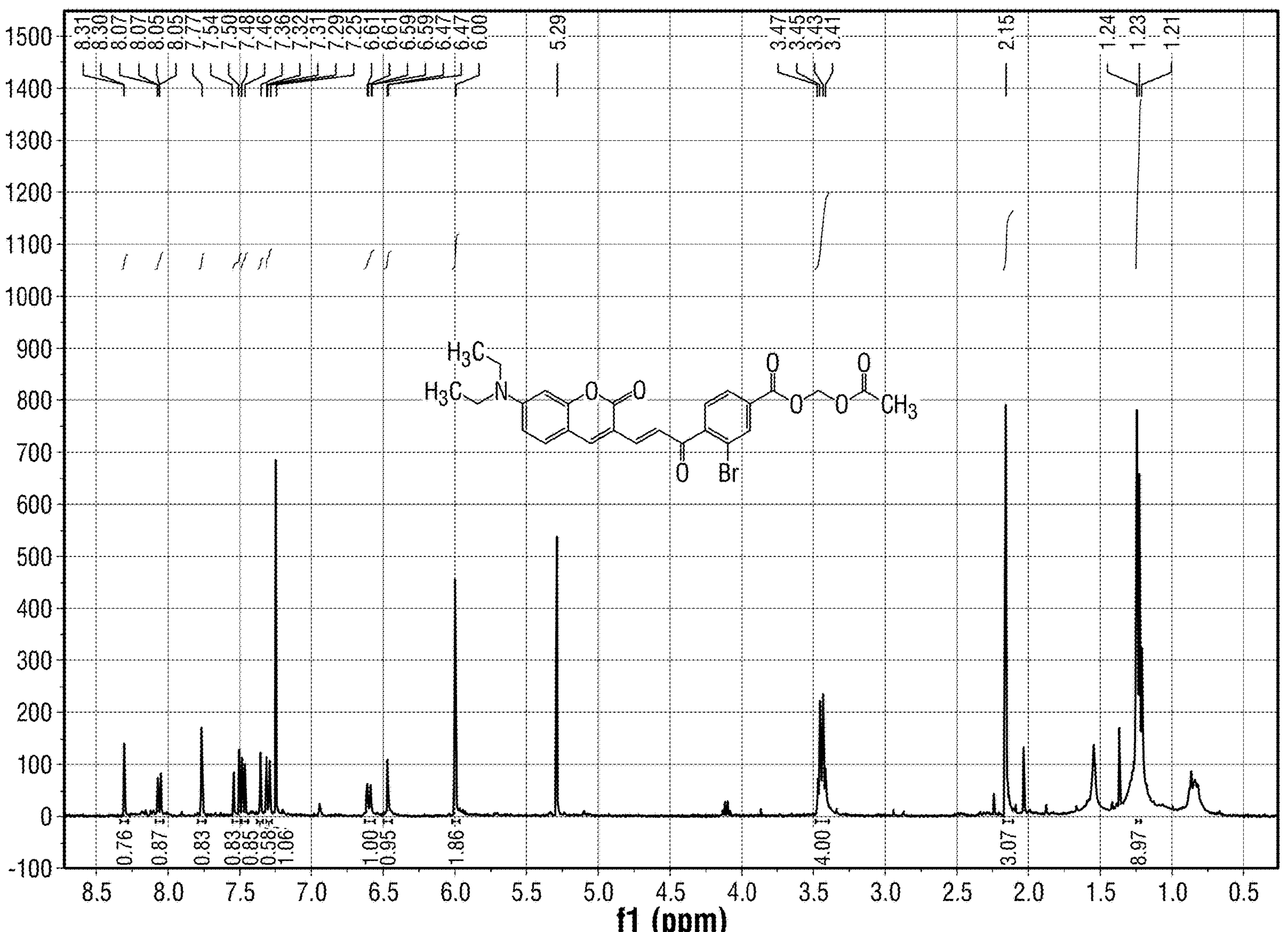

FIG. 25 provides a $^1$H-NMR (400 MHz, $CDCl_3$) spectrum of ThiolQuant Green-AM.

Figure 26:
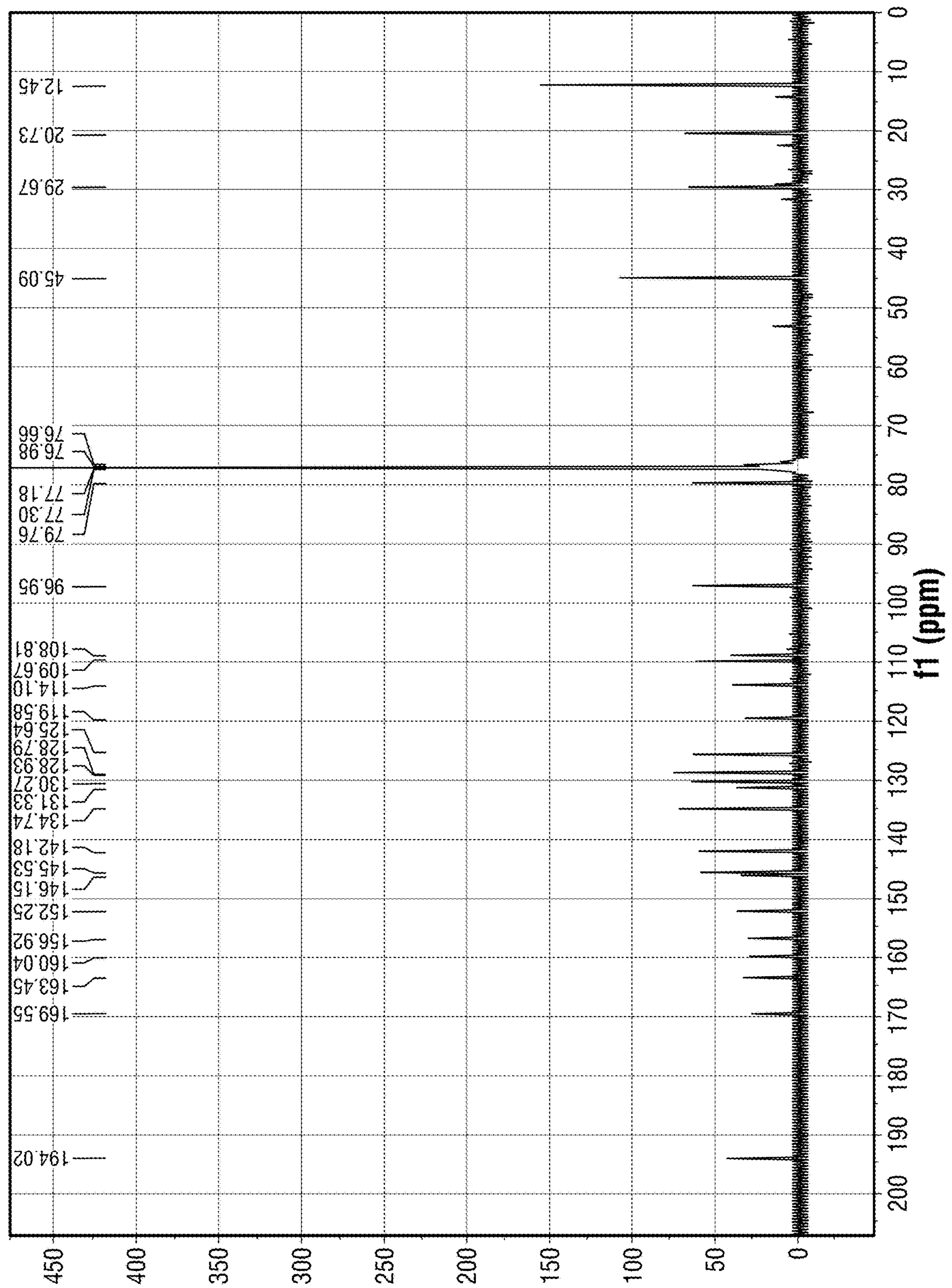

FIG. 26 provides a $^{13}$C-NMR (100 MHz, $CDCl_3$) spectrum of ThiolQuant Green-AM.

Figure 27:
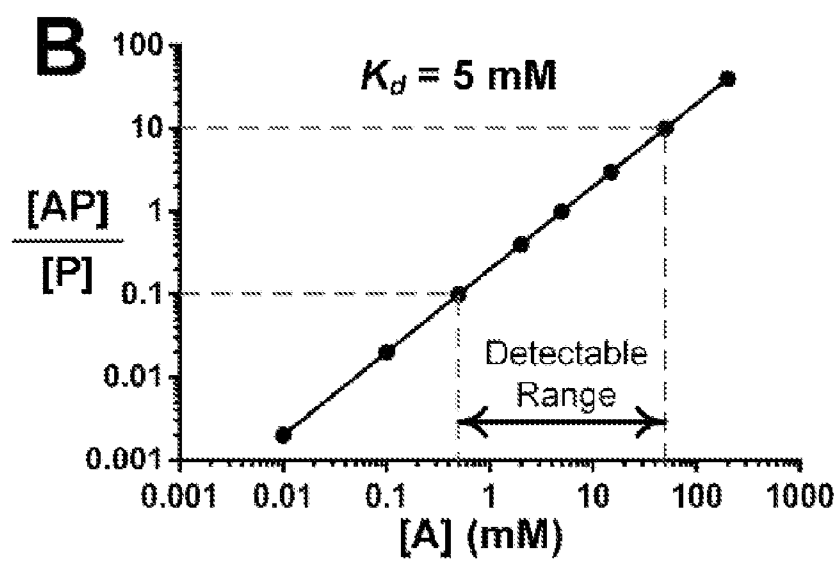

FIG. 27 provides an illustration of the detection range of equilibrium based ratiometric probes. FIG. 27A provides a graph illustrating the relationship between Analyte (A), Probe (P), and Analyte-Probe adduct (AP). $K_d$ is the dissociation equilibrium constant. FIG. 27B illustrates the detection range of the analyte (assuming $K_d$=5 mM and at least 10% of AP or P remaining to be detected). The lower (red) and upper (blue) limit of detection are labeled with dash lines. The detection range in this example is 0.5-50 mM.

Figure 28:
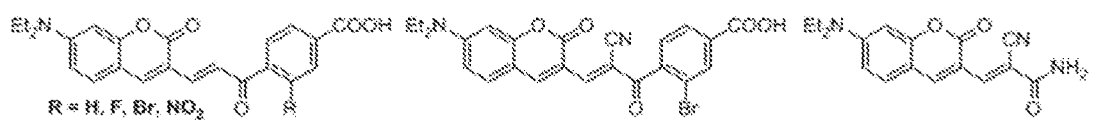

FIG. 28 provides various data and structures relating to the characterization of GSH probes. FIG. 28A provides structures of GSH probes. FIG. 28B provides a comparison of experimental $\Delta G^o$ with calculated $\Delta G_{calc}$ between MeSH and GSH probe library. FIG. 28C provides a comparison of experimental kinetic parameters with calculated $\Delta G'_{calc}$ between $MeS^-$ and GSH probe libraries. All the experimental values were measured for the reactions between GSH probe library and GSH. Forward $t_{1/2}$: half-life measured in 10 mM GSH solution. $k_f$ and $k_r$ are rate constants for forward and reverse reactions. All the computations were performed using M06-2X/6-31+G(d) level of theory in water using an SMD solvation model. To simplify calculations, MeSH was substituted for GSH.

Figure 29:
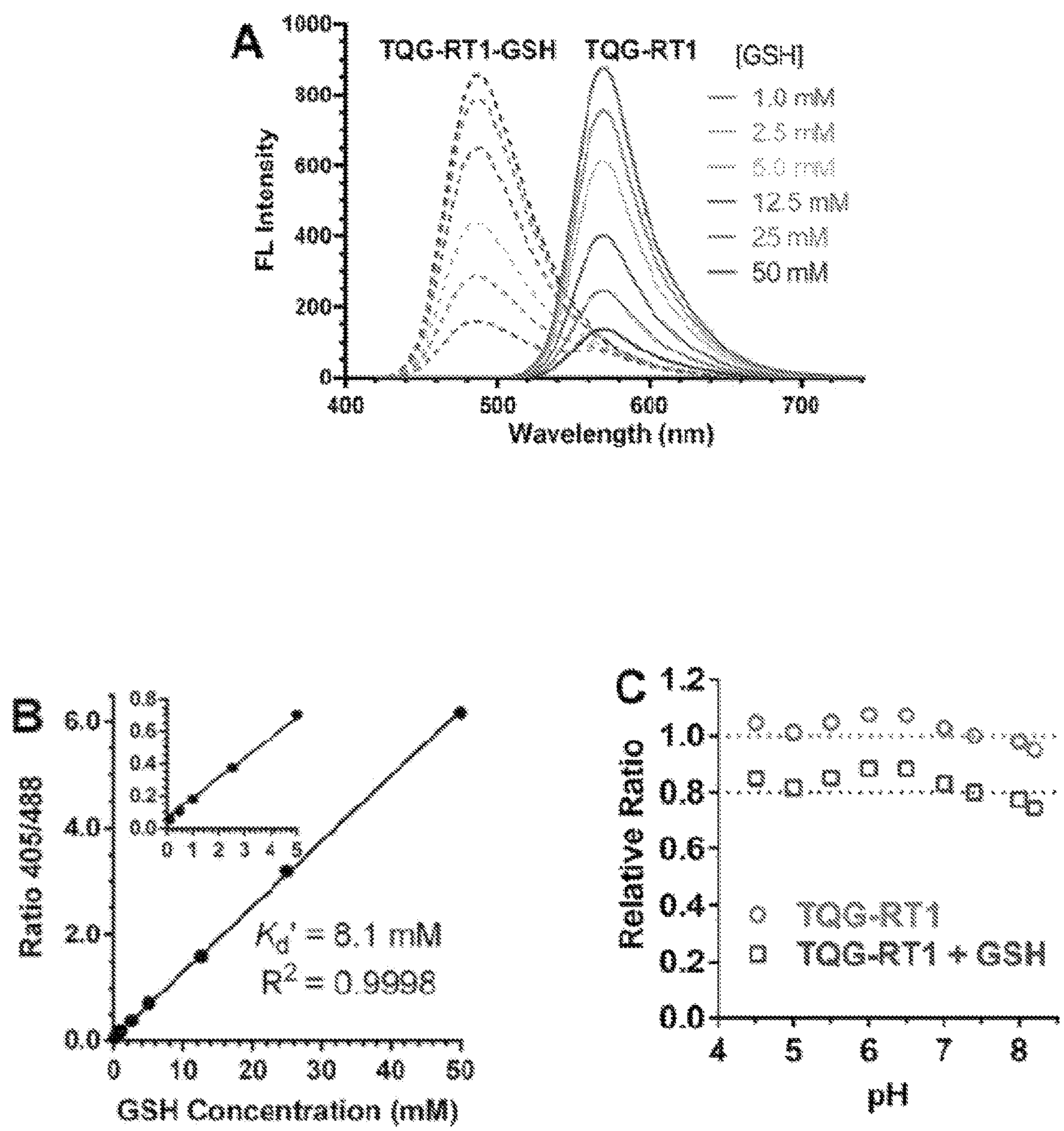
Figure 29:
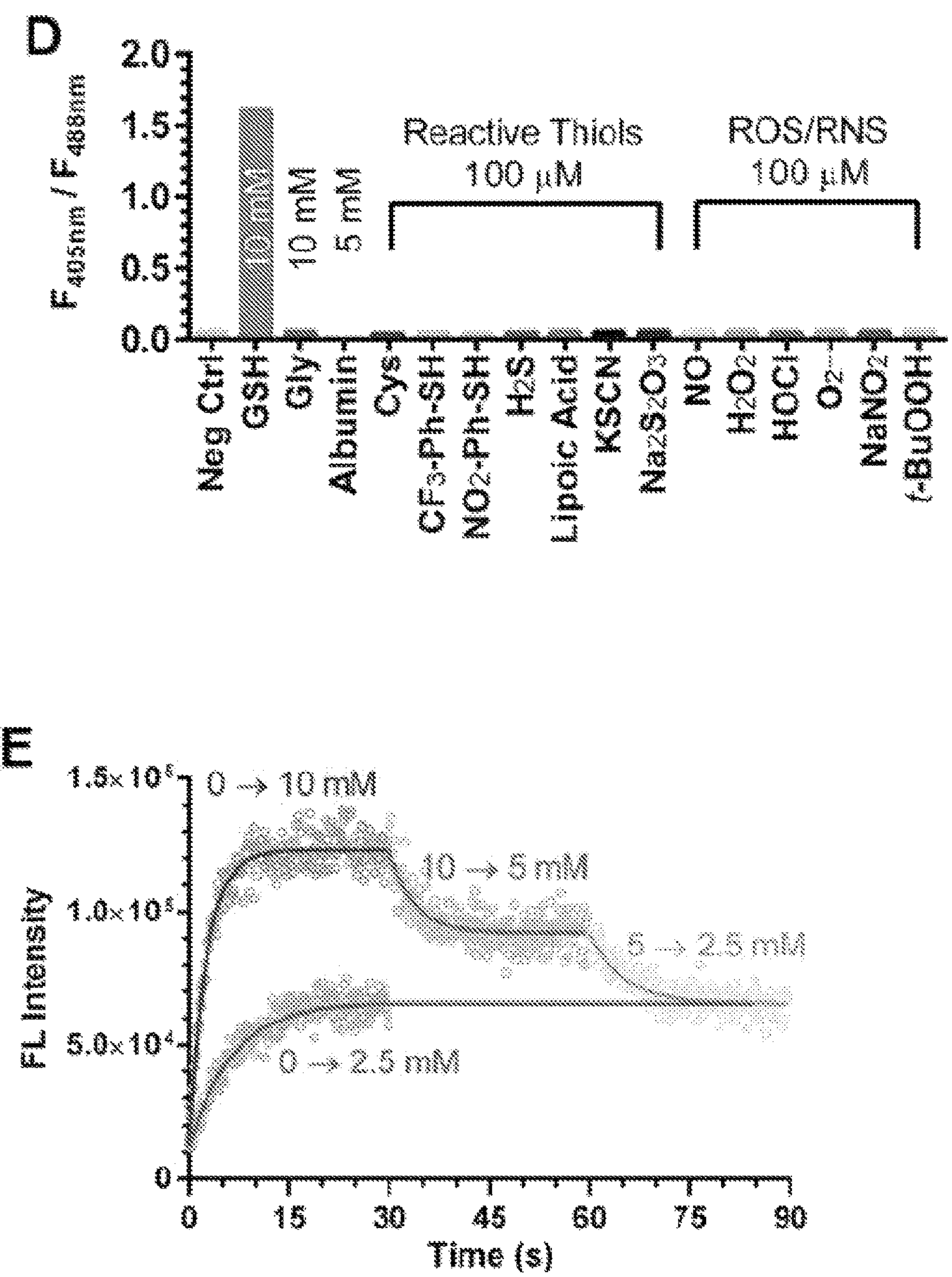
Figure 30:
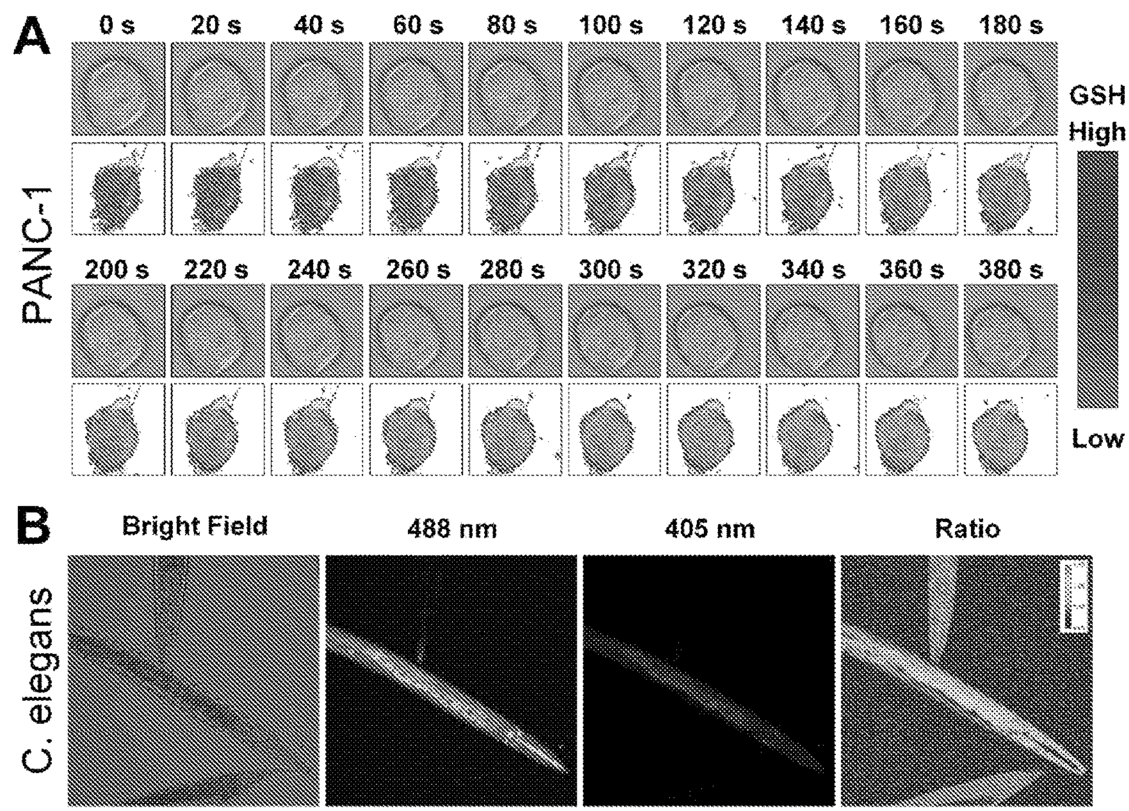

FIG. 29 provides data relating to the characterization of TQG-RT1. FIG. 29A provides data relating to the fluorescence of TQG-RT1 ($\lambda_{ex}$=488 nm) and TQG-RT1-GSH ($\lambda_{ex}$=405 nm) in the presence of different concentrations of GSH. FIG. 29B provides a linear relationship ($R^2$=0.9998) between the ratio of fluorescence intensities with 405 and 488 nm excitations and GSH concentration. Insert is a zoom-in of the low concentration region. FIG. 29C provides ratios of TQG-RT1 in the absence (red circles) and presence (blue squares) of 5 mM GSH in buffers at different pHs. The ratio (F405/488) at pH 7.4 was defined as 1. The blue (square) data points were shifted down by 0.2 units for clarity. FIG. 29D shows that TQG-RT1 only responds to 10 mM GSH, but not other reactive thiols and ROS/RNS (100 μM). FIG. 29E shows forward and reverse reaction kinetics between TQG-RT1 and GSH at pH 7.4. The kinetics of the formation of TQG-RT1-GSH was monitored ($\lambda_{ex}$=405 nm) using a stopped-flow instrument. The forward reaction kinetics was measured by mixing TQG-RT1 solution (10 μM) with an equal volume of 20 mM (blue) and 5 mM (purple) GSH solutions. The reverse reaction kinetics was measured by mixing a pre-equilibrated solution of TQG-RT1 and GSH (20 mM, red; 10 mM, green) with an equal volume of PBS. The numbers indicate the changes of GSH concentrations. The red and green traces were offset by 30 and 60 seconds for clarity. All the equilibria were re-established within 20 seconds FIG. 30 shows real-time GSH imaging using TQG-RT1. FIG. 30A shows a time-lapsed GSH imaging of PANC-1 cells, a pancreatic cancer cell line, upon exogenous $H_2O_2$ (200 μM) treatment at time zero. Bright field and ratiometric images are shown. FIG. 30B shows that *C. elegans* were incubated with TQG-RT1 (1 μM) for 2 hours and imaged. The middle worm has substantial probe uptake, which gives satisfactory ratiometric imaging.

Figure 31:
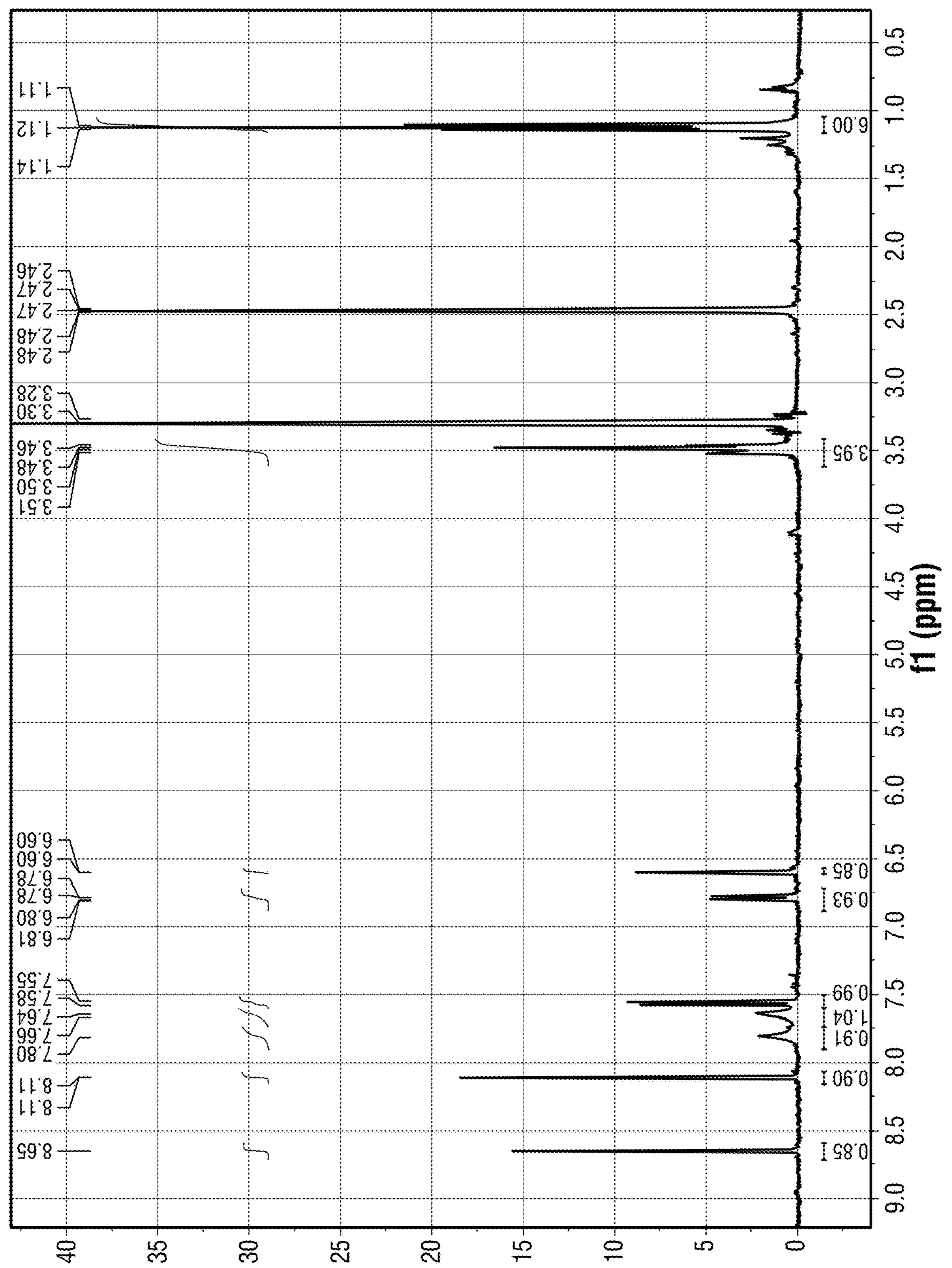

FIG. 31 is a $^1$H-NMR of compound 3 (400 MHz, d6-DMSO), as illustrated in Example 2.8.

Figure 32:
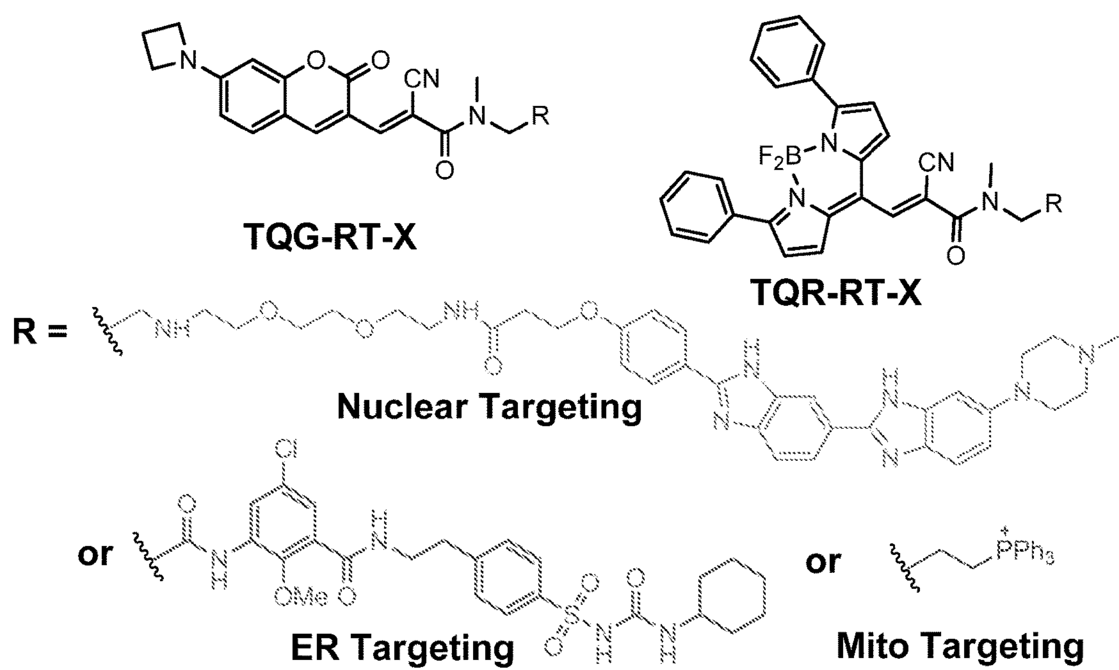

FIG. 32 provides structures of organelle specific GSH probes with Hoechst nuclear targeting, glibenchlamide ER targeting, or TPP mitochondria targeting.

Figure 33:
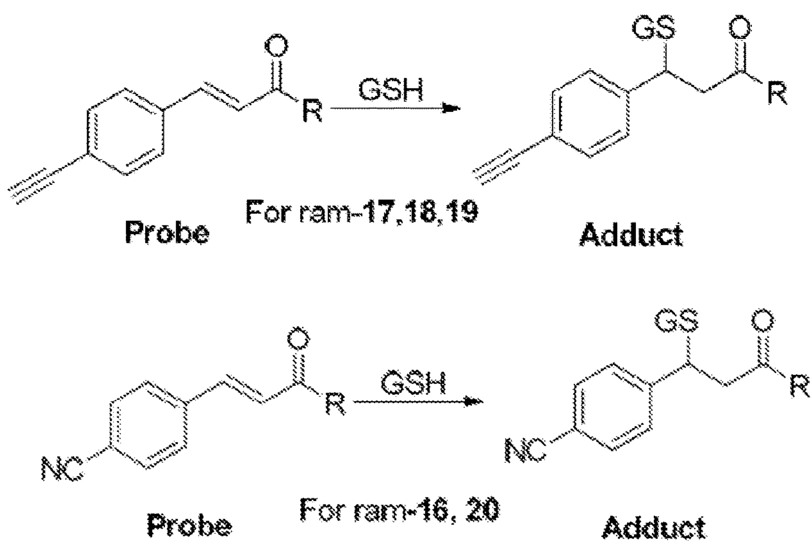
Figure 33:
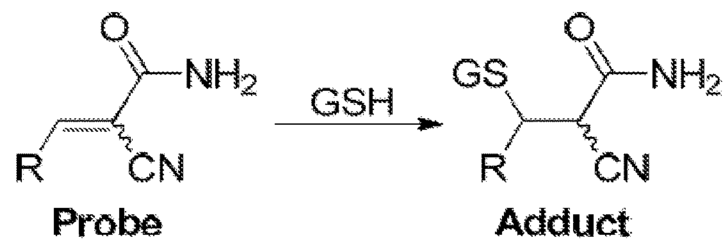

FIG. 33 provides various reaction schemes (FIGS. 33A and 33C) and data (FIGS. 33B and 33D) that demonstrate the use of Raman spectroscopy to detect thiols.

Figure 34:
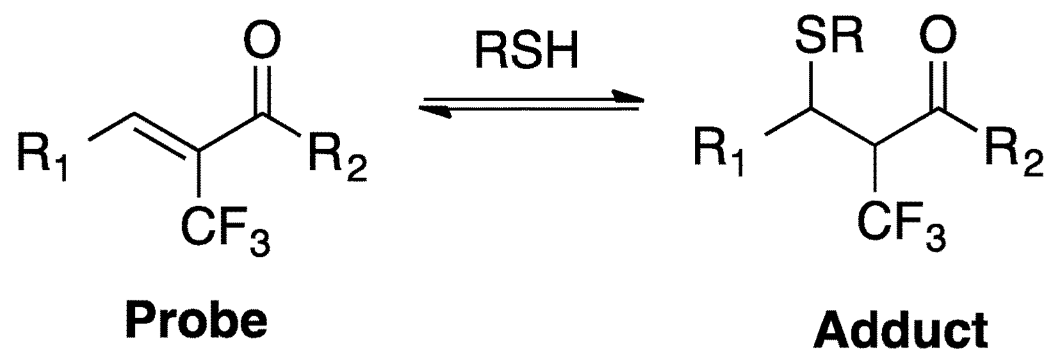

FIG. 34 provides a reaction scheme where $CF_3$ groups in a probe molecule and a thiol-probe adduct have different chemical shifts under magnetic resonance imaging (MRI).

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Thiols play important roles in many physiological processes. For instance, glutathione (GSH) is the most abundant non-protein thiol in mammalian cells and plays an important role in maintaining redox homeostasis inside cells. Variations in intracellular GSH concentration have been linked to many pathological processes, including cancer, aging, and diabetes. In order to understand the influence of GSH in these processes, it is desirable to precisely measure the GSH concentration in live cells.

Currently, there are no methods available to quantitatively assess the GSH concentration in live cells. Although many GSH responsive chromogenic and fluorogenic reagents have been developed, quantification using these reagents can only be performed on cell lysates. Additionally, despite the fact that a myriad of GSH fluorescent probes are reported for live cell imaging, none of these probes can provide meaningful quantitation of intracellular GSH concentrations.

Furthermore, current approaches are incapable of providing information about the dynamics of GSH and GSSH concentration change and crosstalk between GSH concentration differential in different cellular compartments. For instance, redox-sensitive green fluorescent protein (roGFP) remains one of the most popular GSH probes for live cell imaging. However, roGFP does not provide absolute GSH concentrations. Rather, roGFP can only monitor the ratio of GSH to the oxidized form GSSG.

Furthermore, the conventional roGFPs lack specificity and respond slowly to changes in redox potential. Therefore, the most widely used probe for studying redox biology is the fusion of human glutaredoxin-1 (Grx1) to roGFP2. However, it is well-known that Grx1 is a key player in maintaining redox homeostasis. Therefore, the main disadvantage of roGFP2-Grx1 as a redox probe is that overexpression of this protein may change the redox status of the probed cells.

The aforementioned limitations also apply to the quantification of other thiols in live cells. Therefore, a need exists for more effective probes for the detection and quantification of various thiols.

In some embodiments, the present disclosure pertains to methods of detecting a thiol in an environment by utilizing probe molecules that include at least a marker and a thiol responsive group. In some embodiments illustrated in FIG. 1, the methods of the present disclosure include exposing the environment to the probe molecule (step 10) to result in a reversible reaction between the thiol in the environment and the thiol responsive group of the probe molecule, and thereby form a probe-thiol adduct (step 12). In some embodiments, the reversible reaction causes a ratiometric change in a spectrometric property of the probe molecule and the probe-thiol adduct (step 14). In some embodiments, the methods of the present disclosure also include a step of correlating the ratiometric change in the spectrometric property of the probe molecule and the probe-thiol adduct to the presence of thiol in the environment (step 16). In some embodiments, the correlating includes visual detection (step 18). In some embodiments, the correlating includes thiol quantification (step 20). In some embodiments, the detection method occurs in real-time.

Additional embodiments of the present disclosure pertain to the probe molecules that are used for detecting a thiol in an environment. As set forth in more detail herein, various probe molecules may be utilized to detect and quantify various types of thiols in various environments by various methods.

Environments

The methods and probe molecules of the present disclosure may be utilized to detect thiols in various environments. In some embodiments, the environment is an in vitro environment. In some embodiments, the environment is an in vivo environment. In some embodiments, the environment includes, without limitation, liquids, fluids, organic solvents, thiol-containing solutions, plasma, extracellular fluids, cellular extracts, cells, cytosols, organelles, and combinations thereof.

In some embodiments, the environment includes cells. In some embodiments, the cells are at least part of a tissue, an organ, or an organism. In some embodiments, the cells are living cells that are part of a tissue. In some embodiments, the cells are living cells that are part of an animal. In some embodiments, the cells are grown in vitro.

In some embodiments, the environment is a specific part of a cell. For instance, in some embodiments, the environment is a cytosol of a cell. In some embodiments, the environment is an organelle of a cell. In some embodiments, the organelle includes, without limitation, a nucleus, an endoplasmic reticulum, a mitochondrion, an endosome, a lysosome, a Golgi apparatus, a cell membrane, a nuclear membrane, and combinations thereof.

Thiols

The environments of the present disclosure may include various concentrations of thiols. For instance, in some embodiments, the environment has a thiol concentration ranging from about 1 fM to about 100 M. In some embodiments, the environment has a thiol concentration ranging from about 1 fM to about 1 M. In some embodiments, the environment has a thiol concentration ranging from about 0.5 mM to about 50 mM. In some embodiments, the environment has a thiol concentration ranging from about 0.5 mM to about 5 mM. In some embodiments, the environment has a thiol concentration ranging from about 1 mM to about 10 mM. Additional thiol concentrations can also be envisioned.

The methods and probe molecules of the present disclosure may also be utilized to detect various types of thiols. In some embodiments, the thiol is an organic or inorganic compound that includes at least one sulfur atom. In some embodiments, the thiol is a small molecule. In some embodiments, the thiol is not part of a protein or a polypeptide. In some embodiments, the thiol includes, without limitation, cysteine, homocysteine, methionine, glutathione, lipoic acid, coenzyme A, hydrogen sulfide, hydrosulfide anion, persulfide, thio-sulfate, sulfite, and combinations thereof. In some embodiments, the thiol includes glutathione.

Exposing Environments to Probe Molecules

Various methods may also be utilized to expose an environment to a probe molecule. For instance, in some embodiments, the exposing includes incubating the probe molecule with the environment. In some embodiments, the exposing may also include additional steps. For instance, in some embodiments where the environment is a cell, the exposing may also include steps such as electroporation, transfection, lipofection, and combinations thereof.

Various concentrations of a probe molecule may be exposed to an environment. In some embodiments, probe molecule concentrations may be significantly lower than thiol concentrations in an environment. In some embodiments, the probe molecule is exposed to an environment at a concentration that is at least 10 times lower than the thiol concentration of the environment. In some embodiments, the probe molecule is exposed to an environment at a concentration that is at least 20 times lower than the thiol concentration of the environment. In some embodiments, the probe molecule is exposed to an environment at a concentration that is at least 200 times lower than the thiol concentration of the environment.

In some embodiments, the probe molecule is exposed to an environment at a concentration between about 1 fM to about 100 mM. In some embodiments, the probe molecule is exposed to an environment at a concentration between about 1 pM to about 100 μM. In some embodiments, the probe molecule is exposed to an environment at a concentration between about 1 nM to about 500 nM. In some embodiments, the probe molecule is exposed to an environment at a concentration between about 1 nM to about 100 nM. In some embodiments, the probe molecule is exposed to an environment at a concentration of about 50 nM. In some embodiments, the probe molecule is exposed to an environment at a concentration of less than about 50 nM.

Thiol and Probe Molecule Reactions

The probe molecules of the present disclosure may react with thiols in various manners. For instance, in some embodiments, the probe molecules of the present disclosure react with thiols in a reversible manner. In some embodiments, the reversible reaction occurs through a Michael addition reaction. In some embodiments, the thiol is the Michael donor and the thiol responsive group of the probe molecule is the Michael acceptor.

In some embodiments, the probe molecules of the present disclosure selectively react with a particular thiol in an environment. For instance, in some embodiments, a probe molecule may selectively react with glutathione while not reacting with other thiols in the environment, such as albumin, cysteine and thiolated proteins. In some embodiments, the reaction occurs through the thiol responsive group of the probe molecule.

The probe molecules of the present disclosure may have various affinities for a thiol in an environment. For instance, in some embodiments, the probe molecule and the thiol have a $K_d$ value that ranges from about 1 pM to about 10 M. In some embodiments, the probe molecule and the thiol have a $K_d$ value that ranges from about 0.1 mM to about 100 mM. In some embodiments, the probe molecule and the thiol have a $K_d$ value of about 5 mM. In some embodiments, the probe molecule and the thiol have a $K_d$ value of about 1.5 mM.

Ratiometric Change in Spectrometric Property

The reaction of a probe molecule with a thiol in an environment can have various effects. For instance, in some embodiments, a reaction between a thiol in an environment and a probe molecule causes a ratiometric change in a spectrometric property of the probe molecule and the probe-thiol adduct. A ratiometric change in a spectrometric property of the probe molecule and the probe-thiol adduct generally refers to a relative change in the spectrometric property. For instance, in some embodiments, the spectrometric property of a probe molecule changes upon reaction with a thiol such that the formed probe-thiol adduct has a spectrometric property that is different from the spectrometric property of the unreacted probe molecule. In some embodiments, the spectrometric property of the unreacted probe molecule remains unchanged while the spectrometric property of the probe-thiol adduct changes.

Various ratiometric changes in spectrometric properties of a probe molecule and a probe-thiol adduct can occur after a reaction of a probe molecule with a thiol in an environment. In some embodiments, the ratiometric change includes, without limitation, a shift in absorption, a shift in fluorescence, a shift in phosphorescence, a shift in luminescence, a shift in fluorescence polarization, a shift in fluorescence lifetime imaging (FLIM), a shift in infrared Raman scattering, a shift in emission spectra, a shift in stimulated emission, a shift in nuclear magnetic resonance (NMR), a shift in magnetic resonance imaging (MRI), a shift in mass spectrometry, a shift in static light scattering, a shift in dynamic light scattering, a shift in refractive index (RI), and combinations thereof.

In some embodiments, the ratiometric change in the spectrometric property of the probe molecule and the probe-thiol adduct includes a change in an emission spectra. In some embodiments, the ratiometric change in a spectrometric property of the probe molecule and the probe-thiol adduct includes a change in intensity ratios of the emission spectra of the probe molecule and the probe-thiols adduct.

In some embodiments, the ratiometric change in the emission spectra includes a shift in light absorbance wavelength. In some embodiments, the ratiometric change in a spectrometric property of the probe molecule and the probe-thiol adduct includes a shift in fluorescence wavelength. In some embodiments, the ratiometric change in a spectrometric property of the probe molecule and the probe-thiol adduct includes a shift in light absorbance wavelength and a shift in fluorescence wavelength. For instance, in some embodiments, a probe molecule may absorb light at 479 nm and fluoresce at 590 nm. Upon reacting with a thiol, the absorbance and fluorescence peaks of the probe molecule (now referred to as a probe-thio adduct) may shift to 406 nm and 463 nm, respectively.

Correlation of Ratiometric Change to Thiol Presence in Environment

In some embodiments, the methods of the present disclosure also include a step of correlating a ratiometric change in a spectrometric property of the probe molecule and the probe-thiol adduct to the presence of a thiol in an environment. In some embodiments, the correlating includes instrumental detection of the ratiometric change in the spectrometric property. In some embodiments, the instrumental detection may occur by flow cytometry.

In some embodiments, the correlating includes visual detection of the ratiometric change in the spectrometric property. In some embodiments, the visual detection may occur by fluorescence microscopy. In some embodiments, the visual detection may occur by confocal microscopy.

In some embodiments, the step of correlating the ratiometric change in the spectrometric property of the probe molecule and the probe-thiol adduct to the presence of a thiol in an environment includes quantifying the thiol concentration in the environment. In some embodiments, the correlating includes quantifying the thiol concentration in the environment by comparing the ratiometric change of the spectrometric property of the probe molecule and the probe-thiol adduct in the environment to the ratiometric change of the spectrometric property of the probe molecule and the probe-thiol adduct in the presence of known concentrations of the thiol.

In some embodiments, the comparison step includes a comparison of the absorbance and fluorescence intensities of the probe molecule in an environment with the absorbance and fluorescence intensities of the probe molecule in the presence of known concentrations of the thiol. In some embodiments, the comparison step includes the application of a calibration curve.

Probe Molecules

The methods of the present disclosure may utilize various probe molecules to detect the presence of thiols in environments. Additional embodiments of the present disclosure pertain to the probe molecules that are utilized to detect thiols in environments. In some embodiments, the probe molecule includes a marker and a thiol responsive group. In some embodiments, the marker and the thiol responsive group are covalently linked to one another at various positions. In some embodiments, the probe molecule also includes an organelle targeting moiety.

As set forth in more detail herein, the probe molecules of the present disclosure can include various types of markers, thiol responsive groups and organelle targeting moieties in various arrangements. Furthermore, the probe molecules of the present disclosure can be conjugated to various macromolecules in various arrangements to form multivalent probes. For instance, in some embodiments, the macromolecules can include, without limitation, liposomes, micelles, nanoparticles, microparticles, polymers, proteins, and combinations thereof.

Markers

Markers generally refer to probe molecule components that can be utilized to detect a ratiometric change in a spectrometric property of the probe molecule and the probe-thiol adduct.

The probe molecules of the present disclosure can include various types of markers. For instance, in some embodiments, the marker includes, without limitation, UV-vis absorbing moieties, dyes, fluorophores, chromophores, halogens, azides, alkynes, cyano groups, and combinations thereof. In some embodiments, the marker has an absorption of at least about 200 nm. In some embodiments, the marker is fluorescent.

In some embodiments, the marker includes a chromophore. In some embodiments, the chromophore is a metal chromophore. In some embodiments, the metal chromophore has the following formula:

$$M\text{-}L_n$$

In some embodiments, M is a metal, L is a ligand, and n is a number of at least 1.

In some embodiments, the marker may be a small moiety within a probe molecule, such as a chromophore or a $CF_3$ moiety. In some embodiments, the marker may include a larger structure. For instance, in some embodiments, the marker includes one or more of the following structures or combinations of the following structures:

(1)

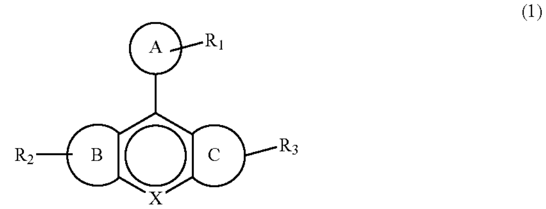

(2)

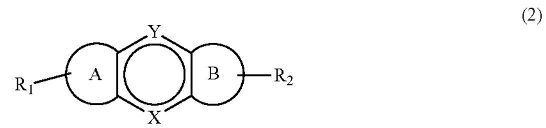

(3)

$R_1$ A B $R_2$ (4)

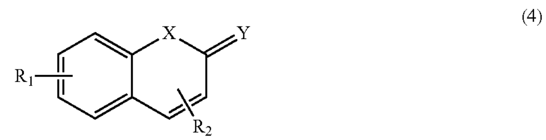

-continued (5)

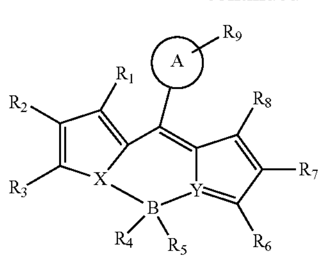

(6)

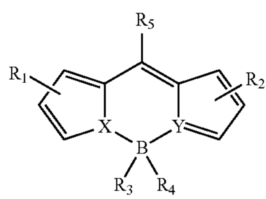

(7)

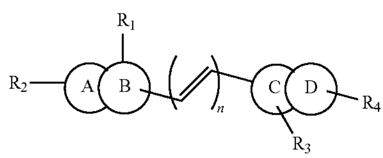

(8)

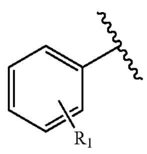

(9)

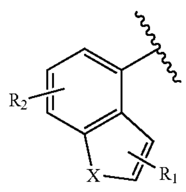

Structures 1-9 may include numerous variations. For instance, A, B, C and D in the aforementioned structures may include, without limitation, phenyls, substituted phenyls, heterocycles, substituted heterocycles, aromatic groups, substituted aromatic groups, cyclic groups, and combinations thereof.

Likewise, $R_1$-$R_9$ in structures 1-9 may include various moieties. In some embodiments, each of $R_1$-$R_9$ can include a single moiety. In some embodiments, each of $R_1$-$R_9$ can include a plurality of moieties. For instance, in some embodiments, each of $R_1$-$R_9$ can represent two separate moieties. In some embodiments, $R_1$, $R_2$, $R_3$, $R_4$, $R_5$, $R_6$, $R_7$, $R_8$ and $R_9$ can each include, without limitation, H, OH, $NH_2$, $CH_3$, alkanes, alkenes, alkynes, alkyl groups, azides, cyano groups, aryl groups, substituted aryl groups, phenyl groups, substituted phenyl groups, heterocycles, substituted heterocycles, aromatic groups, substituted aromatic groups, cyclic groups, alkoxyl groups, carboxyl groups, carbonyl groups, ethers, esters, acetyl groups, acetoxy groups, acetomethoxy groups, acetoxymethyl esters, acetoxyalkyl esters, alkoxyalkyl esters, boron containing groups, silicon containing groups, phosphorous containing groups, sulfur containing groups, arsenic containing groups, germanium containing groups, selenium containing groups, aluminum containing groups, tin containing groups, antimony containing groups, tellurium containing groups, lead containing groups, bismuth containing groups, polonium containing groups, amine groups, amides, cycloamines, cycloamines comprising —$N(CH_2)_n$, Br, F, Cl, I, CN, NO, $NO_2$, $CF_3$, $CHF_2$, $CH_2F$, $CCl_3$, $CH_2Cl$, $CHCl_2$, $CBr_3$, $CH_2Br$, $CHBr_2$, $CI_3$, $CH_2I$, $CHI_2$, $CF_2Cl$, $CFCl_2$, $CF_2Br$, $CFBr_2$, $CF_2I$, $CFI_2$, $CCl_2Br$, $CClBr_2$, $CCl_2I$, $CClI_2$, $CBr_2I$, $CBrI_2$, $CH_3O$, $CO_2H$, $CO_2CH_3$, $CO_2R_A$, $CON(R_A)(R_B)$, $CONH_2$, $COR_A$, $SO_3H$, $SO_3R_A$, $SO_2R_A$, $SO_2H$, $SOR_A$, CHO, $CH_2R_A$, $CHR_AOCOR_B$, $CHR_AR_B$, $CR_AR_BR_C$, $NHR_A$, $NR_AR_B$, $NR_A(CH_2)_nR_B$, $NR_AC((CH_2)_n—OR_B)_3$, $N(C_2H_5)_2$, $N((CH_2)_nCOR_A)_2$, $OR_A$, $SiH_3$, $SiH_2R_A$, $SiHR_AR_B$, $SiR_AR_BR_C$, $PH_2$, $PHR_A$, $PR_AR_B$, SH, $SR_A$, $PO_3H_2$, $PO_3HR_A$, $PO_3(R_A)_2$, organelle targeting moieties, polymers, and combinations thereof.

$R_A$, $R_B$, and $R_C$ in structures 1-9 can also include various moieties. In some embodiments, $R_A$, $R_B$, and $R_C$ can each include, without limitation, H, OH, $CH_3$, alkanes, alkenes, alkynes, alkyl groups, azides, cyano groups, aryl groups, substituted aryl groups, phenyls, substituted phenyls, heterocycles, substituted heterocycles, aromatic groups, substituted aromatic groups, cyclic groups, alkoxyl groups, carboxyl groups, carbonyl groups, ethers, esters, acetyl groups, acetoxy groups, acetomethoxy groups, acetoxymethyl esters, acetoxyalkyl esters, alkoxyalkyl esters, boron containing groups, silicon containing groups, phosphorous containing groups, sulfur containing groups, arsenic containing groups, germanium containing groups, selenium containing groups, aluminum containing groups, tin containing groups, antimony containing groups, tellurium containing groups, lead containing groups, bismuth containing groups, polonium containing groups, amine groups, amides, Br, F, Cl, I, CN, $NH_2$, NO, $NO_2$, $CF_3$, $CHF_2$, $CH_2F$, $CCl_3$, $CH_2Cl$, $CHCl_2$, $CBr_3$, $CH_2Br$, $CHBr_2$, $CI_3$, $CH_2I$, $CHI_2$, $CF_2Cl$, $CFCl_2$, $CF_2Br$, $CFBr_2$, $CF_2I$, $CFI_2$, $CCl_2Br$, $CClBr_2$, $CCl_2$, $CClI_2$, $CBr_2I$, $CBrI_2$, $CH_3O$, $CO_2H$, $CH_2CO_2H$, $CH_2OCOCH_3$, $CH_2OCOR$, $CO_2CH_3$, $CONH_2$, $C_2H_5$, organelle targeting moieties, polymers, and combinations thereof.

X and Y in structures 1-9 can also include various moieties. In some embodiments, X and Y can each include, without limitation, C, CH, $CH_2$, $CHR_A$, $CR_AR_B$, N, NH, $NH_2$, $NHR_A$, $NR_AR_B$, O, OH, Se, BH, $OR_A$, Si, SiH, $SiH_2$, $SiHR_A$, $SiR_AR_B$, P, PH, $PH_2$, $PHR_A$, $PR_AR_B$, S, SH, $SR_A$, and combinations thereof. In some embodiments, $R_A$ and $R_B$ can include moieties that were described previously.

In some embodiments, the marker includes one or more of the following structures or combinations of the following structures:

(10)

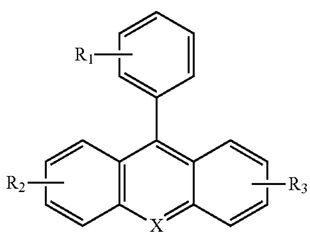

(11)

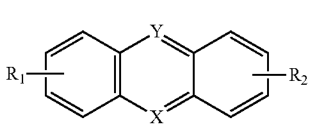

-continued (12)

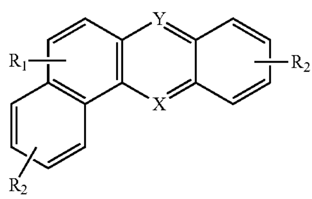

(13)

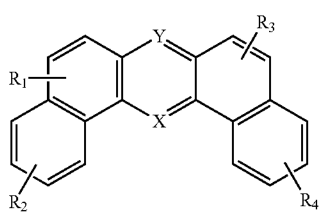

(14)

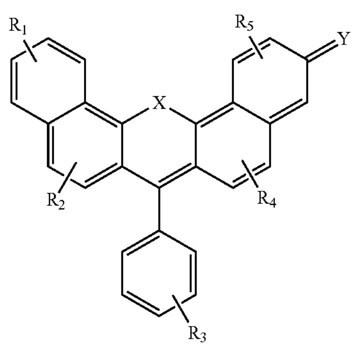

(15)

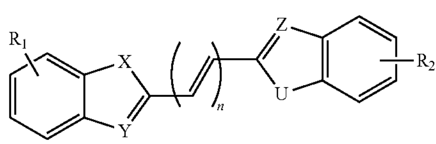

(16)

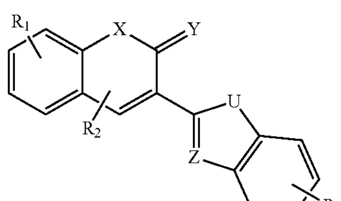

(17)

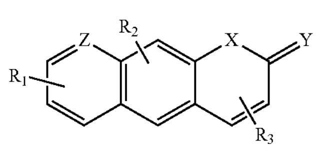

(18)

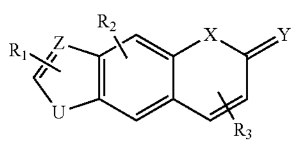

Structures 10-18 may also include numerous variations. For instance, X, Y, Z, and U in structures 10-18 can each include, without limitation, C, CH, $CH_2$, $CHR_A$, $CR_AR_B$, N, NH, $NH_2$, $NHR_A$, $NR_AR_B$, O, OH, Se, BH, $OR_A$, Si, SiH, $SiH_2$, $SiHR_A$, $SiR_AR_B$, P, PH, $PH_2$, $PHR_A$, $PR_AR_B$, S, SH, $SR_A$, and combinations thereof.

In some embodiments, $R_A$ and $R_B$ in structures 10-18 can include moieties that were described previously. $R_1$-$R_5$ in structures 10-18 can also include moieties that were described previously.

Thiol Responsive Groups

The probe molecules of the present disclosure can also include various thiol responsive groups. Thiol responsive groups generally refer to molecules or moieties that can reversibly react with a thiol in an environment to form a probe-thiol adduct.

The probe molecules of the present disclosure can include various thiol responsive groups. For instance, in some embodiments, the thiol responsive group includes an esterified carboxylic acid group. In some embodiments, the thiol responsive group includes one or more of the following structures or combinations of the following structures:

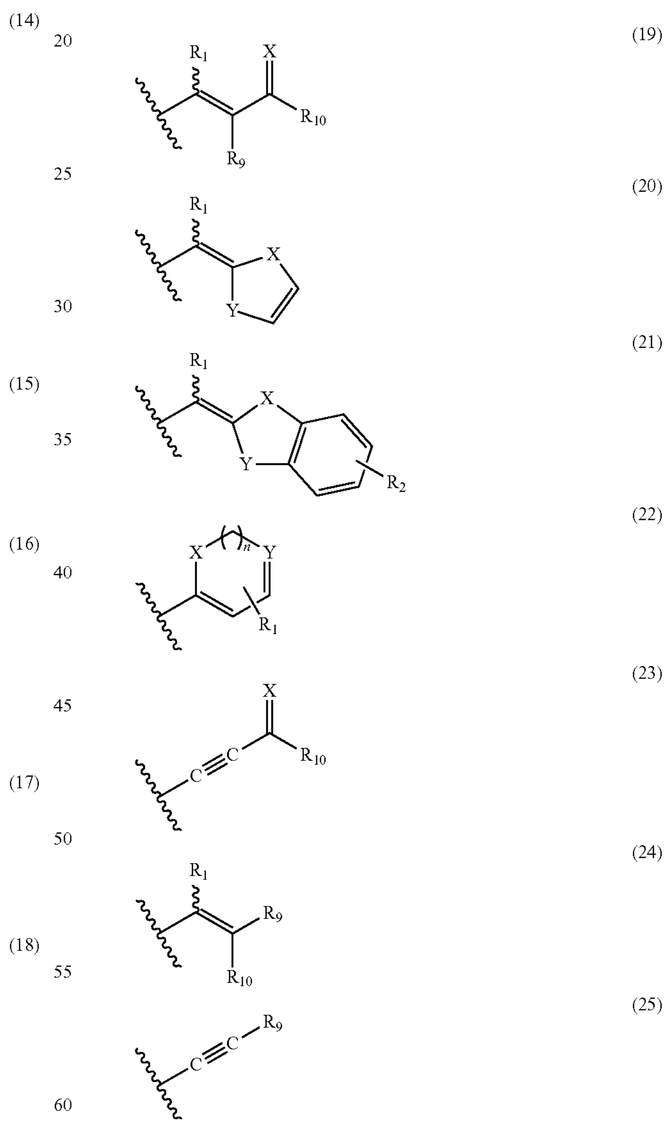

Structures 19-25 may also include numerous variations. For instance, X and Y in structures 19-25 can each include moieties that were described previously. Likewise, $R_1$-$R_2$ and $R_9$-$R_{10}$ in structures 19-25 can include moieties that were described previously. In some embodiments, $R_{10}$ in structures 19-25 can include one or more of the following structures or combinations of the following structures:

(26)

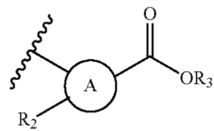

(27)

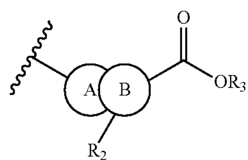

(28)

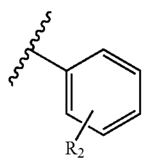

(29)

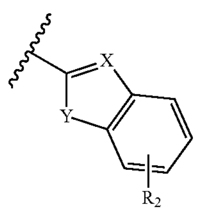

(30)

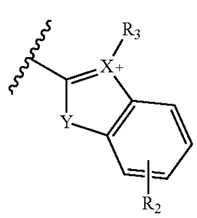

Structures 26-30 may also include numerous variations. For instance, A and B in structures 26-30 can each include compositions that were described previously. Likewise, X and Y and $R_2$-$R_3$ in structures 26-30 can each include moieties that were described previously.

Organelle Targeting Moieties

In some embodiments, the probe molecules of the present disclosure can also include one or more organelle targeting moieties. Organelle targeting moieties generally refer to one or more moieties that can facilitate the transport of a probe molecule to a particular organelle. In some embodiments, the organelle targeting moiety may be part of the thiol responsive group of the probe molecule. In some embodiments, the organelle targeting moiety may be part of the marker of the probe molecule. In some embodiments, the organelle targeting moiety includes, without limitation, nuclear targeting moieties, endoplasmic reticulum targeting moieties, mitochondrial targeting moieties, endosome targeting moieties, lysosome targeting moieties, Golgi targeting moieties, cell membrane targeting moieties, nuclear membrane targeting moieties, and combinations thereof. Examples of various organelle targeting moieties are provided in FIG. 32.

Probe Molecule Attributes and Structures

The probe molecules of the present disclosure can have various attributes. For instance, in some embodiments, the probe molecule is cell permeable. In some embodiments, the probe molecule is water soluble. In some embodiments, the probe molecule includes functional groups that make the probe molecule water soluble. In some embodiments, the functional groups include ester groups, such as esterified carboxylic acid groups.

As set forth previously, the probe molecules of the present disclosure can include various types of markers, thiol responsive groups and organelle targeting moieties in various arrangements. In more specific embodiments, the probe molecules of the present disclosure include the following structure:

(31)

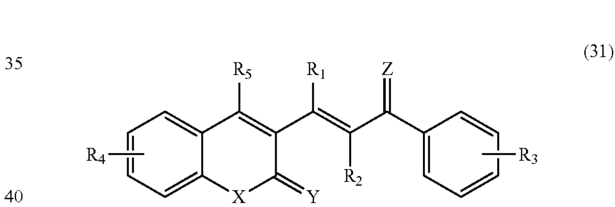

Structure 31 can also include numerous variations. For instance, X Y, Z and $R_1$-$R_5$ in structure 31 can each include various moieties that were described previously.

In further embodiments, the probe molecules of the present disclosure can include one or more of the following structures or combinations of the following structures:

(32)

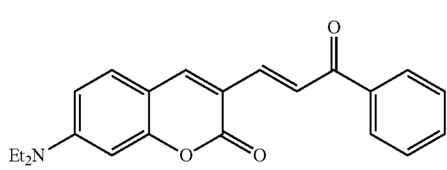

(33)

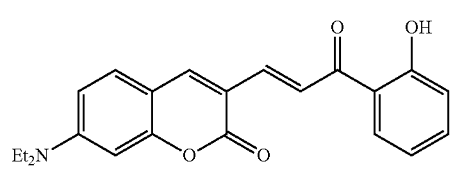

(34)

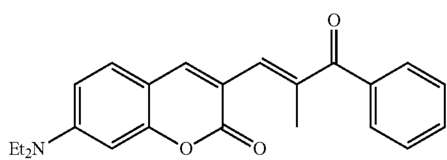

(35)

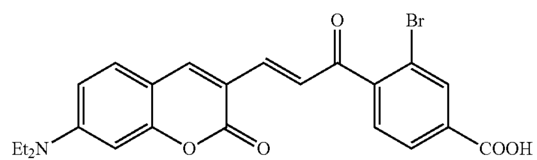

-continued
(36)
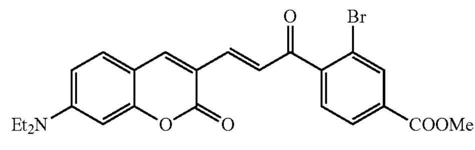
(37)
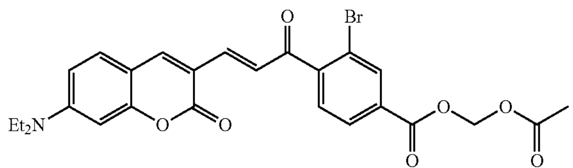
(38)
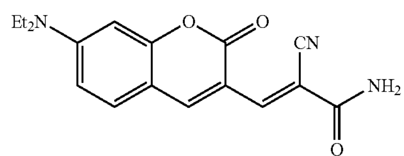
(39)
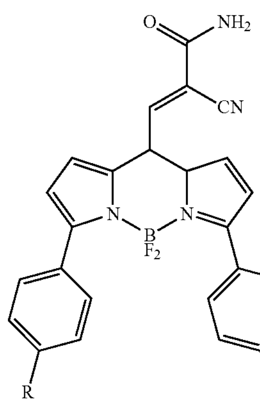
(40)
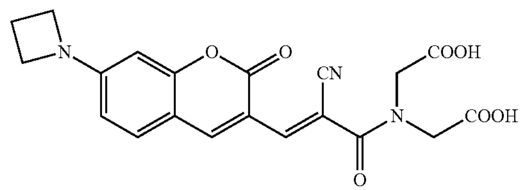
(41)
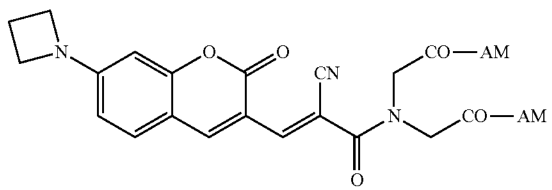
(42)
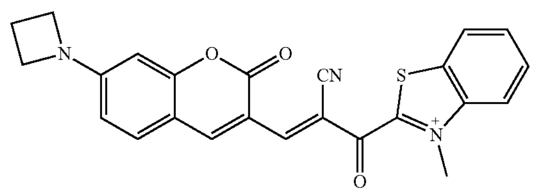
(43)
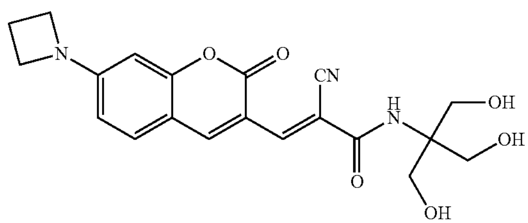
(44)
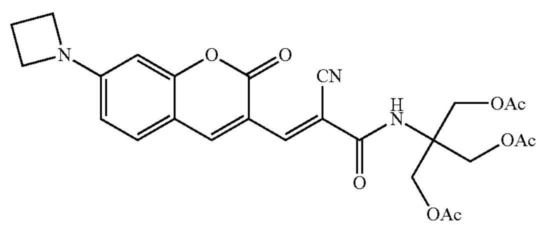
(45)
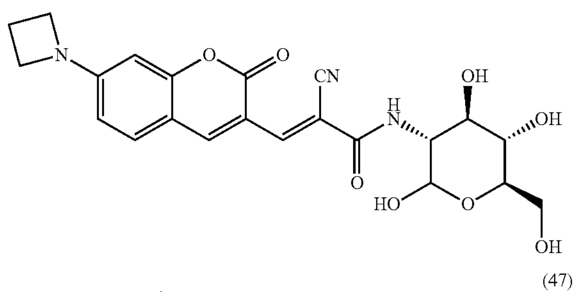
(46)
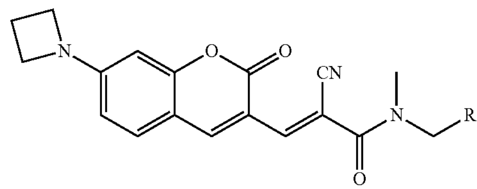
(47)
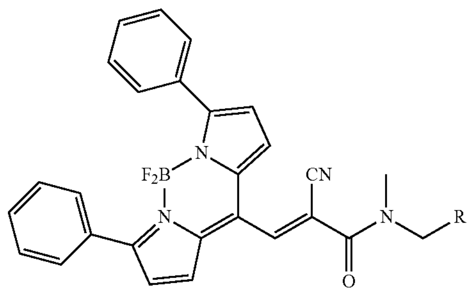

-continued
(48)
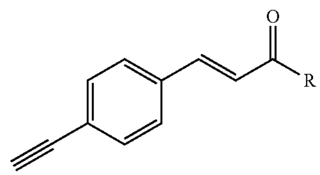
(49)
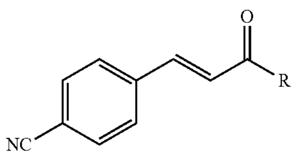
(50)
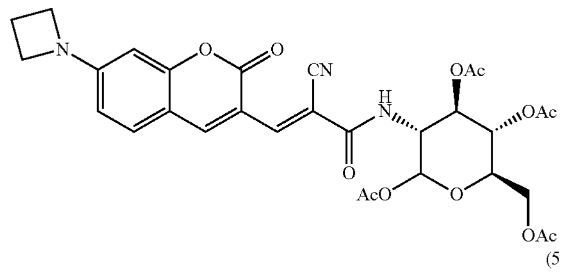
(51)
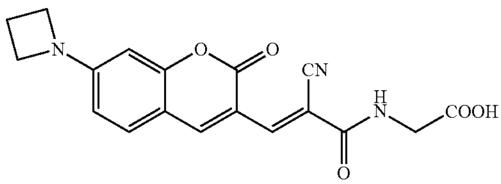
(52)
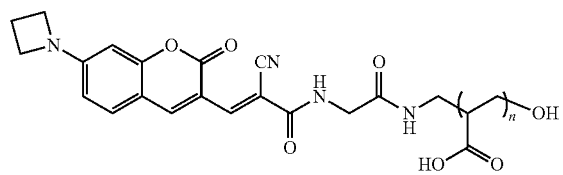
(53)
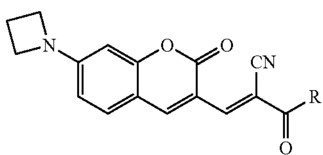
(54)
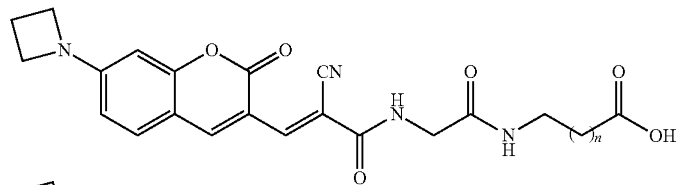
(55)
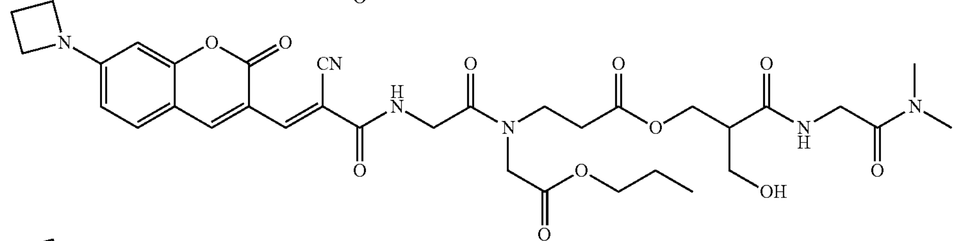
(56)
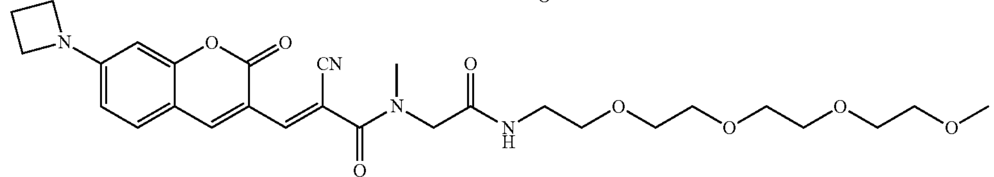
In some embodiments, R (in structures 39, 46-49 and 53), and AM (in structure 41) can include moieties that were described previously for $R_1$-$R_{10}$. In some embodiments, R (in structures 39 and 46-49 and 53) can include, H, OMe, and combinations thereof. In some embodiments, AM (in structure 41) can include $CH_2OCOCH_3$.
In some embodiments, R in structure 46 includes one of
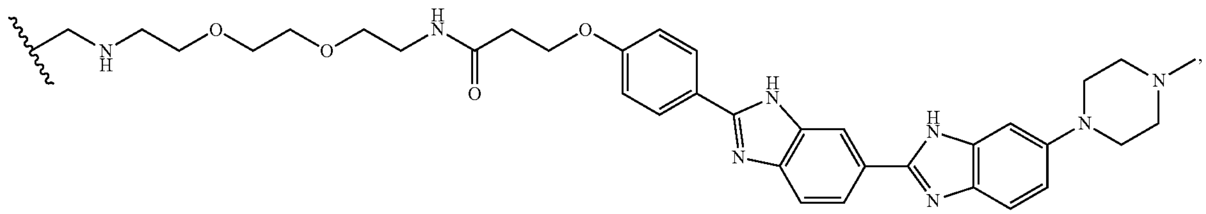

-continued

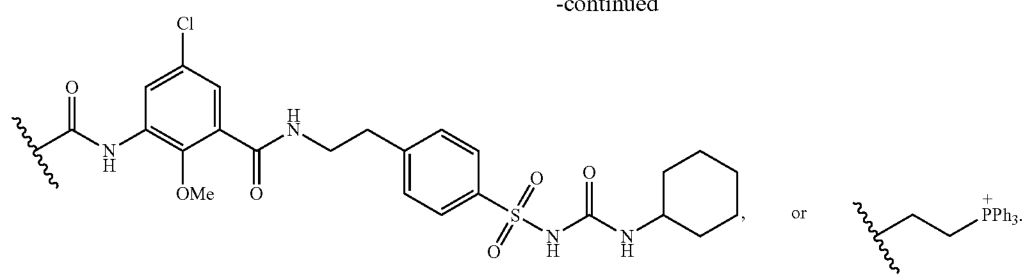

Advantages

As set forth in the Examples herein, the methods and probe molecules of the present disclosure can provide numerous advantages. For instance, the probe molecules of the present disclosure can be utilized at low concentrations (e.g., as low as 20 nM) to quantify thiols at low concentration ranges (e.g., 0.5 mM-50 mM) in various environments. Moreover, the probe molecules of the present disclosure can demonstrate specificity towards various thiols (e.g., GSH) while demonstrating inertness towards other thiols, such as thiolated proteins at their physiological concentrations. Furthermore, the probe molecules of the present disclosure can allow for the monitoring of thiol concentrations in real-time in various environments, such as in living cells, in specific organelles of cells, and in animals. In addition, the methods and probe molecules of the present disclosure can be utilized to track thiols in real-time in living cells at organelle-level resolution.

Unlike existing probes, the probe molecules of the present disclosure have negligible effects on the cellular redox status while allowing convenient applications to hard-to-transfect cells, such as primary cells in living animals. Unlike existing probes, the probe molecules of the present disclosure can also provide absolute quantification of thiols instead of a ratio of thiols and their disulfide counter-parts, which has been debated for its biological meaning.

Furthermore, the probe molecules of the present disclosure can be used not only in high resolution confocal microscope imaging to measure thiol levels, but also in high throughput bulk measurements using flow cytometry.

Additional Embodiments

Reference will now be made to more specific embodiments of the present disclosure and experimental results that provide support for such embodiments. However, Applicants note that the disclosure herein is for illustrative purposes only and is not intended to limit the scope of the claimed subject matter in any way.

Example 1. Quantitative Imaging of Glutathione in Live Cells Using a Reversible Reaction-Based Ratiometric Fluorescent Probe In this Example, Applicants report a first fluorescent probe for the quantitative imaging of glutathione (GSH) in live cells. This Example is also included in the following publication by Applicants: *ACS Chem. Biol.,* 2015, 10 (3), pp 864-874. The fluorescent probe is referred to herein as ThiolQuant Green or TQ Green. Due to the reversible nature of the reaction between the probe and GSH, Applicants are able to quantify mM concentrations of GSH with TQ Green concentrations as low as 20 nM. Furthermore, the GSH concentrations measured using TQ Green in 3T3-L1, HeLa, HepG2, PANC-1, and PANC-28 cells are reproducible and well correlated with the values obtained from cell lysates. TQ Green imaging can also resolve the changes in GSH concentration in PANC-1 cells upon diethylmaleate (DEM) treatment. In addition, TQ Green can be conveniently applied in fluorescence activated cell sorting (FACS) to measure GSH level changes. Through this Example, Applicants not only demonstrate the importance of reaction reversibility in designing quantitative reaction-based fluorescent probes, but also provide a practical tool to facilitate redox biology studies.

In this Example, Applicants exploited the reversible Michael addition reaction to design a ratiometric probe that can quantify intracellular GSH concentration. It should be noted that despite the attempts to use Michael addition reaction for GSH probes, inappropriate $K_{eq}$ of these probes account for the failure of GSH quantification. In this study, analyte GSH is the Michael donor and the probe is the Michael acceptor.

As illustrated in FIG. 2, Applicants chose a modular design for the GSH ratiometric probes. Module A is protected 7-amino coumarin, whose fluorescence (Fl) property is suitable for confocal experiments. Module C is a modulator with an aromatic structure to extend the absorption (Abs) wavelength of module A, and module B is the reaction center of the Michael acceptor that connects modules A and C. Upon reaction with GSH, the extended conjugation of 1 is interrupted to form 2, causing a hypsochromic shift in both Abs and Fl. Quantification of the Fl emission ratios of 1 and 2 allows Applicants to deduce the GSH concentration, following previously reported procedures for $Ca^{2+}$ ratiometric probes. The $K_{eq}$ with GSH and the time to reach equilibrium can be adjusted by altering the $R^1$, $R^2$, and $R^3$ substituents.

After a few iterations (Table 1), Applicants developed probe 3, designated as TQ Green. TQ Green has an appropriate $K_{eq}$ with GSH.

TABLE 1

Development of ThiolQuant Green (TQ Green).

| Structure | Solubility | $K_d'$*** |
|---|---|---|
| 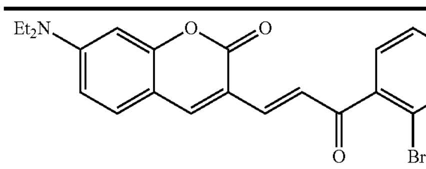 3 ThiolQuant Green (TQ Green) | Water * | 14.8 mM |
| 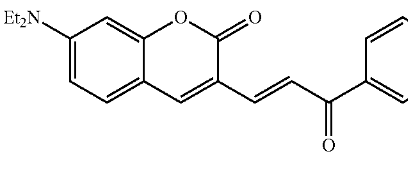 3a | Water * | 1.5 mM |
| 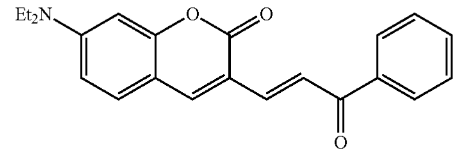 3b | DMSO ** | N/A |
| 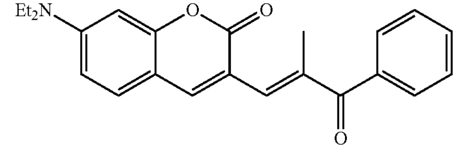 3c | DMSO ** | N/A |
| 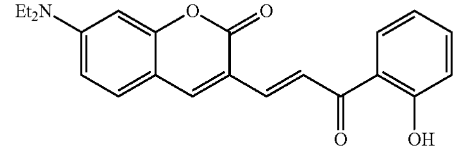 3d | DMSO ** | ~2 mM |

* Solubility in PBS buffer > 0.5 mM

** Solubility in PBS buffer < 10 μM

*Observed dissociation constant ($K_d'$) was determined by reaction with various concentration of GSH in water and β-mercaptoethanol in DMSO TQ Green displays ratiometric change in spectroscopic properties upon reaction with GSH in a phosphate-buffered saline at pH 7.4 (PBS). TQ Green absorbs at 479 nm and fluoresces at 590 nm ($\lambda_{ex}$=488 nm, FIG. 3**). The extinction coefficients of TQ Green and TQ Green-GSH at their maximum absorption wavelengths are $(2.3\pm0.2)\times10^4$ $M^{-1}\cdot cm^{-1}$ (a, =479 nm, Table 2) and $(1.6\pm0.2)\times10^4$ $M^{-1}\cdot cm^{-1}$ ($\lambda_{max}$=407 nm, Table 1), respectively. Upon reacting with GSH, the Abs and Fl peaks shift hypsochromically to 406 and 463 nm ($\lambda_{ex}$=405 nm), respectively. The Abs of TQ Green and TQ Green-GSH (the adduct between TQ Green and GSH) are close to 488 and 405 nm, respectively, which are two commonly used laser wavelengths for confocal microscopes. For all the following experiments, excitation and absorption wavelengths 488 and 405 nm were used.

TABLE 2

Summary of physical chemical properties of TQ Green and TQ Green-GSH.

| | TQ Green | TQ Green-GSH |
|---|---|---|
| Abs Max Wavelength | 479 nm | 406 nm |
| Fl Emission Max Wavelength | 590 nm ($\lambda_{ex}$ = 488 nm) | 463 nm ($\lambda_{ex}$ = 405 nm) |
| Extinction Coefficient | (2.3 ± 0.2) × $10^4$ $M^{-1}\cdot cm^{-1}$ (at $\lambda_{max}$ = 479 nm) | (1.6 ± 0.2) × $10^4$ $M^{-1}\cdot cm^{-1}$ (at $\lambda_{max}$ = 406 nm) |
| Quantum Yield (PBS) | 0.0094 ± 0.0004 ($\lambda_{ex}$ = 479 nm) | 0.0059 ± 0.0003 ($\lambda_{ex}$ = 406 nm) |
| Quantum Yield (Methanol) | 0.16 ± 0.05 ($\lambda_{ex}$ = 488 nm) | NA[a] |

TABLE 2-continued

Summary of physical chemical properties of TQ Green and TQ Green-GSH.

| | TQ Green | TQ Green-GSH |
|---|---|---|
| Log D (pH = 7.4) | 0.70 | NA[b] |
| Pseudo First-Order Constant | $k_{obs}$ = (5.98 ± 0.03) × $10^{-3}$ $s^{-1}$; $t_{1/2}$ = 116 s (concentration: TQ Green at 20 μM; GSH at 40 mM) | |
| Second-Order Rate Constant | 0.150 ± 0.001 $M^{-1} \cdot s^{-1}$ | |
| Equilibrium Constants | $K_d'$ = 14.8 mM (based on UV-Vis) $K_d$ = 1.6 mM | |

[a]TQ Green-GSH is not soluble in methanol

[b]TQ Green-GSH and GSH are not soluble in octanol thus not suitable for standard Log D measurement, the estimated value based on HPLC result is <−1.0.

The reaction between TQ Green and GSH is reversible. To demonstrate this reversibility, three experiments were performed. First, when incubating TQ Green (20 μM) with excessive amounts of GSH (40 mM) in PBS, the Abs at 488 nm decreased with a concurrent increase at 405 nm following a pseudo first-order kinetics ($k_{obs}$=(5.98±0.03)×$10^{-3}$ $s^{-1}$ and half-life of 116 seconds based on a global fitting for the decay and growth at 488 and 405 nm, respectively (Table 2 and FIG. 4A).

The second-order rate constant between TQ Green and GSH is 0.150±0.001$M^{-1}\cdot s^{-1}$. There were no appreciable Abs changes observed after 20 minutes. Following a pause for another 80 minutes to ensure that the equilibrium between TQ Green and GSH was fully established, Applicants added two equivalents of an irreversible Michael acceptor (5,6-dihydro-2H-pyran-2-one) to deplete all the GSH in solution (FIG. 4A). Applicants observed almost full restoration of the absorbance values at 405 and 488 nm, demonstrating the reversibility of the reaction between TQ Green and GSH.

In the second experiment, Applicants allowed TQ Green (16 μM) to react with different concentrations of GSH (0-20 mM) under anaerobic conditions for 1 hour, 18 hours, and 72 hours (as illustrated in FIG. 5, GSH is easily oxidized in air). No significant changes in Abs or Fl were observed at these three time points, indicating reaction equilibria were fully established 1 hour after reaction. An increase in concentration of GSH resulted in a decrease of Abs at 488 nm with a concurrent increase at 405 nm with an isosbestic point at 426 nm (FIG. 4B). If the reaction between TQ Green and GSH were irreversible, TQ Green would be completely consumed, allowing enough reaction time and would not behave in a concentration dependent manner.

In the third experiment, GSH was added to a solution of TQ Green in three portions with 90 minute intervals that served to ensure that equilibrium was fully established. R is defined as the ratio of the signal intensities (Absorbance or Fl) between TQ Green-GSH and TQ Green. $R_{min}$ and $R_x$ correspond to the R values at zero and saturated GSH concentrations (80 mM), respectively. $(R-R_{min})/(R_{max}-R)$, which is proportional to the GSH concentration (vide infra), plateaued within 90 minutes after addition of GSH (FIG. 4C). Introduction of additional GSH caused $(R-R_{min})/(R_{max}-R)$ changes and re-establishment of the reaction equilibrium. This experiment demonstrated that, unlike previously reported GSH probes, TQ Green can respond to the changes in GSH concentrations. Overall, the three experiments demonstrated the reversible nature of the reaction between TQ Green and GSH as well as the effectiveness and necessity for developing reversible reaction-based small molecule probes.

Applicants also determined $K_{eq}$ between TQ Green and GSH and the relationship of the ratiometric change as a function of GSH concentration. $K_d'$ is the apparent dissociation constant for the reaction between TQ Green and GSH. The following equation can be derived:

$$\frac{R-R_{min}}{R_{max}-R}=\frac{[GSH]}{K_d'}$$

Plotting $(R-R_{min})/(R_{max}-R)$ as a function of GSH concentration afforded a superb linear relationship with $r^2$=0.999 (FIGS. 6-7). The reciprocal of the slope affords $K_d'$ as 14.8 mM (assuming at 80 mM of GSH, TQ Green is fully converted to TQ Green-GSH).

It should be noted that some previous studies plotted R directly against analyte concentration to afford a linear relationship. It should be cautioned that this type of linear relationship is valid only when: 1) there is no spectral overlap between the absorption and/or emission bands from probe and probe-analyte adduct; or 2) the dissociation constant is much larger (preferably 100 times larger) than the analyte concentration. In this Example, because the spectral overlap at the two monitoring wavelengths occurs, plotting R against GSH concentration confers a non-linear relationship.

Comparing the absorption values of TQ Green and TQ Green-GSH at 488 nm, Applicants can calculate $$\frac{\varepsilon_{CouBro,488nm}}{\varepsilon_{CouBro-GSH,488nm}}=9.2,$$

based on the relationship that $$K_d'=K_d\frac{\varepsilon_{CouBro,488nm}}{\varepsilon_{CouBro-GSH,488nm}}.$$

Accordingly, Applicants can deduce that $K_d$=1.6 mM (FIG. 8).

Meanwhile, TQ Green showed good specificity towards GSH under physiological conditions. Free cysteine and the surface exposed cysteine residues on proteins inside cells could potentially compete with GSH in TQ Green reactions. It is known that, in contrast to the 1-10 mM concentrations of GSH inside cells, cysteine concentrations are in the range of 0.1-1 mM, approximately an order of magnitude lower than GSH levels. Assuming cysteine and GSH have similar reactivities, the presence of cysteine will introduce an error no more than 10%. At 0.1 mM concentration of cysteine, Applicants did not observe appreciable reactions between TQ Green and cysteine within 2 hours (FIG. 9).

Proteins containing free thiol groups may also react with TQ Green to affect the measurement of GSH levels. On average, the protein concentration inside cells is 3×$10^6$ molecules/$\mu m^3$, which corresponds to a concentration of 5 mM. Assuming there is one free thiol on each protein molecule, 5 mM of bovine serum albumin (BSA) solution should reasonably mimic intracellular proteins because a) BSA has a free thiol on its surface; and b) the molecular weight of BSA (65 kDa) is close to the average molecular weight of intracellular proteins (~50 kDa). As shown in FIG. 9, TQ Green undergoes little reaction with 5 mM of BSA within the experimental time scale. Through these experiments and analyses, Applicants can conclude that TQ Green has good specificity towards GSH under physiological conditions.

In order to allow TQ Green to efficiently penetrate into cells for GSH measurements, Applicants converted the carboxylic acid group to an acetoxymethyl (AM) ester (FIG. 10). Once inside cells, the AM ester will be readily hydrolyzed by esterases to regenerate TQ Green. To verify this, Applicants incubated TQ Green-AM (FIG. 11, 40 μM) in PBS for 2 hours and in a 500 times diluted HeLa cell lysate for 10 hours at 37° C. (Note: the dilution factor for the cell lysate is calculated based on the fact that ~400,000 of HeLa cells, which have a total volume of ~2 μL, were lysed in 1 mL of lysis buffer, resulting in 500 times dilution of cellular components, Table 3). A mixture of TQ Green and TQ Green-AM standard samples and the reaction mixtures after incubation in PBS and in cell lysate were separated using high performance liquid chromatography (HPLC) with a tandem of UV-vis and mass spectrometer (MS) detectors. Applicants observed that TQ Green-AM ester is resistant to hydrolysis in PBS. In contrast, TQ Green-AM ester was completely converted to a mixture of TQ Green and TQ Green-GSH adduct after 10 hours of incubation in a diluted cell lysate based on both UV-vis and MS analyses.

Assuming esterase hydrolysis follows pseudo-first order kinetics and the concentration of TQ Green-AM is no more than 1 μM (loading concentration), TQ Green-AM will be completely hydrolyzed to TQ Green within 1 minute once inside cells. This experiment demonstrated that TQ Green-AM is a TQ Green precursor that can be efficiently regenerated inside cells. This is also consistent with the fact that AM esters are widely used in many molecular probes, such as calcium probe Fura-2 and $H_2S$ probe SF7.

Regeneration of TQ Green from TQ Green-AM under an intracellular environment is summarized in FIG. 12. TQ Green-AM (40 μM) was incubated in PBS for 2 hours and in a 500 times diluted HeLa cell lysate for 10 hours at 37° C. The reaction products were analyzed by HPLC with a tandem of UV-vis and MS detectors. Analytical standards TQ Green and TQ Green-AM (red trace C) were used to determine the retention time of the corresponding compounds. TQ Green-AM did not show appreciable hydrolysis in PBS within 2 hours (blue trace B), indicating that TQ Green-AM stays intact before entering cells under the live imaging conditions. TQ Green-AM was completely hydrolyzed after 10 hours of incubation in 500 times diluted cell lysate (green trace A), indicating that TQ Green-AM can be completely converted into TQ Green within ~1 minute under an intracellular environment. Under the elution conditions used, TQ Green and TQ Green-GSH cannot be separated. However, their identities were confirmed by MS. All the traces were offset by 0.5 minutes on x-axis and 10 mAU on y-axis from each other for clarity.

TQ Green can establish equilibrium with GSH within 30 minutes inside cells. As shown in FIG. 4, the half-life of TQ Green in 40 mM GSH solution is 116 seconds (~2 minutes) at 25° C. In a 10 mM GSH environment, the TQ Green half-life will be ~8 minutes, assuming pseudo first-order kinetics. Therefore, it takes about 3 half-lives (~24 minutes) to get ~90% consumption of TQ Green at 25° C. As a rule of thumb based on the Arrhenius equation, reaction rates generally double for every 10° C. increase in temperature. At 37° C., the intracellular environment, TQ Green should be able to establish equilibrium with GSH within 15-30 minutes, which is the incubation time used for all the following imaging experiments in this study.

To determine the subcellular distribution of TQ Green, Applicants co-stained HeLa cells with probes specific to different organelles, including mitochondria, endoplasmic reticulum (ER), lysosomes, and endosomes. In particular, HeLa cells were co-stained with TQ Green (green) and different organelle specific probes, including MitoTracker® Red, ER-Tracker™ Red, LysoTracker® Red, and Rab5-RFP fusion protein (endosome specific red fluorescent protein (RFP)).

The images are shown in FIG. 13. Orange color in the overlay column indicates colocalization. It should be noted that, due to the transfection efficiency, some of the cells did not express Rab5-RFP. TQ Green displays an extranuclear distribution pattern, which suggests TQ Green may have preference to specific organelles. Further analyses revealed that TQ Green mainly colocalizes with mitochondria and ER, and with lysosomes and endosomes to a much lesser extent (FIG. 13). Applicants infer that TQ Green that did not colocalize with any of the organelle specific markers tested resides in cytoplasm. The goal of the current Example is to determine the cytoplasmic GSH concentrations in live cells. Therefore, reduced distribution of TQ Green in nucleus does not affect quantification of cytoplasmic GSH.

Despite the fact that TQ Green colocalizes with ER and mitochondria, it is unclear whether TQ Green resides in lipid membranes or an aqueous environment, which is important to quantitative analyses because fluorophores tend to have different quantum yields in hydrophilic and hydrophobic environments. Applicants obtained the quantum yields for TQ Green and TQ Green-GSH in PBS as 0.0094±0.0004 and 0.0059±0.0003, respectively (Table 2). In contrast, the quantum yield for TQ Green increased significantly to 0.16±0.05 in an organic solvent (Note: TQ Green-GSH is not soluble in organic solvents. Therefore, the quantum yield of TQ Green-GSH in organic solvents is unavailable).

To further understand TQ Green distribution between hydrophobic and hydrophilic environments, Applicants measured the Log D values of TQ Green and TQ Green-GSH using an octanol-PBS (pH 7.4) biphasic system (Table 2). Applicants found that TQ Green has a Log D value of 0.7, indicating a preference for hydrophobic environments and, thus, the potential enrichment of TQ Green in intracellular lipid membranes. In addition, Applicants discovered that the absorbance maximum of TQ Green shifts from 480 nm to 455 nm when changing the solvents from PBS to octanol. Applicants hypothesize that if TQ Green is distributed in lipid membranes, the absorbance maximum and fluorescence intensity will change. Applicants used liposomes to mimic the lipid membranes and found that increasing concentration of liposomes indeed blue-shifts the absorption of TQ Green and enhance its fluorescence (data not shown). Consistent with the Log D measurements, this experiment also supports the hypothesis that TQ Green accumulates in lipid membranes. Considering the high quantum yield of TQ Green in hydrophobic solvents, lipid enrichment of TQ Green seemingly complicates intracellular GSH quantification. After careful analysis, Applicants found that if thermodynamic equilibria completely establish between the distributions of TQ Green and TQ Green-GSH in lipid membranes and aqueous environment and between TQ Green and GSH, the fluorescence intensity ratios of TQ Green and TQ Green-GSH are still proportional to GSH concentrations. However, the $K_d'$ values may be different under calibration conditions and inside cells, which may introduce a systemic error.

In order to quantify intracellular GSH concentration, a calibration curve for TQ Green in known concentrations of GSH was established using a confocal microscope (FIG. 14). A fixed excitation laser energy was appropriately chosen to ensure that the Fl signals of TQ Green in different concentrations of GSH fit into the dynamic range of the microscope. A calibration curve with a reasonable linearity ($r^2$=0.97) was generated using known concentrations of GSH solutions (FIGS. 14-16). It should be noted that with the settings of the confocal microscope, Applicants found that R is in a reasonable linear relationship with GSH concentrations. This is because $K_d'$ is an instrument dependent parameter and R is proportional to GSH concentrations if $K_d'$ is much larger than 10 mM. Therefore, for all the cell imaging studies, R is plotted against GSH concentrations in standard curves and quantification, instead of $(R-R_{min})/(R_{max}-R)$.

Based on this calibration curve, Applicants first determined the GSH concentration to be 4.6±0.8 mM in HeLa cells (FIG. 14), which is consistent with previously reported values. A representative image is shown in FIG. 14 to demonstrate intracellular distribution of GSH levels. Applicants further expanded the live imaging measurements in several other cell lines, including 3T3-L1, HepG2, PANC-1, and PANC-28 cells. For comparison, Applicants also measured the total amount of GSH in these cell lines using their cell lysate following a well-established protocol. To further convert the amount of GSH into concentrations, Applicants measured the corresponding cell volumes using packed cell volume (PCV) tubes.

FIG. 15 provides confocal fluorescent images of TQ Green absorbed on polystyrene beads in various concentrations of GSH solution. These images were used for calibration of confocal microscope because Applicants encountered a technical difficulty that confocal microscopes are unable to measure the fluorescence intensity of a homogenous solution due to lack of a focal point. To solve this problem, Applicants physically adsorbed TQ Green to the surface of 4.5 μm polystyrene beads, which allowed Applicants to quantify the fluorescence intensity ratio with excitation at 405 and 488 nm in different concentrations of GSH solution.

As shown in FIG. 17, the concentrations measured using TQ Green live imaging are well correlated with the values obtained from bulk lysate measurements. Applicants also note that the correlation line (dashed line in FIG. 17) has a slope of 1.1, indicating that the GSH concentrations from live imaging are ~10% higher than the values measured using lysates. This systemic error may originate from loss of lysate during the cell homogenization process. Alternatively, it is also possible that a systemic error arose because the calibration curve was generated using TQ Green adsorbed onto the surface of polystyrene beads in PBS, which is different from the intracellular environment. In addition, intracellular cysteine may also react with TQ Green to afford an over-estimated GSH concentration using the imaging method (vide supra).

Applicants also note that the GSH level in 3T3-L1 cells based on TQ Green imaging (4.6±0.9 mM) deviates the most from the bulk lysate measurement (2.3±0.4 mM). Applicants noticed that, unlike the spherical cancer cells, 3T3-L1 cells are stellate, which prevents tight packing in the cell volume measurement. Therefore, Applicants suspect that the inconsistency in GSH levels between TQ Green imaging and bulk lysate measurement in 3T3-L1 is due to an overestimation of the 3T3-L1 cell volume, and thus an underestimation of GSH concentration in the lysate. The live imaging method also results in relatively large standard deviations. This is mainly because the imaging method measures GSH concentrations in individual cells and the heterogeneity of the cells broadens the distribution of the measurements. However, this can be advantageous if single cell behavior is the area of interest. Overall, TQ Green enables quantitative measurements of GSH levels in live cells.

TABLE 3

Quantification of GSH levels in different cell lines using live imaging based and lysate based methods.

| | Imaging Based | | Lysate Based | | |
|---|---|---|---|---|---|
| | | | GSH per cell | Cell Volume | |
| | $C_{GSH}$ (mM) | N[a] | (fmol)[b] | (μm³)[c] | $C_{GSH}$ (mM) |
| 3T3-L1 | 4.6 ± 0.9 | 41 | 10.3 ± 0.4 | 4500 ± 700 | 2.3 ± 0.4 |
| HepG2 | 6.2 ± 1.9 | 105 | 16.2 ± 1.5 | 3100 ± 500 | 5.2 ± 0.8 |
| HeLa | 4.6 ± 0.8 | 151 | 13.2 ± 0.9 | 2700 ± 400 | 4.9 ± 0.8 |
| PANC-1 | 6.4 ± 1.8 | 89 | 32.7 ± 3.1 | 4800 ± 700 | 6.8 ± 1.1 |
| PANC-28 | 6.6 ± 1.7 | 80 | 26.7 ± 2.7 | 4900 ± 800 | 5.4 ± 0.9 |

[a]N is the number of cells used for quantification.
[b]Amount of GSH per cell.
[c]Cell volume measured by packed cell volume tubes. The values shown are the average of three measurements. The errors for GSH levels in the lysate measurement mainly originate from the cell volume measurements using packed cell volume tubes.
[d]All the errors represent standard deviations.

To further demonstrate the ability of TQ Green to monitor GSH level changes and the reproducibility of live imaging based measurements, Applicants treated PANC-1 cells with 50 μM of diethyl maleate (DEM) for 24 hours to decrease the GSH levels. Applicants also treated PANC-1 cells with DEM for a very short time to stimulate the uptake of cysteine, thus increasing the GSH levels. After removal of DEM, the cells were further incubated under normal conditions for an additional 22 hours before imaging. As shown in FIG. 18, Applicants observed a 27% decrease and a 28% increase in GSH levels with GSH inhibition and stimulation experiments, respectively ($P<0.001$). Importantly, the GSH level obtained in DEM non-treated cells after 24 hours was essentially the same as the value measured at time zero ($P=0.63$), indicating excellent reproducibility of live imaging based GSH quantification.

The GSH levels are generally cell cycle dependent. Applicants observed the same GSH levels in PANC-1 cells at 0 and 24 hour time points (FIG. 18). The cells used in this experiment were not synchronized. Therefore, the GSH levels reflect an average of cells in different cell cycles. Because of the heterogeneity of the cells, Applicants are unable to determine the concentration changes as a function of time if no stimulating or inhibiting signals are introduced.

Not only is TQ Green capable of quantifying GSH levels in high resolution confocal microscope experiments, but it is also suitable for FACS based bulk cell measurements. PANC-1 cells were treated with DEM under both inhibition and stimulation conditions as described in FIG. 18. After 24 hours, cells were further incubated with TQ Green-AM for 30 minutes and washed with tryptan blue to quench the fluorescence originated from surface bound TQ Green. The fluorescence intensities of each individual cell were quantified using FACS with both 405 nm and 488 nm excitations. As shown in FIG. 19C, the fluorescence ratio of 405 nm and 488 nm, which is positively correlated with GSH levels, changes accordingly upon different cell treatment conditions. It should be noted that in the FACS histograms (FIGS. 19A-B), the 488 nm channel changed significantly under different cell treatment conditions, while the 405 nm channel remained essentially the same. This is because the fluorescence intensities of TQ Green and TQ Green-GSH differ significantly with excitation at 488 nm, but have very similar fluorescence intensities with excitation at 405 nm (FIG. 20). When TQ Green-GSH is formed at the expense of TQ Green, the loss of TQ Green fluorescence at 405 nm excitation coincides with the gain of TQ Green-GSH fluorescence, which makes the 405 nm fluorescence remain unchanged.

In summary, Applicants demonstrated in this Example the importance of reaction reversibility in designing quantitative reaction-based fluorescent probes. Applicants developed the first quantitative imaging of intracellular GSH concentration using a reversible reaction-based ratiometric fluorescent probe. Applicants successfully applied the probe to measure the intracellular GSH concentrations and found the imaging based measurements are well-correlated with lysate based bulk measurements. In addition, Applicants showed that this live imaging method has optimal reproducibility and is able to detect GSH level changes in cells following the stimulation and inhibition effect of DEM. Furthermore, TQ Green is also suitable for GSH measurements using FACS. It should be noted that the reverse reaction between GSH and TQ Green is sluggish (FIG. 4A). For this reason, TQ Green is suitable for one-point measurement or monitoring increases in GSH levels, but is unable to respond quickly to any decreases in GSH concentrations. Another caveat is that TQ Green does not distribute exclusively in cytosol and also penetrates into ER and mitochondria, which were reported to have different GSH levels from the cytosol. Therefore, the imaging analyses of TQ Green should be considered as a measurement of the global GSH level.

Example 1.1. Materials

All the chemicals were purchased from Sigma-Aldrich and Alfa Aesar unless otherwise specified. All solvents and reagents were used as obtained without further purification. Polystyrene beads (4.5 μm, catalog #17135-5) were purchased from Polysciences Inc.

Example 1.2. Instrumentation

NMR spectra were recorded on a Varian NMR ($^1$H at 400 MHz) spectrometer. Chemical shifts (δ) were given in ppm with reference to solvent signals [$^1$H NMR: $CDCl_3$ (7.26), $CD_3OD$ (3.31)]. UV-Vis measurements were performed with 2×10 mm quartz cuvette in Cary 60 UV-is Spectrometer. Fluorescence measurements were performed with the same quartz cuvette in Cary Eclipse Fluorescence Spectrophotometer with an excitation slit of 5 nm, an emission slit of 10 nm and PMT at 650 V. Flash chromatography was performed on a Teledyne ISCO CombiFlashRf200. Olympus FV1000 laser scanning confocal microscope system was used for cell imaging. ESI mass spectrometry was measured on a BrukerMS microTOF ESI, at the Shared Equipment Authority at Rice University. Flow cytometry was performed on BD LSR II Flow Cytometer at BCM core facilities.

Example 1.3. Determination of Equilibrium Constant of TQ Green and GSH Reaction TQ Green was dissolved in PBS buffer (10 mM, pH 7.4) containing 1% DMSO with concentration at 32 μM. GSH was dissolved in the same PBS buffer with concentration from 0-80 mM. Above solutions were mixed at 1:1 ratio. All solutions were protected with nitrogen and stored in glove box to prevent any oxygen entering the solution. Samples of all solutions were taken out at 1, 18, 72, and 144 hours after mixing. UV-Vis and fluorescence were measured for all solutions.

Example 1.4. Cell Culture and Treatment for Imaging

All cell lines used in this study were purchased from American Type Culture Collection (ATCC) and grown in DMEM (Gibco, 11965) media supplemented with 10% FBS and 1% 1003 Pen Strep (Gibco). Cells were cultured under a controlled atmosphere (37° C., 5% $CO_2$). Glass dishes were used for cell culture due to confocal scanning requirements. Cells were treated with TQ Green-AM (20 nM-1 μM with 0.0025-1% DMSO in PBS) for 30 minutes, followed by two washing steps with tryptan blue and PBS prior to imaging. Fluorescent images were acquired with 405 nm laser/430-470 nm filter and 488 nm laser/575-620 nm filter. All the microscope settings were kept consistent in each experiment.

Example 1.5. Calibration for Confocal Microscopy

GSH solutions (0-80 mM in PBS (10 mM, pH 7.4)) were prepared and mixed with TQ Green solution (5 μM final concentration). The above solutions were further mixed with suspension containing 4.5 μm polystyrene beads. Cover glasses were used to hold the solutions for confocal microscopy. Same microscope settings were adopted from prior experiments.

Example 1.6. Subcellular Colocalization Imaging

HeLa cells were cultured on glass bottom dishes as described before. For endosome labeling, cells were transfected with pRab5-RFP 24 hours prior to imaging. For mitochondria labeling, cells were treated with 100 nM MitoTracker® Red CMXRos (catalog #M-7512) in PBS 30 minutes prior to imaging. For ER labeling, cells were treated with 1 μM ER-Tracker™ Red CMXRos (catalog #E34250) in PBS 30 minutes prior to imaging. For lysosome labeling, cells were treated with 50 nM LysoTracker® Red DND-99 (catalog #L-7528) in PBS 120 minutes prior to imaging. All cells were also co-stained with 1 μM TQ Green-AM in PBS 30 minutes prior to imaging. Fluorescent images were acquired with 405 nm laser/430-470 nm filter, 488 nm laser/505-545 nm filter and 559 nm laser/575-620 nm filter.

Example 1.7. Glutathione Reductase Assay and Cell Volume Measurement

The procedure was adopted from literature with minor modification. All cells were grown on six-well plates until the cell number reached about $5\times10^5$ in each well before harvesting. Cells were washed with cold PBS buffer twice and digested by 0.25 mL of trypsin under room temperature (treatment time varies, usually around 5 minutes). Then, 1 mL of fresh medium was added to neutralize and the solution was immediately transferred to a cold 1.5 mL Eppendorf tube. A small sample was used for cell counting every time. The sample was centrifuged at 1000 g for 5 min at 4° C. and the supernatant was discarded. The cell pellet was then washed with PBS and centrifuged again at the same condition. The supernatant was removed and cell-lysis buffer (1 mL 0.1% Triton-X and 0.6% sulfosalicylic acid in EDTA added PBS buffer) was added. Cells were homogenized using a Teflon pestle at 4° C. The suspension was centrifuged at 3000 g for 4 minutes at 4° C., and the supernatant was transferred to a new cold Eppendorf tube that was ready for assay measurement.

In a 96-well microtiter plate, 20 μL of cell lysate samples were placed in each well. Freshly made solutions of 5,5'-dithio-bis(2-nitrobenzoic acid) (DTNB) and glutathione reductase (GR) with concentrations of 0.33 g/L and 1.67 units/mL, respectively, were added to the same well to make the final volume to be 140 μL. After about 30 seconds, 60 μL of β-NADPH (0.67 g/L) was added and the mixture was immediately measured for absorbance at 412 nm every 30 seconds for 2 minutes. The slope of the absorbance changes was proportional to the GSH concentration. A standard curve with known GSH concentrations was used to calibrate all the results. Cell volumes were measured by centrifuging cell suspension (~$4\times10^5$ cells per sample) at 2,500 g for 1 minutes in packed cell volume (PCV) tubes (Sigma-Aldrich, cat. no. Z760986).

Example 1.8. Measurement of GSH Concentration Changes in PANC-1 Cells

PANC-1 cells were incubated with DEM (50 μM) for 2 hours for stimulation of cysteine uptake. After replacing with fresh medium, cells were cultured at normal conditions for another 22 hours. A separate dish of PANC-1 cells were incubated with DEM (50 μM) as an inhibitor for 24 hours. TQ Green-AM (1 μM with 1% DMSO) was used to stain the cells for 30 minutes, followed by two washing steps with tryptan blue and PBS prior to measurement. Same imaging procedures as above were performed. GSH concentrations were calculated based on the calibration curve. FACS was performed from harvested cells after treatment, fluorescent intensities were recorded with 405 nm laser/420-460 nm filter (pacific blue channel), and 488 nm laser/515-545 nm filter (FITC channel). Data were processed with FlowJo.

Example 1.9. Synthesis of Fluorophore (Module A)

Compounds 4a and 4b were synthesized according to the scheme below:

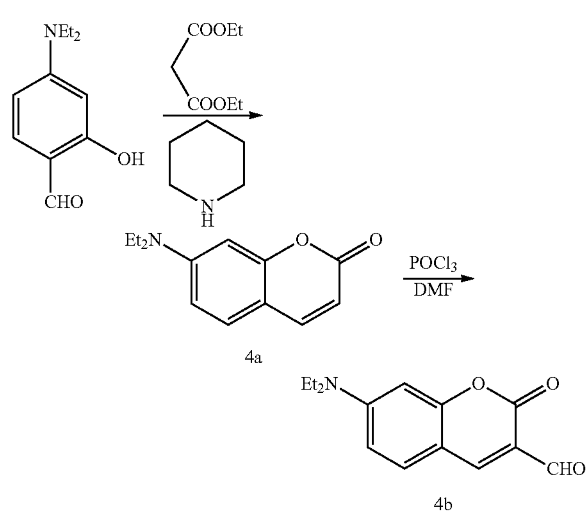

Briefly, 4-diethylaminosalicylaldehyde (1.93 g, 10 mmol), diethylmalonate (3.2 g, 20 mmol) and piperidine (1.0 mL) were mixed in absolute ethanol (30 mL) and refluxed for 18 hours. All volatiles were evaporated under reduced pressure, then a mixture of concentrated HCl (20 mL) and acetic acid (20 mL) was added. Reaction mixture was stirred at 115° C. for 19 hours. The solution was cooled to room temperature and poured into 100 mL of ice water. Upon using NaOH solution (40%) to adjust pH to 5, brown precipitate formed immediately. After stirring for 1 hour and cooling to 4° C., the mixture was filtered, washed with water, and then dried to give the desired product 7-diethylaminocoumarin 4a (2.06 g, 95%).

Anhydrous DMF (6.5 mL) was added dropwise to $POCl_3$ (6.5 mL) at 60° C. under $N_2$ atmosphere and stirred for 30 minutes to yield a red solution. The mixture was added to a solution of 7-diethylaminocoumarin 4a (4.50 g, 20.7 mmol) in DMF (30 mL) to allow a scarlet suspension. The mixture was stirred at 70° C. for 16 hours and then poured into 300 mL of ice water. Upon addition of NaOH (40%) solution to adjust pH to 5, an large amount of precipitate appeared. The crude product was filtered, thoroughly washed with water, dried and recrystallized in absolute ethanol to give the desired compound 4b (3.0 g, 58%). $^1$H-NMR in DMSO-$d_6$ was performed for both compounds and matched reference results.

Example 1.10. Synthesis of Function Ketone (Module C)

Compounds 5a and 5b were synthesized according to the scheme below:

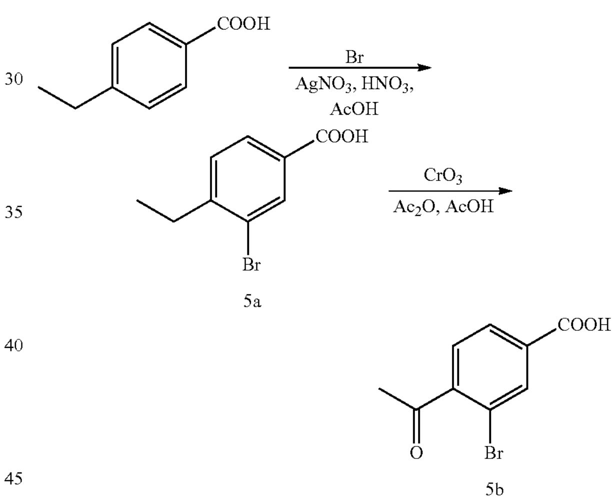

Briefly, bromine (0.7 mL, 14 mmol) was added to a solution of 4-ethylbenzoic acid (1.5 g, 10 mmol) in acetic acid (30 mL), nitric acid (6.5 mL) and water (5 mL). A solution of silver nitrate (1.7 g, 10 mmol) in water was added dropwise with vigorous stirring. The reaction mixture was stirred overnight at room temperature with a large amount of yellow precipitation. Resulting solution was filtrated and all volatile was removed under reduced pressure to yield the crude product as white powder, which was recrystallized in ethyl acetate and hexane to give 3-bromo-4-ethylbenzoic acid 5a (0.9 g, 40%).

Chromium (VI) oxide (2.42 g, 2.42 mmol) was dissolved in a mixture of acetic acid (10 mL) and acetic anhydride (7 mL). A solution of 3-bromo-4-ethylbenzoic acid 5a (1.03 g, 4.52 mmol) in acetic acid (15 mL) was added dropwise. During addition, 3-bromo-4-ethylbenzoic acid 5a partially crushed out. An additional acetic acid (10 mL) was used to rinse 5a and combined with the reaction mixture. The reaction mixture was stirred overnight under nitrogen at room temperature. After addition of water (100 mL), the mixture was extracted with diethyl ether. The collected organic layer was washed with water and then evaporated to give crude product as a white powder, which was then recrystallized in ethyl acetate and hexane to afford 4-acetyl-3-bromobenzoic acid 5b (0.81 g, 74%). $^1$H-NMR in $CDCl_3$ were performed for both compounds and matched with the literature results.

Example 1.11. Synthesis of Michael Acceptor (Module B)

TQ Green and compound 3a were synthesized according to the scheme below:

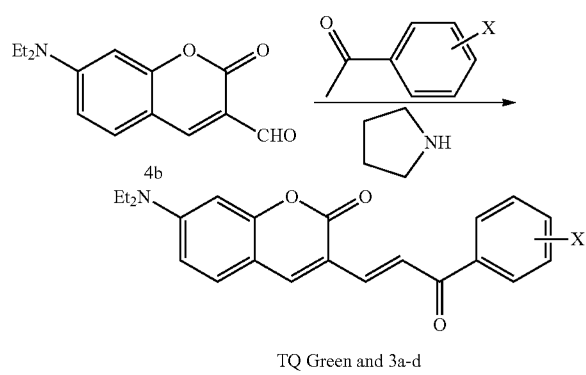

TQ Green and 3a-d

To a solution of 4b (123 mg, 0.500 mmol) and different ketones (1.8 equiv, Table 1) in $CH_2Cl_2$/EtOH (1:1, v/v, 4 mL) was added 2 drops of pyrrolidine. The resulting solution (usually red) was stirred at room temperature for an additional 12 hours to afford a scarlet solution. All solvent was removed under vacuum. The crude product was then purified by reverse phase chromatography (C18 column, elute with ACN in water 5-40%). Then, recrystalization was performed in ethanol to further purify compounds 3a and TQ Green.

The $^1$H-NMR (400 MHz, $CD_3OD$) analysis for compound 3a was as follows: δ 8.20 (s, 1H), 8.13-7.98 (m, 5H), 7.72 (d, J=15.6 Hz, 1H), 7.49 (d, J=9.2 Hz, 1H), 6.78 (dd, J=2.4, 9.2 Hz, 1H), 6.56 (d, J=2.4 Hz, 1H), 3.51 (dd, J=7.2, 14.2 Hz, 4H), 1.23 (t, J=6.8 Hz, 6H); ESI-MS (m/z): $[M+H]^+$ calculated for $C_{23}H_{21}NO_5$, 392.1; found, 392.0.

The $^1$H-NMR (400 MHz, $CD_3OD$) analysis for TQ Green was as follows: δ 8.22 (d, J=1.2 Hz, 1H), 8.06 (s, 1H), 7.98 (dd, J=1.2, 7.8 Hz, 1H), 7.49-7.26 (m, 4H), 6.75 (dd, J=2.8, 9 Hz, 1H), 6.53 (d, J=2.4 Hz, 1H), 3.51 (dd, J=7.2, 14.2 Hz, 4H), 1.21 (t, J=6.8 Hz, 6H); ESI-MS (m/z): $[M+H]^+$ and $[M+2+H]^+$ calculated for $C_{23}H_{20}BrNO_5$, 470.1 and 472.1; found, 469.9 and 471.9.

Example 1.12. Synthesis of Cell Permeable GSH Probe

TQ Green-AM was synthesized according to the scheme below:

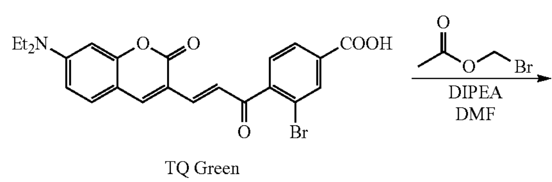

TQ Green

-continued

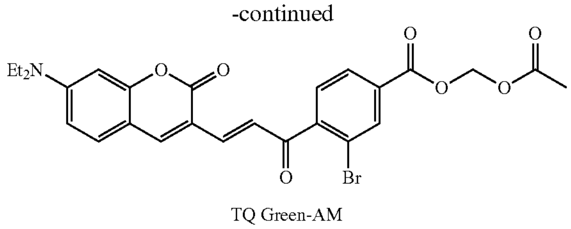

TQ Green-AM

To a TQ Green (5.0 mg, 0.010 mmol) solution in anhydrous DMF (1 mL) were added bromomethyl acetate (0.0062 mL, 0.053 mmol) and DIPEA (0.0075 mL, 0.042 mmol) under nitrogen protection. The reaction mixture was allowed to stir at room temperature overnight, and then concentrated under reduced pressure. The residue was purified by flash column chromatography (elute with hexane in ethyl acetate 20-50%) to afford TQ Green-AM as an orange solid. (4.0 mg, 69%).

The $^1$H-NMR (400 MHz, $CDCl_3$) analysis for TQ Green-AM was as follows: δ 8.30 (d, J=2.0 Hz, 1H), 8.06 (dd, J=2.0, 8.0 Hz, 1H), 7.77 (s, 1H), 7.54-7.29 (m, 4H), 6.60 (dd, J=2.0, 8.0 Hz, 1H), 6.47 (d, J=2.0 Hz, 1H), 6.00 (s, 2H), 3.44 (dd, J=8.0, 16.0 Hz, 4H), 2.15 (s, 3H), 1.23 (t, J=6.8 Hz, 6H).

The 13C-NMR (100 MHz, $CDCl_3$) analysis for TQ Green-AM was as follows: δ 194.02, 169.55, 163.45, 160.04, 156.92, 152.25, 146.15, 145.53, 142.18, 134.74, 131.33, 130.27, 128.93, 126.79, 125.64, 119.58, 114.10, 109.67, 108.81, 96.95, 45.09, 29.67, 20.73, 12.45; ESI-MS (m/z): $[M+H]^+$ and $[M+2+H]^+$ calculated for $C_{26}H_{24}BrNO_7$, 541.1 and 543.1, found, 540.9 and 542.9.

Example 1.13. Determination of Compounds 3a-d and TQ Green Reactivity Against Thiols Compounds 3b-d were dissolved in DMSO (10 mM) and 1 eq of 2 M β-mercaptoethanol (BME) was added. Compounds 3a and TQ Green were dissolved in PBS buffer (10 mM, pH 7.4) with 1% DMSO. GSH solution was added to reach a final concentration of 80 mM with compound 3a at 10 μM and TQ Green at 16 μM, respectively. All solutions were then monitored continuously with UV-Vis and fluorimeter for 2 hours (Table 1).

Example 1.14. Determination of Reaction Kinetics of TQ Green with GSH

GSH in PBS was added to a solution of TQ Green in PBS buffer (10 mM, pH 7.4) containing 1% DMSO. The final concentrations of GSH and TQ Green were 10 mM and 16 μM, respectively. The solutions were then monitored continuously with UV-Vis spectrometer (FIGS. 21A-D).

Example 1.15. Deduction of Ratiometric Quantification

The reversible reaction equation for the probe molecule and GSH can be characterized as follows:

Probe(free)+Anzlyte=Probe+(reacted), or $$P+A=AP$$

According to the reaction equation, the dissociation constant is:

$$K_d = \frac{[P][A]}{[AP]}$$

In the aforementioned equation, [P] and [AP] are the concentrations of free and reacted probes, respectively. Absorptions at two peak wavelengths can be characterized as follows:

$$A_{\lambda 1}=\varepsilon_{P,\lambda 1}[P]+\varepsilon_{AP,\lambda 1}[AP]$$

$$A_{\lambda 2}=\varepsilon_{P,\lambda 2}[P]+\varepsilon_{AP,\lambda 2}[AP]$$

In the aforementioned equation, G is the molar absorption coefficient. Subscripts P and AP stand for free and reacted probes, respectively. The ratio can be deducted as follows:

$$R = \frac{A_{\lambda 1}}{A_{\lambda 2}} = \frac{\varepsilon_{P,\lambda 1}[P] + \varepsilon_{AP,\lambda 1}[AP]}{\varepsilon_{P,\lambda 2}[P] + \varepsilon_{AP,\lambda 2}[AP]}$$

From dissociation constant, Applicants can substitute all [P] with [AP] as follows:

$$[AP] = [P][A]/K_d$$

$$R = \frac{\varepsilon_{P,\lambda 1} + \frac{\varepsilon_{AP,\lambda 1}}{K_d}[A]}{\varepsilon_{P,\lambda 2} + \frac{\varepsilon_{AP,\lambda 2}}{K_d}[A]}$$

Accordingly, the absorption ratio should fit in the following equation, which is not linear to the analyte concentration:

$$R = \frac{\varepsilon_{P,\lambda 1}}{\varepsilon_{P,\lambda 2}} + \frac{\varepsilon_{AP,\lambda 1} - \frac{\varepsilon_{AP,\lambda 1}}{\varepsilon_{AP,\lambda 2}}\varepsilon_{p,\lambda 2}}{\varepsilon_{P,\lambda 2} + \frac{\varepsilon_{AP,\lambda 2}}{K_d}[A]} = P + \frac{Q}{S + T[A]}$$

The equation can be reduced to linear when $\varepsilon_{AP,\lambda 2}=0$ or $K_d$ is much larger than the analyte concentration. Otherwise, the analyte concentration and R follows the relationship below:

$$[A] = K_d\left(\frac{R - \left(\frac{\varepsilon_{P,\lambda 1}}{\varepsilon_{P,\lambda 2}}\right)}{\left(\frac{\varepsilon_{AP,\lambda 1}}{\varepsilon_{AP,\lambda 2}}\right) - R}\right)\left(\frac{\varepsilon_{p,\lambda 2}}{\varepsilon_{AP,\lambda 2}}\right)$$

When there is no analyte present, only pure probe contributes to the absorbance:

$$A_{\lambda 1} = \varepsilon_{P,\lambda 1}[P]$$

$$A_{\lambda_2} = \varepsilon_{P,\lambda 2}[P]$$

$$R = \frac{\varepsilon_{P,\lambda 1}[P]}{\varepsilon_{P,\lambda 2}[P]} = \frac{\varepsilon_{P,\lambda 1}}{\varepsilon_{P,\lambda 2}} = R_{min}$$

When all the probe is saturated by analyte, only bounded probe contributes to the absorbance:

$$A_{\lambda 1} = \varepsilon_{AP,\lambda 1}[P]$$

$$A_{\lambda_2} = \varepsilon_{AP,\lambda 2}[AP]$$

$$R = \frac{\varepsilon_{AP,\lambda 1}[AP]}{\varepsilon_{AP,\lambda 2}[AP]} = \frac{\varepsilon_{AP,\lambda 1}}{\varepsilon_{AP,\lambda 2}} = R_{max}$$

When combined all above together, the following equation arises:

$$[A] = K_d\left(\frac{R - R_{min}}{R_{max} - R}\right)\left(\frac{\varepsilon_{P,\lambda 2}}{\varepsilon_{AP,\lambda 2}}\right)$$

$$[A] = K_d'\frac{R - R_{min}}{R_{max} - R}$$

The following parameters are specific to TQ Green: $\lambda_1$=405 nm, and $\lambda_2$=488 nm.

Example 1.16. Analysis of TQ Green Intracellular Distribution and Accuracy of GSH Quantification The following analysis is based on two assumptions: (1) TQ Green only distributes in cytosol and in lipids that are in contact with cytosol; and (2) the cytosolic GSH is evenly distributed. Assuming the distribution of cytosolic TQ Green reaches equilibrium, the distribution equilibrium can be characterized as follows:

Probe(organic phase)⇆Probe(water phase)

$P_{org} \leftrightarrows P_w$ and $AP_{org} \leftrightarrows AP_w$;

Therefore, $$K_P = \frac{P_{org}}{P_w} \text{ and } K_{AP} = \frac{AP_{org}}{AP_w}$$

In the above equation, $K_P$ and $K_{AP}$ are distribution coefficients of P and AP, respectively. Because analyte (GSH) is only present in water phase in this case, the coupled equilibrium is as follows:

$$P_w + A \rightleftarrows AP_w$$

$$K_d = \frac{[P_w][A]}{[AP_w]}$$

To simplify the analysis, Applicants assume that the spectra of AP and P does not overlap at all. Therefore, the fluorescent intensity at two channels are can be characterized as follows:

$$I_P = \varepsilon_{P,w}[P_w] + \varepsilon_{P,org}[P_{org}] = \varepsilon_{P,w}[P_w] + \varepsilon_{P,org}K_P[P_w] = (\varepsilon_{P,w} + \varepsilon_{P,org}K_P)[P_w] = \varepsilon_P'[P_w]$$

$$I_{AP} = \varepsilon_{AP,w}[AP_w] + \varepsilon_{AP,org}[AP_{org}] = \varepsilon_{AP,w}[AP_w] + \varepsilon_{AP,org}K_{AP}[AP_w] = (\varepsilon_{AP,w} + \varepsilon_{AP,org}K_{AP})[AP_w] = \varepsilon_{AP}'[AP_w]$$

Furthermore, the analyte concentration can be derived as follows:

$$[A] = K_d \frac{[AP_w]}{[P_w]} = K_d \frac{I_{AP} / \varepsilon'_{AP}}{I_P / \varepsilon'_P} = K''_d \frac{I_{AP}}{I_P}$$

In the above equation, the $K_d''$ may not be the same in different environments. Therefore, the analyte concentration [A] is proportional to the fluorescence intensity ratio of AP and P.

Example 1.17. Example of Image Processing and Statistical Analysis

As shown in FIG. 22, a typical image acquired from a confocal microscope contains intensity information from two fluorescent channels. For each cell, the average intensities of the two channels from at least five randomly chosen areas (squares in our case) within the cytosol (nucleus was excluded) were measured. It should be noted that for each matched pair of average intensity values, the data must be measured at the exact same location for reasonable results because the absolute intensities can vary a lot throughout the cell due to probe distribution and heterogeneity within the cell. The ratio was then calculated after subtracting background fluorescence. Bright spots/oversaturated pixels were excluded from statistical analysis based on the dynamic range of the CCD camera (0-4095), as illustrated above at location 8. For each sample, Applicants analyzed the statistical average ratio from at least 30 cells in the confocal images, including the standard curve measured with polystyrene beads (FIGS. 15-16). It should be noted that with the settings of confocal microscopes, Applicants found that R is in a reasonable linear relationship with GSH concentrations. This is because $K_d'$ is an instrument dependent parameter and R is proportional to GSH concentrations if $K_d'$ is much larger than 10 mM. Therefore, for all the cell imaging studies, R, which is $CH_1/CH_2$ in this case, is plotted against GSH concentrations in standard curves and quantification, instead of $(R-R_{min})/(R_{max}-R)$.

Example 1.18. Influence of Instrument on Fluorescence Measurement and Ratiometric Quantitation In some instances, fluorescence measurement may be instrument dependent. Higher energy of the excitation light source can result in higher emission signals. Because the energy distribution at a certain wavelength is different for different light sources, different fluorimeters may exhibit difference in measurements. For the same token, the wavelength dependent sensitivity of fluorimeter detectors also contributes to the instrument dependency of fluorescence measurement (refer to *Anal. Chem.* 2010, 82, 2129-2133 for detailed discussion).

A general misconception in ratiometric quantitation is that ratiometric probes can not only quantify analyte concentrations independent of the probe concentration but also eliminate all other variables, including instrument dependency. However, this notion is wrong for fluorescence measurements, especially in confocal microscope measurements. Because fluorescent intensity is dependent on the energy of the excitation laser beam and the detector responses at different wavelengths, ratiometric measurements are indeed affected by illumination power and detector sensitivity, and thus instrument dependent. In fact, with the same dye solution, different ratios can be obtained based on different instrumental settings. For example, if a hypothetical dye solution X is excited at two wavelengths with different energies, the data shown in Table 4 is what one may expect.

TABLE 4

| | Instrument Setting 1 | | Instrument Setting 2 | | Instrument Setting 3 | |
|---|---|---|---|---|---|---|
| $\lambda_{ex}$ | Excitation Power | Emission Intensity | Excitation Power | Emission Intensity | Excitation Power | Emission Intensity |
| $\lambda_1$ | 100 | 50 | 50 | 25 | 100 | 50 |
| $\lambda_2$ | 100 | 25 | 100 | 25 | 50 | 12.5 |
| Em Ratio of $\lambda_1/\lambda_2$ | 2 | | 1 | | 4 | |

As shown in the table above, different ratios can be obtained by manipulating the energy of the excitation laser. In fact, Applicants observed similar results in their experiments. Therefore, to perform a reliable quantitation, all the calibration and measurements should be done on the same day with the same instrument and the same settings throughout the experiment.

Example 1.18. Evaluation of the Quantum Yield of the GSH Probes

As outlined in Table 1, a series of GSH probes were synthesized following the parental structure 3b (protected 7-Amino coumarin conjugates with phenyl Michael acceptor). The presence of an electron-donating group, such as a methyl group (compound 3c), on module B significantly blocks the Michael addition between thiol and probe. In contrast, decreasing electron density on module B through electron-withdrawing groups on module C (compound 3a and TQ Green) or intramolecular hydrogen bonding (compound 3d), favors the sensing reaction. To facilitate applications in vitro, Applicants chose carboxylic acid as substitutes on module C, because 1) it greatly improves the water solubility of the whole molecule; and 2) it can be modified through esterification to enhance cell permeability. After several iterations, Applicants found that introduction of bromine to module C (TQ Green) can produce a GSH probe with an appropriate equilibrium constant.

As summarized in Table 5, quantum yields of synthesized GSH probes and a GSH adduct with Rhodamine 123 as the standard were analyzed. Quantum yields were determined using a comparative method described previously. The bromine atom on the phenyl ring potentially enhances the push-pull effect of the coumarin-based fluorophore, thus increases the quantum yield.

TABLE 5

| Quantum yields of various GSH probes. | | |
|---|---|---|
| Structure | Solvent | Quantum Yield |
| 3 - TQ Green | Methanol | 0.16 ± 0.05 |
| 3 - TQ Green | PBS | 0.0094 ± 0.0004 |
| TQ Green-GSH | PBS | 0.0059 ± 0.0003 |
| 3a | Methanol | 0.062 ± 0.002 |
| Rhodamine 123 | Methanol | 0.94* |

*Used as standard

Example 2. Probes for Real-Time and Quantitative Monitoring of GSH in Living Cells In this Example, Applicants demonstrate the use of GSH probes to quantitatively monitor the dynamics of GSH concentration change in real-time with subcellular resolution in living cells. The results in this Example also supplement the results in Example 1. The reversibility of the reaction between GSH and a probe is a preferred requirement for ratiometric quantitation. However, two more requirements are also preferred. First, the GSH detection range (as defined by the $K_d$ of the reaction between the probe and GSH) is in the mM range (FIG. 27). Second, in order to be able to measure dynamics of the changes in GSH concentration, the equilibrium reactions are preferably rapid.

Example 2.1. Quantum Mechanical Modeling of Reactions Between GSH and its Probes A proper $K_d$ is important to maximize the signal to noise ratio in the expected range of the analyte concentration. The expected range of [GSH] is 1-10 mM. Therefore, a preferred $K_d$ is about 3 mM, with acceptable values in the range of 1-10 mM. Based on the $\Delta G = RT \ln K_d$ equation, if the desired $K_d$ value is in the range of 1-10 mM, the corresponding Gibbs free energy (ΔG) is in the −4.1 to −2.7 kcal·mol$^{-1}$ range.

In addition to ΔG being in the desired range, Applicants had to insure that the probe can respond to changes in the GSH concentration in seconds. To achieve that feature, Applicants pursued minimization of the activation energies for both forward and reverse reactions when performing quantum mechanical modeling.

Following Houk's work (*The Journal of Organic Chemistry,* 2011, 76, 5074), Applicants applied the M06-2X/6-31+G(d) method with Truhlar's SMD solvation model (*The Journal of Physical Chemistry, B* 2009, 113, 6378) to calculate $K_d$ and the thermodynamic parameters for the reactions between MeSH or its conjugated anion $MeS^-$ and a small library of GSH probes (FIG. 28A). In order to benchmark the computational results, Applicants synthesized this library of GSH probes and measured their equilibrium constants. Both forward and reverse reaction rates with GSH in PBS were measured. Applicants also compared the computational results with the experimental $\Delta G^o$ and discovered that the calculated Gibbs free energies $\Delta G_{calc}$ match the experimental ones with <1.0 kcal·mol$^{-1}$ errors (FIG. 28B). In the kinetic study, Applicants found that a faster forward reaction rate results in a faster reverse counterpart (FIG. 28C). In addition, Applicants found the calculated free energy changes $\Delta G'_{calc}$, for the reactions between $MeS^-$ and the probes are well correlated with the forward reaction rates. In summary, Applicants have validated a computational model to predict the equilibrium constants and the reaction kinetics between the probes and GSH.

Example 2.2. Accelerating the Reaction Rates of Michael Acceptors

Although TQG can reliably perform a "one-point" measurement of GSH levels, it is not able to monitor the GSH concentration changes in real-time due to the slow reaction rate (i.e., the reverse reaction rate in particular). Applicants hypothesized that introducing a cyano substituent, an electron withdrawing group, at the α-position of the Michael acceptor of TQG can stabilize the enolate intermediate and thus enhance the reaction rate. Taking advantage of the established computational model, Applicants calculated $\Delta G'_{calc}$ between TQG-CN and GSH to be −19.76 kcal·mol$^{-1}$, indicating a much faster reaction compared to TQG (FIG. 28A).

However, the $\Delta G_{calc}$ for the same reaction is −1.06 kcal·mol$^{-1}$, which corresponds to a $K_d$ of 166 mM and outside the optimal $K_d$ range. In order to balance the electron withdrawing effect of the cyano group and tune the $K_d$ to the 1-10 mM range, Applicants substituted the phenyl group in TQG-CN with an amino group resulting in $\Delta G_{calc}$ and $\Delta G'_{calc}$ to be −4.16 and −9.50 kcal·mol$^{-1}$, respectively, which are in the desirable range based on Applicants' design criteria. Therefore, Applicants synthesized the new GSH probe, designated as ThiolQuant Green-Real Time 1 (TQG-RT1, FIG. 28A).

TQG-RT1 showed ratiometric fluorescence responses with a wide dynamic range when reacting with GSH. Similar to TQG, TQG-RT1 and its GSH adduct can be excited at 405 and 488 nm, respectively (FIG. 29A). Plotting the ratio of the fluorescence intensities ($F_{405}/F_{488}$) afforded a superb linear relationship ($r^2$=0.9998) with a dynamic range of 0.5-50 mM (FIG. 29B).

One of the caveats of Grx1-roGFP2 is that it is fully reduced in cytosol under physiological conditions, rendering it only sensitive to oxidative stress but insensitive to any "reductive stress". In contrast, considering 1-10 mM of GSH levels in cells, the wide dynamic range of Applicants' probe allows for the monitoring of the changes in GSH levels in both directions. In addition, the ratiometric readouts of TQG-RT1 with and without GSH remain similar in the pH range of 4.5 and 8.2 (FIG. 29C).

Example 2.3. TQG-RT1 Preferentially Reacts with GSH Under Physiological Conditions Previously, Applicants showed that TQG does not react with cysteine and thiolated proteins at their corresponding physiological concentrations. Introduction of cyano group in TQG-RT1 can enhance reactivity but potentially at a cost of reducing the specificity. Therefore, Applicants studied the reactivity of TQG-RT1 towards a panel of common nucleophiles and reactive oxygen/nitrogen species (ROS/RNS). Little consumption of TQG-RT1 was observed in the presence of glycine (10 mM), cysteine (100 μM), albumin (5 mM), and ROS/RNS (100 μM, FIG. 29D). In addition, to assess the reactivity of TQG-RT1 towards highly reactive cysteine residues in some proteins, such as Prx, Applicants adopted two model compounds (FIG. 29D), p-nitrobenzenethiol ($pK_a$=5.1) and p-trifluorobenzenethiol ($pK_a$=5.5). Both thiols are fully deprontonated at pH 7.4, and thus resemble protein reactive cysteine residues. Applicants did not observe significant changes in ratiometric readout of TQG-RT1, indicating that TQG-RT1 preferentially reacts with GSH under physiological conditions.

Example 2.4. TQG-RT1 Responds to GSH Level Changes within 20 Seconds

Applicants applied a stopped-flow instrument to measure the rapid reaction kinetics between TQG-RT1 and GSH at pH 7.4. The reaction kinetics were followed by monitoring the fluorescence changes with excitation at 405 nm. The half-life of TQG-RT1 in the presence of 10 mM of GSH was 1.8 s. Assuming that the forward reaction is a second order reaction, the rate constant then is 38.9 $M^{-1}\cdot s^{-1}$, which is 250 folds faster than TQG. In order to test how fast TQG-RT1 responds to a decrease of GSH level, a pre-equilibrated mixture of TQG-RT1 and GSH was rapidly mixed with an equal volume of PBS. The half-life to re-establish the equilibrium is 2.5 s when decreasing GSH concentration from 10 to 5 mM. In addition, TQG-RT1 can re-establish equilibria within 20 s for all the conditions tested (FIG. 29E). This fast kinetics in both forward and reverse directions enable Applicants to monitor the dynamics of GSH in real-time.

Example 2.5. Use of TQG-RT1 to Monitor GSH Real-Time Dynamics in Living Human Cells To investigate the redox-sensing properties of TQG-RT1 in living cells, Applicants incubated TQG-RT1 in PANC-1 cells for 10 minutes, followed by treatment with a single bolus of 200 μM of $H_2O_2$(Note: Unlike TQG, TQG-RT1 is cell permeable and no esterification is needed). Addition of exogenous $H_2O_2$ to the growth medium led to an immediate and strong oxidative response in cells, resulting in a dramatic decrease of GSH levels (FIG. 30A). It is interesting to note that some cells can rapidly recover from the oxidative insult, while others cannot. If a lower concentration of $H_2O_2$ (50 μM) was used (data not shown), most of the cells can return to the basal GSH levels within 200 seconds, indicating that cells have a limited buffering capacity to oxidative stress. The fast rate of these events is a great illustration of the importance of the fast reaction kinetics of the probe.

Example 2.6. TQG-RT1 for GSH Imaging in Live Animals

In order to further expand the utility of the GSH probes, Applicants tested TQG-RT1 in live animals. *C. elegans* adults are 1 mm long, 100 μm in diameter and whole-body transparent, which make them optimal animal models for optical imaging at the organismal level. Two hour incubation of TQG-RT1 can achieve satisfactory probe uptake in worms (FIG. 30B). It is important to note that a reversible GSH probe is necessary to achieve GSH imaging in live animals due to the delivery barriers and inhomogeneity of the biological system. In contrast, an irreversible GSH probe will react irreversibly at the first contact with GSH and can travel significantly before the measurement leading to wrongful conclusions.

Example 2.7. Synthesis of Fluorophore (Module A)

The synthesis of fluorophore (Module A) is described in Example 1.9.

Example 2.8. Synthesis of Michael Acceptor (Module B)

Compound 3 was synthesized according to the following scheme:

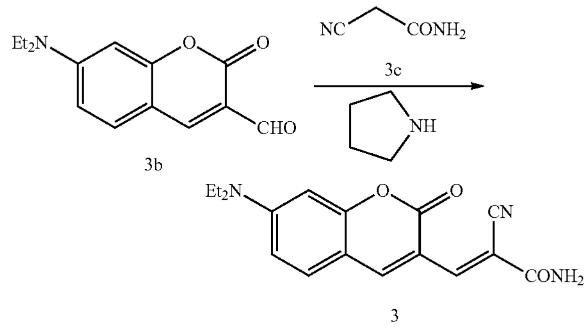

To a solution of compound 3b (123 mg, 0.500 mmol) and 3c (1.8 equiv) in $CH_2Cl_2$/EtOH (1:1, v/v, 4 mL) was added 2 drops of pyrrolidine. The resulting solution (orange to red) was stirred at r.t. for an additional 12 hours to afford a scarlet solution. All the solvent was removed under vacuum. The crude product was then purified by recrystallization in ethanol.

$^1$H-NMR of compound 3 (400 MHz, d6-DMSO) is shown in FIG. 31. The following parameters were obtained: δ 8.65 (s, 1H), 8.11 (s, 1H), 7.8-7.6 (d, J=56 Hz, 2H), 7.57 (d, J=12 Hz, 1H), 6.78 (dd, J=2.4, 12 Hz, 1H), 6.60 (d, J=2.4 Hz, 1H), 3.51 (dd, J=7.2, 14.2 Hz, 4H), 1.12 (t, J=6.8 Hz, 6H). LRMS of compound 3 was calculated for $C_{17}H_{17}N_3O_3$ and found to be 311.13 or 312.1 (M+1).

Example 3. Development and Characterization of Organelle Specific GSH Probes

This Example demonstrates that it is possible to develop GSH probes that include an organelle targeting moiety, such as nuclear targeting moieties, endoplasmic reticulum (ER) targeting moieties, mitochondrial targeting moieties, and combinations thereof.

A few nucleus stains in live cells are commercially available, with Hoechst dyes as one of the most popular choices. A Hoechst tagging strategy which can essentially convert any fluorophores into live cell nucleus stains has been developed (*Chem Commun* (*Camb*)., 2014 Jun. 11; 50(46):6149-52). By utilizing this strategy, it is envisioned that Applicants can develop nucleus targeted GSH probes, designated as TQG-RT-Nuc and TQR-RT-Nuc (FIG. 32).

Likewise, there are a few available ER specific dyes, such as the ER-Tracker™ series probes from Life Technologies. These probes consist of a fluorescent dye and glibenclamide, which binds to the sulfonylurea receptors of ATP-sensitive $K^+$ channels that are abundant on ER. Following a similar concept, Applicants designed ER targeted GSH probes (FIG. 32). These probes can be synthesized by coupling TQG-RT or TQR-RT with a glibenchlamide moiety following previously reported procedures.

Due to the large membrane potential across the mitochondrial inner membrane, lipophilic cations, such as triphenyl phosphonium (TPP), have been successfully applied as mitochondrial targeting ligands. Accordingly, Applicants can also synthesize TPP-GSH probe conjugates, designated as TQG-RT-Mito and TQR-RT-Mito (FIG. 32), to specifically measure the GSH levels in mitochondria Example 4. Thiol Detection by Raman Scattering Microscopy Raman scattering microscopy is an emerging technique used in biological imaging. Cells and biological tissues have very minimal Raman signals in the 1800-2800 $cm^{-1}$ region. Therefore, thiol probes can be designed by combining a Raman marker absorbing in the 1800-2800 $cm^{-1}$ region, such as alkyne, cyano, and azide groups. Some examples of these Raman probes are shown in FIG. 33A. The corresponding Raman frequencies ($cm^{-1}$) of the probes were calculated in a cell transparent region (1800-2800 $cm^{-1}$) using density functional theories. The results are summarized in FIG. 33B.

Another example of a Raman probe is shown in FIG. 33C. The calculated results of the corresponding Raman frequencies ($cm^{-1}$) of the probes in a cell transparent region (1800-2800 $cm^{-1}$) using density functional theories are summarized in FIG. 33D. The aforementioned results demonstrate that the methods and probe molecules of the present disclosure can utilize Raman spectroscopy to detect thiols.

Example 5. Thiol Detection by Magnetic Resonance Imaging (MRI)

Magnetic resonance imaging (MRI) has been widely used in clinic and biomedical research. Fluorine ($^{19}$F) MRI can be used to design ratiometric thiol probes. In the example shown in FIG. 34, the $CF_3$ groups in the probe and adduct molecules have different chemical shifts. Therefore, based on the ratio of the $CF_3$ signal strength in MRI, one can deduce the thiol concentration.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of detecting a thiol in an environment, said method comprising:

exposing the environment to a probe molecule, wherein the probe molecule is selected from the group consisting of

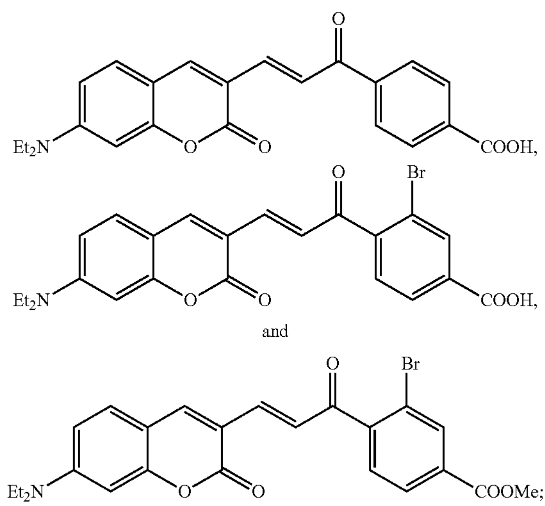

wherein the probe molecule reversibly reacts with the thiol in the environment to form a probe-thiol adduct, thereby causing a ratiometric change in a spectrometric property of the probe molecule and the probe-thiol adduct; and correlating the ratiometric change in the spectrometric property of the probe molecule and the probe-thiol adduct to presence of the thiol in the environment, wherein the correlating comprises quantifying the concentration of the thiol in the environment.

2. The method of claim 1, wherein the thiol is selected from the group consisting of cysteine, homocysteine, glutathione, coenzyme A, and combinations thereof.

3. The method of claim 1, wherein the thiol comprises glutathione.

4. The method of claim 1, wherein the environment is selected from the group consisting of liquids, fluids, organic solvents, thiol-containing solutions, plasma, extracellular fluids, cellular extracts, cells, cytosol, organelles, an in vitro environment, an in vivo environment, and combinations thereof.

5. The method of claim 1, wherein the environment comprises cells.

6. The method of claim 5, wherein the cells are at least part of a tissue, an organ, or an organism.

7. The method of claim 1, wherein the environment comprises an organelle.

8. The method of claim 7, wherein the organelle is selected from the group consisting of nucleus, endoplasmic reticulum, mitochondrion, endosome, lysosome, Golgi apparatus, cell membrane, nuclear membrane, and combinations thereof.

9. The method of claim 1, wherein the environment has a thiol concentration ranging from about 1 fM to about 100 M.

10. The method of claim 1, wherein the exposing comprises incubating the probe molecule with the environment.

11. The method of claim 1, wherein the probe molecule is exposed to the environment at a concentration between about 1 fM and about 100 mM.

12. The method of claim 1, wherein the reversible reaction occurs through a Michael addition reaction.

13. The method of claim 12, wherein the thiol is the Michael donor, and wherein a thiol responsive group on the probe molecule is the Michael acceptor.

14. The method of claim 1, wherein the probe molecule and the thiol have a $K_d$ value that ranges from about 1 pM to about 10 M.

15. The method of claim 1, wherein the probe molecule and the thiol have a $K_d$ value that ranges from about 0.1 mM to about 100 mM.

16. The method of claim 1, wherein a thiol responsive group on the probe molecule selectively reacts with the thiol.

17. The method of claim 1, wherein the ratiometric change in the spectrometric property of the probe molecule and the probe-thiol adduct is selected from the group consisting of a shift in absorption, a shift in fluorescence, a shift in phosphorescence, a shift in luminescence, a shift in fluorescence polarization, a shift in fluorescence lifetime imaging (FLIM), a shift in infrared Raman scattering, a shift in emission spectra, a shift in stimulated emission, a shift in nuclear magnetic resonance (NMR), a shift in magnetic resonance imaging (MRI), a shift in mass spectrometry, a shift in static light scattering, a shift in dynamic light scattering, a shift in refractive index (RI), and combinations thereof.

18. The method of claim 1, wherein the ratiometric change in the spectrometric property of the probe molecule and the probe-thiol adduct comprise a change in an emission spectra.

19. The method of claim 1, wherein the ratiometric change in the spectrometric property of the probe molecule and the probe-thiol adduct comprise a shift in light absorbance wavelength and a shift in fluorescence wavelength.

20. The method of claim 1, wherein the correlating comprises visual detection of the ratiometric change.

21. The method of claim 1, wherein the correlating comprises instrumental detection of the ratiometric change.

22. The method of claim 1, wherein the correlating occurs after equilibrium is established between the probe molecule and the probe-thiol adduct.

23. The method of claim 1, wherein the quantifying occurs by comparing the ratiometric change of the spectrometric property of the probe molecule and the probe-thiol adduct in the environment to a ratiometric change of the spectrometric property of the probe molecule and the probe-thiol adduct in the presence of known concentrations of the thiol.

24. The method of claim 1, wherein the quantifying occurs in real-time.

25. A method of detecting a thiol in an environment, said method comprising:

exposing the environment to a probe molecule, wherein the probe molecule comprises the following structure:

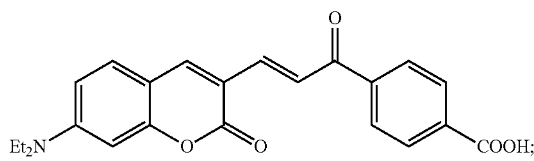

wherein the probe molecule reversibly reacts with the thiol in the environment to form a probe-thiol adduct, thereby causing a ratiometric change in a spectrometric property of the probe molecule and the probe-thiol adduct; and correlating the ratiometric change in the spectrometric property of the probe molecule and the probe-thiol adduct to presence of the thiol in the environment, wherein the correlating comprises quantifying the concentration of the thiol in the environment.

26. A method of detecting a thiol in an environment, said method comprising:

exposing the environment to a probe molecule, wherein the probe molecule comprises the following structure:

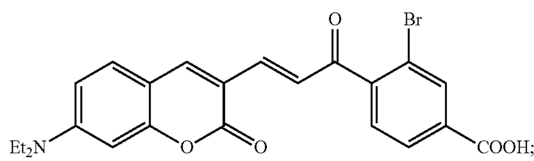

wherein the probe molecule reversibly reacts with the thiol in the environment to form a probe-thiol adduct, thereby causing a ratiometric change in a spectrometric property of the probe molecule and the probe-thiol adduct; and correlating the ratiometric change in the spectrometric property of the probe molecule and the probe-thiol adduct to presence of the thiol in the environment, wherein the correlating comprises quantifying the concentration of the thiol in the environment.

27. A method of detecting a thiol in an environment, said method comprising:

exposing the environment to a probe molecule, wherein the probe molecule comprises the following structure:

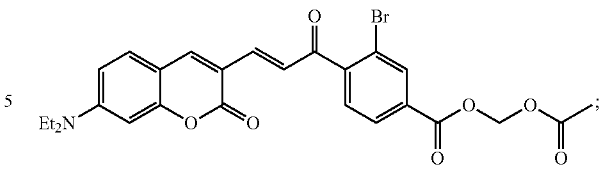

wherein the probe molecule reversibly reacts with the thiol in the environment to form a probe-thiol adduct, thereby causing a ratiometric change in a spectrometric property of the probe molecule and the probe-thiol adduct; and correlating the ratiometric change in the spectrometric property of the probe molecule and the probe-thiol adduct to presence of the thiol in the environment, wherein the correlating comprises quantifying the concentration of the thiol in the environment.

28. A method of detecting a thiol in an environment, said method comprising:

exposing the environment to a probe molecule, wherein the probe molecule is selected from the group consisting of:

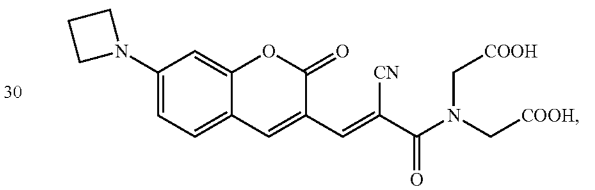

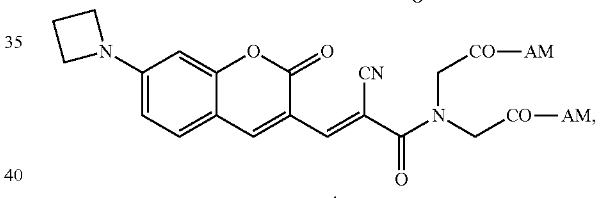

and

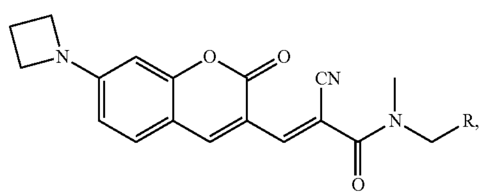

wherein AM comprises —$CH_2OCOCH_3$ and R comprises one of

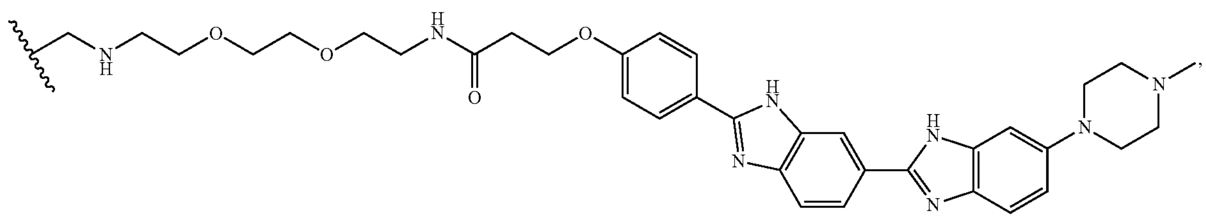

-continued

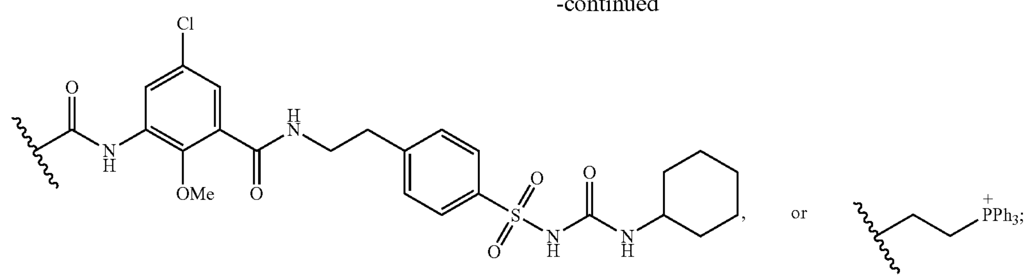

wherein the probe molecule reversibly reacts with the thiol in the environment to form a probe-thiol adduct, thereby causing a ratiometric change in a spectrometric property of the probe molecule and the probe-thiol adduct; and correlating the ratiometric change in the spectrometric property of the probe molecule and the probe-thiol adduct to presence of the thiol in the environment, wherein the correlating comprises quantifying the concentration of the thiol in the environment.

* * * * *